US012617800B2

(12) United States Patent
Luterbacher et al.

(10) Patent No.: US 12,617,800 B2
(45) Date of Patent: May 5, 2026

(54) RENEWABLE MONOMER AND POLYMER THEREOF

(71) Applicant: Ecole Polytechnique Fédérale de Lausanne (EPFL), Lausanne (CH)

(72) Inventors: Jeremy Luterbacher, Chavannes pres Renens (CH); Lorenz Manker, Saint-Sulpice (CH); Graham Dick, Vancouver (CA); Stefania Bertella, Lausanne (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 993 days.

(21) Appl. No.: 17/768,686

(22) PCT Filed: Oct. 14, 2020

(86) PCT No.: PCT/EP2020/078874
§ 371 (c)(1),
(2) Date: Apr. 13, 2022

(87) PCT Pub. No.: WO2021/074211
PCT Pub. Date: Apr. 22, 2021

(65) Prior Publication Data

US 2024/0140961 A1 May 2, 2024

(30) Foreign Application Priority Data

Oct. 14, 2019 (EP) .................................... 19203000

(51) Int. Cl.
*C07D 493/14* (2006.01)
*C08G 63/42* (2006.01)
*C08L 97/02* (2006.01)

(52) U.S. Cl.
CPC ........... *C07D 493/14* (2013.01); *C08G 63/42* (2013.01); *C08L 97/02* (2013.01); *C08G 2230/00* (2013.01); *C08L 2207/20* (2013.01)

(58) Field of Classification Search
CPC .. C07D 493/14; C08G 63/42; C08G 2230/00; C08L 97/02; C08L 2207/20
(Continued)

(56) References Cited

U.S. PATENT DOCUMENTS 6,294,666 B1 9/2001 Hung

FOREIGN PATENT DOCUMENTS

JP 2011021398 A1 2/2011
WO WO 1996/032434 A1 10/1996
WO WO 2017/178513 A1 10/2017

OTHER PUBLICATIONS

Maslinska-Solich et al., Chiral Polymers Containing a Carbohydrate Moiety: Synthesis, 2004, Macromol. Biosci., 4, 421-430 (Year: 2004).*

(Continued)

*Primary Examiner* — Kristin A Vajda
(74) *Attorney, Agent, or Firm* — LEYDIG, VOIT & MAYER, LTD.

(57) ABSTRACT

Described is a compound having the structure (I), (II) or (V), Formulae (I), (II), (V), wherein $R^1$ is —H, —$CH_2OH$ or —$CH(OH)CH_2OH$; $R^2$ is —H, —OH, or —$CH_2OH$; $R^3$ is —H, —OH, or —$CH_2OH$; n is 0 or 1; p is 0 or 1; $R^{10}$ is hydrogen or a hydrocarbon moiety with 1 to 20 carbon atoms, wherein each hydrogen atom of the hydrocarbon moiety may optionally be substituted with a $C_1$-$C_4$-alkyl group or a halogen atom; R is either —Z—F or Y and wherein Z is a hydrocarbon moiety with 0 to 10 carbon atoms, optionally substituted with 1 to 4 C1-C4-alkyl groups or 1 to 4 halogen atoms, and F is —COOH, —$CH(COOH)_2$, —$COOR^4$, —CHO, —$CH(CHO)_2$, —$C_2H_3$, —$C_2H$, —$N_3$, —$NH_2$, —$NHR^7$, —OH, —$CH(CH_2OH)_2$, wherein $R^4$ is a $C_1$-$C_4$-alkyl group and $R^7$ is a $C_1$-$C_4$-alkyl group and wherein Y is hydrogen or a linear, branched or cyclic organic residue having 1 to 20 carbon atoms with the proviso that if R is Y and n is 0 at least one of $R^1$ or $R^2$ is not hydrogen. Also described is a method for the preparation of the compound, a polymer derived from the compound as well as a method for the preparation of the polymer.

(I)

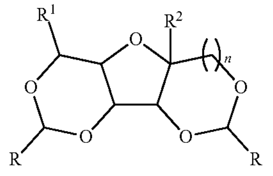

or (II)

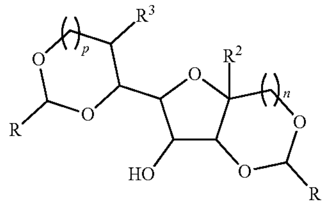

or (V)

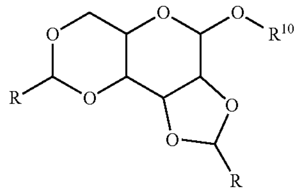

14 Claims, 9 Drawing Sheets

(58) Field of Classification Search
USPC .......................................................... 549/282
See application file for complete search history.

(56) References Cited

OTHER PUBLICATIONS

Jedlinski et al. "Synthesis and configuration of some dialkenylidene derivatives of methyl [alpha]-d-mannopyranoside" Carbohydrate Research, 42(2), 1975, pp. 227-231.
Database Registry [Online] Chemical Abstracts Service, Columbus, Ohio, 2011. XP002801433.
Chakraborty et al. "Synthesis and conformational studies of peptidomimetics containing furanoid sugar amino acids and a sugar diacid" J. Org. Chem. 65 (2), 2000. pp. 6441-6457.
Ferrier et al. "The acid-catalysed condensation of d-xylose with benzaldehyde in the presence of alcohols. Two diastereomeric 1,2:3, 5-di-0-benzylidene-[alpha]-d-xylofuranoses" Carbohydrate Research 5(2), 1967. pp. 132-139.
Forsen et al. "Trichloroethylidene Derivatives of D-Glucose" Acta Chemica Scandinavica, 19, 1965. pp. 359-369.
Frankzkowiak et al. "Synthese phosphat-verbruckter d-glucose-einheiten als telstrukturen phosphorylierter starken" Carbohydrate Research, 158, 1986. pp. 13-35.
Geng et al. "Organocatlysis for the Acid-free 0-Arylidenation of Carbohydrates", Eur. J. Org. Chem. 31, 2013. pp. 7035-7040.
Geyer, R.; Jambeck, J. R.; Law, K. L. Production, Use, and Fate of All Plastics Ever Made. Sci. Adv. 2017, 3 (7), e1700782).
Guiso et al. "Methlyene acetals as protecting groups - an improved preparation method" Tetrahedron Lett. 38 (24) 1997, pp. 4291-4294.
Honeyman et al. "Reactions of methyl [alpha]-D-mannoside with aldehydes" J. Chem. Soc. 1954, pp. 744-746.
International Search Report and Written Opinion, mailed Dec. 23, 2020 for PCT/EP2020/078874.
Klemer et al. "Reaktionen von Acetalen der L-Sorbose mit n-Butyl-lithium" Chem. Ber. 113 (5), 1980. pp. 1761-1767.
Lavilla et al. "Carbohydrate-Based Polyesters Made from Bicyclic Acetalized Galactaric Acid" Biomacromolecules 2011, 12 (7), 2642-2652.
Lavilla et al. "Biodegradable Aromatic Copolyesters Made from Bicyclic Acetalized Galactaric Acid" Journal of Polymer Science Part A: Polymer Chemistry 2012, 50 (16), 3393-3406.
Maslinska-Solich et al. "The formation of a cyclic diacetal of methyl [alpha]-D-mannopyranoside with a 16-membered macrocyclic loop" Chem. Commun. 9 (19), 2002, pp. 984-985.
Mukherjee et al. "Tandem Acetalation-Acetylation of Sugars and Related Derivatives with Enolacetates under Solve-Free Conditions" J. Org. Chem. 72 (23), 2007. pp. 8965-8968.
Muñoz-Guerra et al. "Renewable Terephthalate Polyesters from Carbohydrate-Based Bicyclic Monomers" Green Chem. 2014, 16 (4), 1716-1739).
Sajid et al., Green Chem. 2018, 20 (24), 5427-5453.
Winn et al. "Studies on the formation of a tricyclic C"2-symmetric sulfide", Tetrahedron Lett. 42 (40). 2001. pp. 7091-7093.
Wood et al. "1,2 :3,5-Di-O-benzylidene-[alpha]-D-glucose" J. Am. Chem. Soc. 79(14), 1957. pp. 3862-3864.
Yuceer et al., "Formation of the butylidene acetas of [alpha]chloralose" Carbohydrate Research, 56 (1), 1977. pp. 87-91.
Zamora et al. "Hydrolytic Degradation of Carbohydrate-Based Aromatic Homo- and Co-Polyesters Analogous to PET and PEI" Polymer Degradation and Stability 2006, 91 (11), 2654-2659.
Zheng et al. "Strategies to reduce the global carbon footprint of plastics" Nat. Clim. Chang. 9, 374-378 (2019).

* cited by examiner

RENEWABLE MONOMER AND POLYMER THEREOF

CROSS-REFERENCE TO RELATED APPLICATIONS

This application is a U.S. National Stage Application filed under 35 U.S.C. § 371 of International Application No. PCT/EP2020/078874, filed Oct. 14, 2020, which claims the benefit of European Application No. 19 203 000.5, filed Oct. 14, 2019. Both of these applications are hereby incorporated by reference in their entireties.

BACKGROUND

Plastic has become a ubiquitous consumable in our daily lives. Global plastic production has increased to over 380 million tons per year in 2015 with a compound annual growth rate of 8.5%. Global life-cycle greenhouse gas emissions from production of these plastics were 1.7 Gt of CO2-equivallent (CO2e) in 2015, or 5% of total global greenhouse gas emissions, and is estimated to increase to 6.5 Gt CO2e by 2050 if current trends continue (Zheng, J. & Suh, S. Strategies to reduce the global carbon footprint of plastics. *Nat. Clim. Chang.* 9, 374-378 (2019). Also, more than a third of this plastic has an average lifetime of less than six months before it is discarded—the majority of which ends up in landfills or the environment (Geyer, R.; Jambeck, J. R.; Law, K. L. Production, Use, and Fate of All Plastics Ever Made. *Sci. Adv.* 2017, 3 (7), e1700782). Not only are plastics produced from non-renewable and polluting fossil fuels, but they are also non-biodegradable and detrimental to the world's ecosystems.

To mitigate emissions and pollution from plastic production, research into biobased and biodegradable polymers is sorely needed. In 2018, 2.274 million tons of bioplastic were produced—amounting to less than 1% of global plastic production. Of this 2.274 million tons, 38.7% consists of biodegradable polymers. However, with increasing consumer demand for renewable products, the bioplastics market is expected to expand considerably in the next decade (Biopolymers facts and statistics 2017 report. Institute for Bioplastics and Biocomposites).

Polymers from renewable resources have been developed, but usually their mechanical properties and/or their processability come short of the properties of petroleum-based plastics. The frequently used polymers from renewable resources polylactic acid (PLA), polybutyl succinate (PBS), polyhydroxyalkonates (PHA) are not suitable replacements for packaging materials such as polyethylene terephthalate (PET), the most abundant polyester, which comprises 8% of the global polymer market (Munõz-Guerra, S.; Lavilla, C.; Japu, C.; Martínez de Ilarduya, A. Renewable Terephthalate Polyesters from Carbohydrate-Based Bicyclic Monomers. *Green Chem.* 2014, 16 (4), 1716-1739). This is due to their inferior mechanical properties and processability. Coca-Cola co. and DuPont have commercialized partially renewable PET through the use of renewably derived diols but still have not managed to find a renewable route to economically produce or replace the rigid diacid component, terephthalic acid (TPA).

A satisfying renewable replacement for PET has not been found yet. At the moment, the most promising sustainable replacement candidate for PET appears to be poly(ethylene furanoate) (PEF), which is manufactured from 2,5-furandicarboxylic acid. While PEF may be manufactured from renewable resources, the multi-step reaction sequence from glucose, combined with undesirable degradation products and the intensive separations required prior to polymerization, have limited its commercialization. Furthermore, there have been reports that PEF is non-biodegradable (Sajid et al., *Green Chem.* 2018, 20 (24), 5427-5453).

Renewable polyesters have been prepared using dianhydrohexitols, such as the commercially available isosorbide, which are rigid, bicyclic diols derived from sugars. Polyesters containing these cyclic sugars also have good thermal and mechanical properties and show improved biodegradability (Zamora, F.; Hakkou, K.; Muñoz-Guerra, S.; Galbis, J. A. Hydrolytic Degradation of Carbohydrate-Based Aromatic Homo- and Co-Polyesters Analogous to PET and PEI. *Polymer Degradation and Stability* 2006, 91 (11), 2654-2659). However, the major drawback of these sugars is their low reactivity—caused by the secondary nature of the alcohol groups, and in some cases, the different steric orientations of the hydroxyl groups with respect to the fused rings. In addition, isosorbide is normally obtained by acid catalyzed dehydration of the D-sorbitol. In order to obtain the required purity of the isosorbide monomer, laborious reaction steps including distillation, recrystallization from alcohols, recrystallization from the melt, or a combination of these methods are required. In addition, the synthesis is limited to the diol, and the manufacture of derivatives such as amines requires further synthetic steps.

A similar bicyclic, sugar-derived, diacid (2,3:4,5-di-O-methylene-galactarate) has also been synthesized via acetalization of galactaric acid with formaldehyde in an attempt to directly replace terephthalic acid (TPA). Although high molecular weight polymers with good thermal and mechanical properties and enhanced hydrobiodegradability were attained, the production of these precursors from biomass requires a laborious, multi-step reaction sequence using toxic paraformaldehyde, making commercial synthesis from renewable carbon currently impractical. For example, the production of the glucaric acid-based polymer, which is the most promising candidate for feasible production (as it is produced from glucose), requires the fermentation of glucose to gluconic acid, followed by oxidation of gluconic acid over a Pt/C catalyst to glucaric acid and lastly, reaction with toxic paraformaldehyde to achieve the final product (Lavilla, C.; Alla, A.; Martínez de Ilarduya, A.; Benito, E.; García-Martín, M. G.; Galbis, J. A.; Muñoz-Guerra, S. Carbohydrate-Based Polyesters Made from Bicyclic Acetalized Galactaric Acid. *Biomacromolecules* 2011, 12 (7), 2642-2652; Lavilla, C.; Alla, A.; Martínez de Ilarduya, A.; Benito, E.; García-Martín, M. G.; Galbis, J. A.; Muñoz-Guerra, S. Biodegradable Aromatic Copolyesters Made from Bicyclic Acetalized Galactaric Acid. *Journal of Polymer Science Part A: Polymer Chemistry* 2012, 50 (16), 3393-3406).

Acetals of carbohydrates, such as acetals of glucose, have been prepared. For example, in U.S. Pat. No. 6,294,666, a tricyclic compound prepared by acetalization of glucose is described. However, U.S. Pat. No. 6,294,666 does not describe a polymerizable monomer. Also in WO 96/32434 A1, a tricyclic compound prepared by acetalization of glucose is described as a saccharide residue of polyethylene oxide used for pharmaceutical applications. Also, WO 96/32434 A1 does not describe a polymerizable monomer.

Proceeding from the prior art elucidated hereinabove, it is an object of the invention to provide a monomer that can be polymerized or co-polymerized, in particular, to yield a fully renewable polymer, preferably with potential for biodegradability. Ideally, the polymer or copolymer prepared from the monomer has good thermal and/or mechanical properties.

WO2011/021398 discloses pyranose derivatives and furanose derivatives having a polymerizable group that can be used for a photosensitive resin and a method for producing those pyranose derivatives and furanose derivatives.

Other and more specific objects will in part be apparent and will in part appear hereinafter.

SUMMARY OF THE INVENTION

Some or all of these advantages are achieved according to the invention by the compounds and/or methods described herein and in the present claims.

Further advantageous embodiments of the invention are specified in the dependent claims and are elucidated in detail herein below.

The invention provides for a compound having the structure (I) or (II), or (V)

(I)

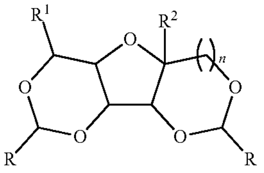

or (II)

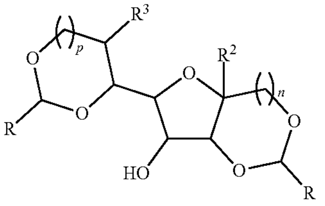

or (V)

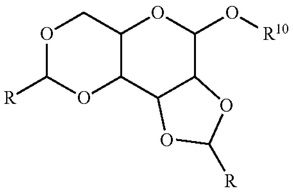

wherein $R^1$ is —H, —$CH_2OH$ or —$CH(OH)CH_2OH$;

$R^2$ is —H, —OH, or —$CH_2OH$;

$R^3$ is —H, —OH, or —$CH_2OH$;

$R^{10}$ is hydrogen or a hydrocarbon moiety with 1 to 20 carbon atoms, wherein each hydrogen atom of the hydrocarbon moiety may optionally be substituted with a $C_1$-$C_4$-alkyl group or a halogen atom;

n is 0 or 1;

p is 0 or 1;

R is either —Z—F or Y, and wherein Z is a hydrocarbon moiety with 0 to 10 carbon atoms, optionally substituted with 1 to 4 $C_1$-$C_4$-alkyl groups or 1 to 4 halogen atoms, and F is —COOH, —$CH(COOH)_2$, —$COOR^4$, —CHO, —$CH(CHO)_2$, —$C_2H_3$, —$C_2H$, —$N_3$, —$NH_2$, —$NHR^7$, —OH, —$CH(CH_2OH)_2$, and Y is a hydrogen or a linear, branched or cyclic organic residue having 1 to 20 carbon atoms, wherein $R^4$ is a $C_1$-$C_4$-alkyl group; and $R^7$ is a $C_1$-$C_4$-alkyl group, with the provision that if R is Y and n is 0 at least one of $R^1$ or $R^2$ is different from hydrogen.

Preferably, if Z is a hydrocarbon moiety with 0 carbon atom, it is a covalent bond.

Preferably, $R^{10}$ can be a substituted or unsubstituted hydrocarbon moiety with 1 to 20 carbon atoms. The term "substituted hydrocarbon moiety with 1 to 20 carbon atoms" stands for a hydrocarbon moiety wherein one or more or all hydrogen atoms may be replaced (substituted) with a $C_1$-$C_4$-alkyl group or a halogen atom. Each of the three hydrogen atoms of the terminal carbon atom of the hydrocarbon moiety can be substituted with a $C_1$-$C_4$-alkyl group or a halogen atom. $R^{10}$ may be for example methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, fluoromethyl, difluoromethyl, trifluoromethyl, fluoroethyl, difluoroethyl, 1-fluoroisopropyl, 1,1-difluoroisopropyl, 1,1,1-trifluoroisopropyl, 1,1,1,2-tetrafluoroisopropyl, pentafluoroisopropyl, hexafluoroisopropyl, and the like.

The —$C_2H_3$ group represents a vinyl group. The —$C_2H$ group represents an ethinyl group. The —$N_3$ group represents an azide group.

For chemical moieties, such as alkyl moieties or aromatic or aliphatic moieties, which are substituted, one of the hydrogen atoms in the moiety is replaced by the substituent. For example, a —$C_6H_4$— moiety that is substituted with a methyl group, corresponds to a —$C_6H_3(CH_3)$-moiety.

Surprisingly, it has been found that using a simple synthetic protocol, it is possible to prepare a polymerizable monomer from renewable resources such as biomass. By using established acetalization chemistry, the compounds reported herein can be obtained. Depending on the additional functional group connected to the aldehyde, monomers with different functionalities can be obtained. In the alternative, acetalization can be conducted using an aldehyde with the functional group that can be easily transformed into other functional groups including, but not limited to, vinyl, alcohol, amine, and azide groups. Accordingly, polyesters, polyamides, or other types of polymers can be prepared from the compounds reported herein. Without wishing to be bound by scientific theory, the fused rings in the structures (I), (II) and (V) are believed to provide polymers prepared from the compounds described herein with good thermal and/or mechanical properties. These properties are found in PET and PEF, which are made from terephthalic acid and furandicarboxylic acid. Thus, the present invention provides for the first-time monomers from renewable resources using biodegradable carbohydrates, which can be manufactured in a simple process directly from biomass.

The invention also provides for a method for the preparation of the compound according to the invention or a composition comprising at least two different compounds according to the invention, having one of the structures (I), (II) or (V)

(I)

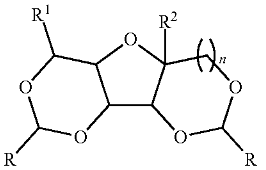

or

-continued (II)

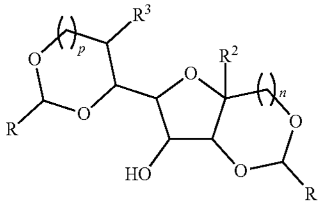

or (V)

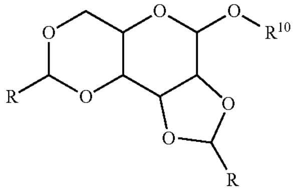

wherein

R, $R^1$, $R^2$, $R^3$, $R^{10}$, n, and p are as defined herein, comprising the steps of a. providing a carbohydrate or a lignocellulose-containing composition;

b. adding an aldehyde optionally comprising at least one functional group selected from the group consisting of carboxylic acid, carboxylic amide, ether, alkyne, alkene, aldehyde, chloride, hydroxyl, and azide, carboxylic acid ester, aldehyde, vinyl, and amine to the carbohydrate or to the lignocellulose-containing composition to obtain a mixture;

c. heating the mixture under acidic conditions and d. separating, in particular isolating, the compound according to the invention or the composition comprising at least two different compounds according to the invention, having one of the structures (I), (II) or (V)

(I)

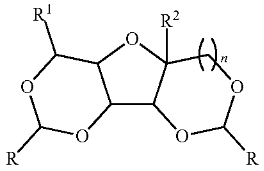

or (II)

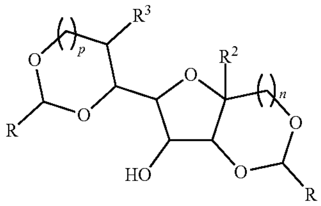

or (V)

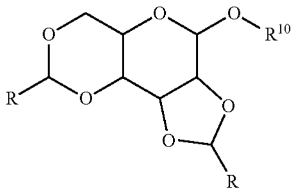

wherein R, $R^1$, $R^2$, $R^3$, $R^{10}$, n, and p are as defined herein.

Preferably, said at least one functional group is selected from the group consisting of carboxylic acid, carboxylic amide, ether, aldehyde, chloride, and hydroxyl.

The invention also provides for a polymer comprising as repeat unit (III)

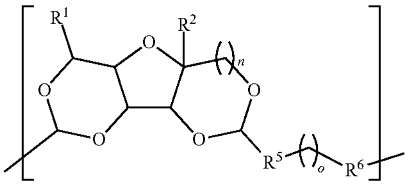

and/or (IV)

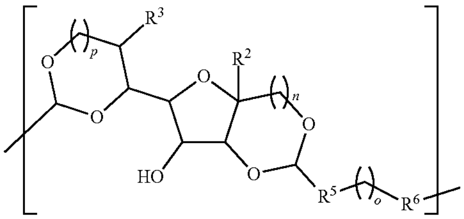

and/or (VI)

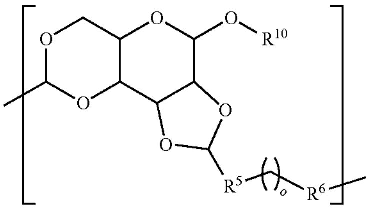

wherein $R^1$, $R^2$, $R^3$, $R^{10}$, n, and p are as defined herein; and $R^5$ is —Z—$F^1$— or $Y^1$ and $R^6$ is —$F^2$—Z— or $Y^1$, wherein Z is a hydrocarbon moiety with 0 to 10 carbon atoms, optionally substituted with 1 to 4 $C_1$-$C_4$-alkyl groups or 1 to 4 halogen atoms, and wherein $F^1$ is —C(═O)O—, —OC(═O)—, —C(═O)$NR^8$—, —$R^8$NC(═O)—, or a covalent bond, and $F^2$ is —OC(═O)—, —C(═O)O—, —$R^8$NC(═O)—, —C(═O)$NR^8$—, or a covalent bond;

wherein $R^8$ is H or a $C_1$-$C_4$-alkyl group; and o is an integer from 2 to 10, in particular from 2 to 4; and $Y^1$ is a linear, branched or cyclic organic residue having 1 to 20 carbon atoms with the proviso that if $R^5$ and $R^6$ are $Y^1$ and n is 0 at least one of $R^1$ or $R^2$ is different from hydrogen.

The invention also provides for a method for the preparation of a polymer according to the invention, wherein at least one compound according to the invention is subjected to a reaction, optionally with a compound with the formula $R^9$-L-$R^{9A}$, wherein L is selected from the group consisting of $(CH_2)_O$ (VII), CO (VIII) and diphenyl sulfone (IX)

(VII)

(VIII)

-continued (IX)

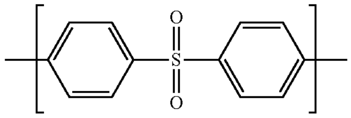

$R^9$ and $R^{9A}$ are independently selected from the group consisting of —$OR^{11}$, —OH, —$NR^8$, COOH, $COOR^4$ and a halogen atom;

wherein $R^{11}$ is selected from the group consisting of aryl and alkyl or $R^{11}$ of residue $R^9$ and $R^{11}$ of residue $R^{9A}$ form together a ring system;

wherein the halogen atom is selected from the group consisting of fluorine, chlorine, bromine and iodine; and wherein $R^4$, $R^8$ and o are as defined herein.

Lastly, the invention also provides for the use of the polymer according to the invention for the manufacture of sheets, fibers or molded objects, in particular as a replacement for poly(ethylene terephthalate).

PREFERRED EMBODIMENTS

The Compound According to the Invention

Figure 1:
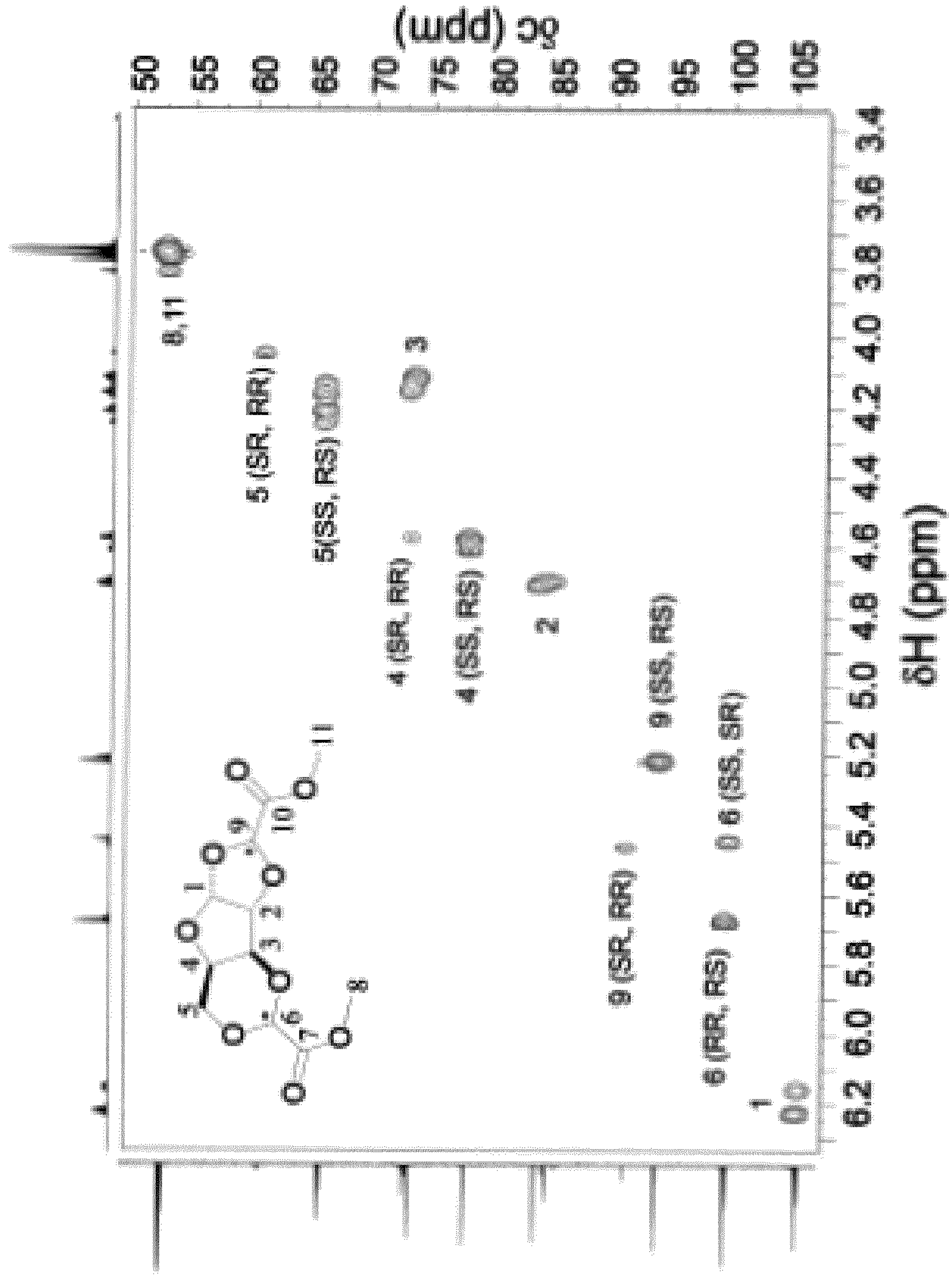
FIG. 1 shows a 2D HSQC NMR spectrum of dimethylglyoxylate xylose (DMGX) isomers in DMSO-d6.

The structures (I), (II) and (V) are preferably obtained from carbohydrates such as aldoses or ketoses by reaction with an aldehyde. The skilled person is aware about the implications this has on the stereochemistry of the compounds and polymers reported herein.

The residues $R^1$, $R^2$, $R^3$ and $R^{10}$ particularly differ depending on the type of carbohydrate from which the structures (I), (II) or (V) have been obtained. If the structures (I), (II) or (V) have been obtained from aldoses, $R^1$ may be —H, —$CH_2OH$ or —$CH(OH)CH_2OH$, $R^2$ may be —H, and $R^3$ may be —H, —OH, or —$CH_2OH$. If the structures (I), (II) or (V) have been obtained from ketoses, $R^1$ may be —H or —$CH_2OH$, $R^2$ may be —OH or —$CH_2OH$, and $R^3$ may be —H.

Accordingly, the compound according to the invention may preferably have one of the following structures:

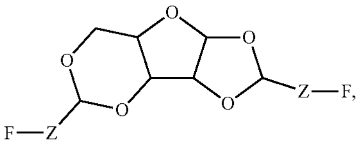

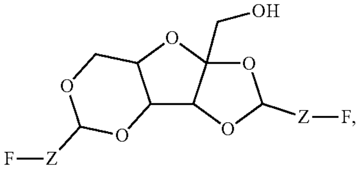

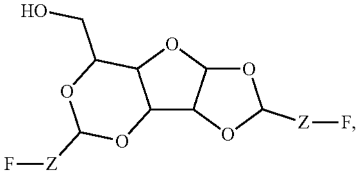

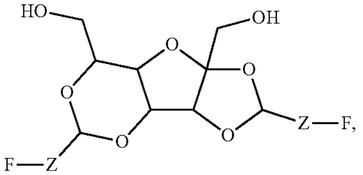

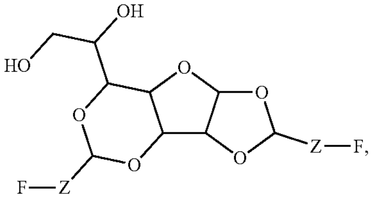

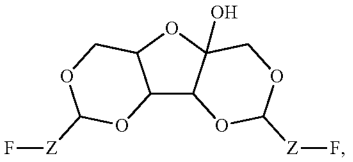

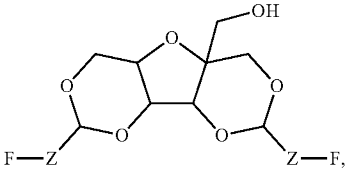

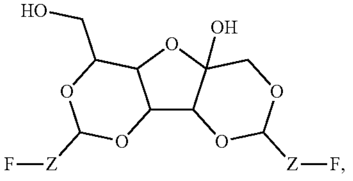

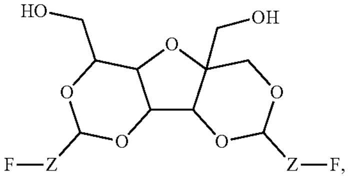

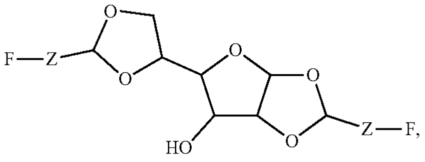

-continued

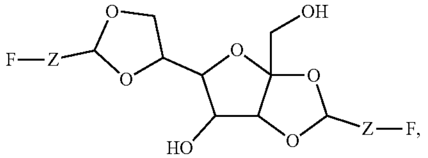

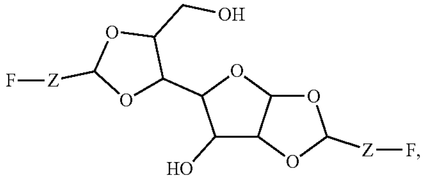

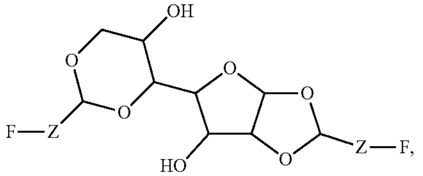

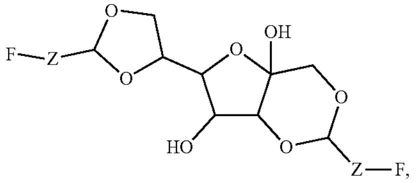

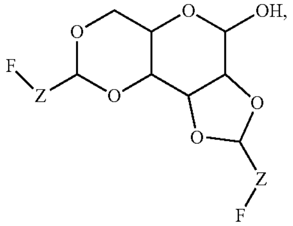

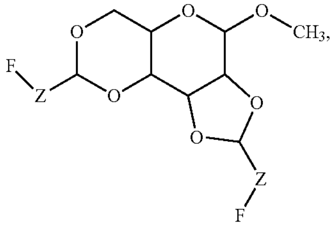

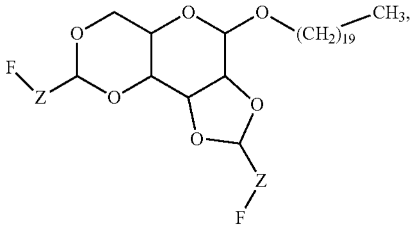

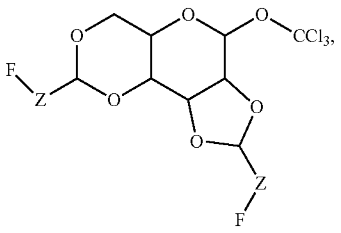

-continued

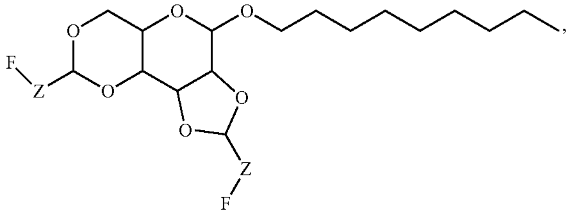

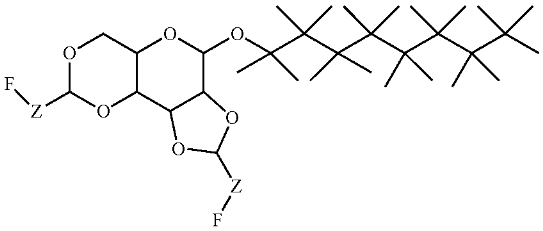

or

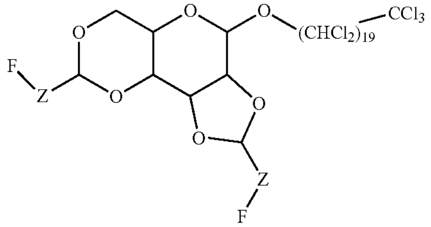

wherein Z is a hydrocarbon moiety with 0 to 10 carbon atoms, optionally substituted with 1 to 4 $C_1$-$C_4$-alkyl groups or 1 to 4 halogen atoms, and F is —COOH, —$CH(COOH)_2$, —$COOR^4$, —CHO, —$CH(CHO)_2$, —$C_2H_3$, —$C_2H$, —$N_3$, —$NH_2$, —$NHR^7$, —OH, —$CH(CH_2OH)_2$, wherein $R^4$ is a $C_1$-$C_4$-alkyl group and $R^7$ is a $C_1$-$C_4$-alkyl group.

More preferably, the compound according to the invention has the structure

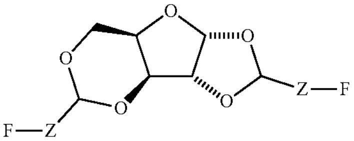

or

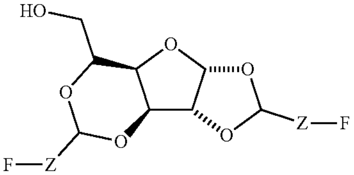

or

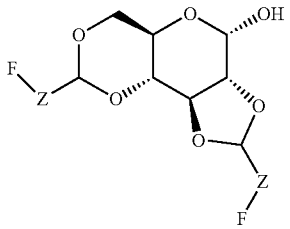

or

-continued

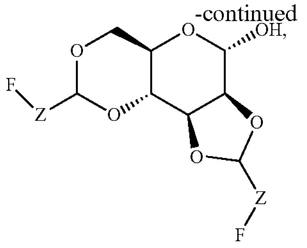

in particular

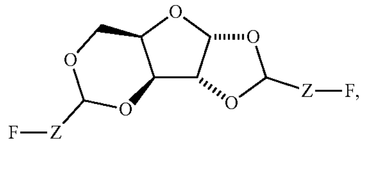

wherein Z is a hydrocarbon moiety with 0 to 10 carbon atoms, optionally substituted with 1 to 4 $C_1$-$C_4$-alkyl groups or 1 to 4 halogen atoms, and F is —COOH, —CH(COOH)$_2$, —COOR$^4$, —CHO, —CH(CHO)$_2$, —$C_2H_3$, —$C_2H$, —$N_3$, —$NH_2$, —NHR$^7$, —OH, —CH($CH_2OH$)$_2$, wherein $R^4$ is a $C_1$-$C_4$-alkyl group; and $R^7$ is a $C_1$-$C_4$-alkyl group.

Z is preferably —$(CH_2)_m$—, wherein m is an integer from 0 to 10, in particular from 0 to 4; —$C_6H_4$—, wherein the aromatic ring is optionally substituted with 1 to 4 $C_1$-$C_4$-alkyl groups or 1 to 4 halogen atoms; or —$C_6H_{10}$—, wherein the aliphatic ring is optionally substituted with 1 to 4 $C_1$-$C_4$-alkyl groups. F is preferably —COOH, —COOR$^4$, —$C_2H_3$, —$C_2H$, or —$N_3$, wherein $R^4$ is a $C_1$-$C_4$-alkyl group.

Preferably, $R^2$ is —H. More preferably, $R^2$ is H, $R^1$ is H or $CH_2OH$, and $R^3$ is —H.

In the structures (I) and (II), n is preferably 0. This is particularly the case when the structures (I) or (II) have been obtained from aldoses.

Preferably, the compound has the structure (I). Compounds with the structure (I) are rigid monomers that impart good thermal and/or mechanical properties to the polymer.

Very good results have been obtained when the compound has the structure (I), $R^2$ is H and $R^1$ is H or $CH_2OH$, in particular $R^1$ is H.

In the structures (I), (II) and (V), R may comprise a hydrocarbon moiety and a functional group. Advantageously, the hydrocarbon moiety is an alkylene moiety with 0 to 10, preferably 0 to 4, carbon atoms. The hydrocarbon moiety may also be an aromatic ring system with 5 to 10, preferably 6, carbon atoms. The hydrocarbon moiety may also be a cyclic aliphatic ring system with 5 to 10, preferably 6, carbon atoms. The functional group that may be comprised in R may be selected from the group consisting of —COOH, —CH(COOH)$_2$, —COOR$^4$, —CHO, —CH(CHO)$_2$, —$C_2H_3$, —$NH_2$, —$C_2H$, —$N_3$, —NHR$^7$, —OH, and —CH($CH_2OH$)$_2$, preferably from the group consisting of —COOH, —COOR$^4$, —$NH_2$, —NHR$^7$, and —OH, more preferably from the group consisting of —COOH and —COOR$^4$, wherein $R^4$ is a $C_1$-$C_4$-alkyl group and $R^7$ is a $C_1$-$C_4$-alkyl group. R may also consist of one of the aforementioned functional groups.

As described, in the structures (I), (II) and (V), R is —Z—F, wherein Z is a hydrocarbon moiety with 0 to 10 carbon atoms, optionally substituted with 1 to 4 $C_1$-$C_4$-alkyl groups or 1 to 4 halogen atoms, and F is —COOH, —CH(COOH)$_2$, —COOR$^4$, —CHO, —CH(CHO)$_2$, —$C_2H_3$, —$C_2H$, —$N_3$, —$NH_2$, —NHR$^7$, —OH, —CH($CH_2OH$)$_2$, wherein $R^4$ is a $C_1$-$C_4$-alkyl group; and $R^7$ is a $C_1$-$C_4$-alkyl group According to an embodiment of the invention, in the structures (I), (II) and (V), R is preferably —$(CH_2)_m$COOH; —$C_6H_4$COOH, wherein the aromatic ring is optionally substituted with 1 to 4 $C_1$-$C_4$-alkyl groups or 1 to 4 halogen atoms; —$C_6H_{10}$COOH, wherein the aliphatic ring is optionally substituted with 1 to 4 $C_1$-$C_4$-alkyl groups; —$(CH_2)_m$CH(COOH)$_2$;

—$(CH_2)_m$COOR$^4$; —$C_6H_4$COOR$^4$, wherein the aromatic ring is optionally substituted with 1 to 4 $C_1$-$C_4$-alkyl groups or 1 to 4 halogen atoms; —$C_6H_{10}$COOR$^4$, wherein the aliphatic ring is optionally substituted with 1 to 4 $C_1$-$C_4$-alkyl groups; —$(CH_2)_m$CH(COOR$^4$)$_2$;

—$(CH_2)_m$CHO; —$C_6H_4$CHO, wherein the aromatic ring is optionally substituted with 1 to 4 $C_1$-$C_4$-alkyl groups or 1 to 4 halogen atoms; —$C_6H_{10}$CHO, wherein the aliphatic ring is optionally substituted with 1 to 4 $C_1$-$C_4$-alkyl groups; —$(CH_2)_m$CH(CHO)$_2$;

—$(CH_2)_m C_2H_3$; —$C_6H_4C_2H_3$, wherein the aromatic ring is optionally substituted with 1 to 4 $C_1$-$C_4$-alkyl groups or 1 to 4 halogen atoms; —$C_6H_{10}C_2H_3$, wherein the aliphatic ring is optionally substituted with 1 to 4 $C_1$-$C_4$-alkyl groups; —$(CH_2)_m$CH($C_2H_3$)$_2$;

—$(CH_2)_m C_2H$; —$C_6H_4C_2H$, wherein the aromatic ring is optionally substituted with 1 to 4 $C_1$-$C_4$-alkyl groups or 1 to 4 halogen atoms; —$C_6H_{10}C_2H$, wherein the aliphatic ring is optionally substituted with 1 to 4 $C_1$-$C_4$-alkyl groups;

—$(CH_2)_m N_3$; —$C_6H_4N_3$, wherein the aromatic ring is optionally substituted with 1 to 4 $C_1$-$C_4$-alkyl groups or 1 to 4 halogen atoms; —$C_6H_{10}N_3$, wherein the aliphatic ring is optionally substituted with 1 to 4 $C_1$-$C_4$-alkyl groups;

—$(CH_2)_m NH_2$; —$C_6H_4NH_2$, wherein the aromatic ring is optionally substituted with 1 to 4 $C_1$-$C_4$-alkyl groups or 1 to 4 halogen atoms; —$C_6H_{10}NH_2$, wherein the aliphatic ring is optionally substituted with 1 to 4 $C_1$-$C_4$-alkyl groups; —$(CH_2)_m$CH ($NH_2$)$_2$;

—$(CH_2)_m$NHR$^7$; —$C_6H_4$NHR$^7$, wherein the aromatic ring is optionally substituted with 1 to 4 $C_1$-$C_4$-alkyl groups or 1 to 4 halogen atoms; —$C_6H_{10}$NHR$^7$, wherein the aliphatic ring is optionally substituted with 1 to 4 $C_1$-$C_4$-alkyl groups; —$(CH_2)_m$CH(NHR$^7$)$_2$;

—$(CH_2)_m$OH; —$C_6H_4$OH, wherein the aromatic ring is optionally substituted with 1 to 4 $C_1$-$C_4$-alkyl groups or 1 to 4 halogen atoms; —$C_6H_{10}$OH, wherein the aliphatic ring is optionally substituted with 1 to 4 $C_1$-$C_4$-alkyl groups; or —$(CH_2)_m$CH($CH_2OH$)$_2$, wherein $R^4$ is a $C_1$-$C_4$-alkyl group;

$R^7$ is a $C_1$-$C_4$-alkyl group; and m is an integer from 0 to 10, in particular from 0 to 4.

More preferably, in the structures (I), (II) and (V), R is

—$(CH_2)_m$COOH; —$C_6H_4$COOH, wherein the aromatic ring is optionally substituted with 1 to 4 $C_1$-$C_4$-alkyl groups or 1 to 4 halogen atoms; —$C_6H_{10}$COOH, wherein the aliphatic ring is optionally substituted with 1 to 4 $C_1$-$C_4$-alkyl groups; —$(CH_2)_m$CH(COOH)$_2$;

—$(CH_2)_m$COOR$^4$; —$C_6H_4$COOR$^4$, wherein the aromatic ring is optionally substituted with 1 to 4 $C_1$-$C_4$-alkyl groups or 1 to 4 halogen atoms; —$C_6H_{10}$COOR$^4$, wherein the aliphatic ring is optionally substituted with 1 to 4 $C_1$-$C_4$-alkyl groups; —$(CH_2)_m CH(COOR^4)_2$, wherein $R^4$ is a $C_1$-$C_4$-alkyl group;

$R^7$ is a $C_1$-$C_4$-alkyl group; and m is an integer from 0 to 10, in particular from 0 to 4.

Very good results have been obtained when R is —$(CH_2)_m$ $COOR^4$; —$C_6H_4COOR^4$, wherein the aromatic ring is optionally substituted with 1 to 4 $C_1$-$C_4$-alkyl groups; —$C_6H_{10}COOR^4$, wherein the aliphatic ring is optionally substituted with 1 to 4 $C_1$-$C_4$-alkyl groups; or —$(CH_2)_m CH(COOR^4)_2$, wherein m is 0 to 4, and $R^4$ is a $C_1$-$C_4$-alkyl group. Preferably, R is —COOMe.

The aforementioned hydrocarbon moieties are normally part of easily accessible aldehydes. In case these aldehydes are not available, the compounds can be obtained by functional group transformations, for example reductive amination or hydroaminations. Further, the aforementioned functional groups of the residues R allow to prepare polymers from the compounds with structures (I) and (II) with good thermal and/or mechanical properties. In particular, the thermal and/or mechanical properties can be tailored by choosing particular hydrocarbon moieties such as a cyclic aromatic or aliphatic ring system for more rigid polymers, or an alkylene moiety for more flexible polymers. The aforementioned functional groups provide access to a range of different types of polymers such as polyesters, polyamides, or polyethers. Polyesters have the particular advantage that they are very often biodegradable.

According to an embodiment of the invention, R is —$(CH_2)_m COOH$, —$(CH_2)_m CH(COOH)_2$, —$(CH_2)_m$ $COOR^4$, —$(CH_2)_m CH(COOR^4)_2$, —$(CH_2)_m CHO$, —$(CH_2)_m$ $CH(CHO)_2$; —$(CH_2)_m C_2H_3$, —$(CH_2)_m CH(C_2H_3)_2$, —$(CH_2)_m C_2H$, —$(CH_2)_m N_3$, —$(CH_2)_m NH_2$, —$(CH_2)_m CH(NH_2)_2$, —$(CH_2)_m NHR^7$, —$(CH_2)_m OH$, or —$(CH_2)_m CH(CH_2OH)_2$, wherein $R^4$ is a $C_1$-$C_4$-alkyl group, preferably a —$CH_3$ group; $R^7$ is a $C_1$-$C_4$-alkyl group; and m is an integer from 0 to 10, preferably from 0 to 4, more preferably 0.

Optimal results have been obtained when the compound has the structure (I), R is —$(CH_2)_m COOH$, —$(CH_2)_m CH(COOH)_2$, —$(CH_2)_m COOR^4$, —$(CH_2)_m CH(COOR^4)_2$, —$(CH_2)_m CHO$, —$(CH_2)_m CH(CHO)_2$; —$(CH_2)_m C_2H_3$, —$(CH_2)_m CH(C_2H_3)_2$, —$(CH_2)_m C_2H$, —$(CH_2)_m N_3$, —$(CH_2)_m NH_2$, —$(CH_2)_m CH(NH_2)_2$, —$(CH_2)_m NHR^7$, —$(CH_2)_m OH$, or —$(CH_2)_m CH(CH_2OH)_2$, wherein $R^4$ is a $C_1$-$C_4$-alkyl group, preferably a —$CH_3$ group; $R^7$ is a $C_1$-$C_4$-alkyl group; and m is 0. More preferably, $R^2$ is H and $R^1$ is H or $CH_2OH$, in particular $R^1$ is H.

In a preferred embodiment of the invention good results have been obtained when Y is hydrogen or a linear or branched organic residue with 1 to 10 carbon atoms, more preferably 1 to 7 carbon atoms, most preferably 1 to 3 carbon atoms, that is, for example a hydrocarbon moiety such as methylene, ethylene, propylene.

Thus, preferably, the compound according to the invention has one of the following structures:

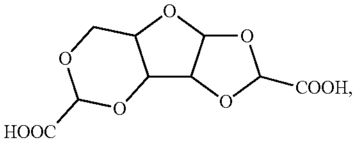

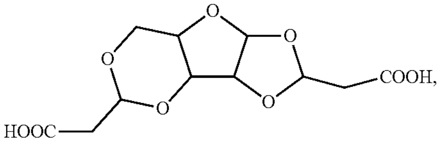

-continued

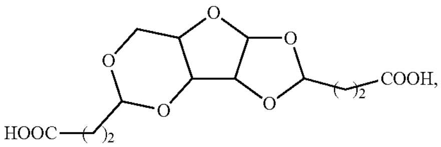

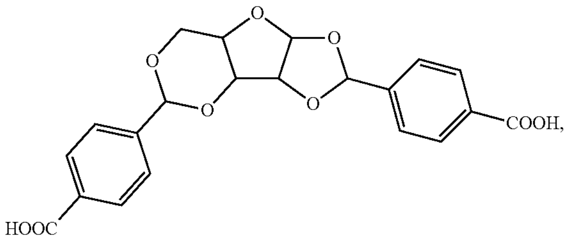

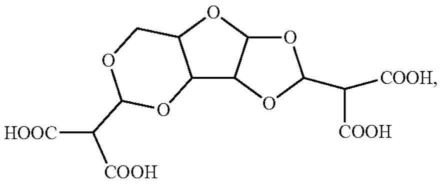

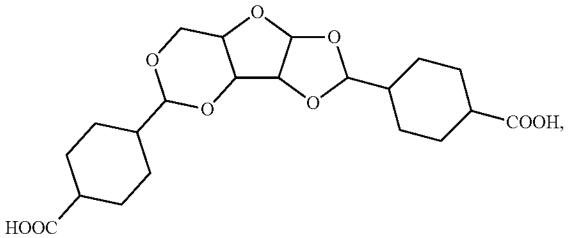

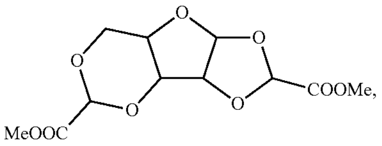

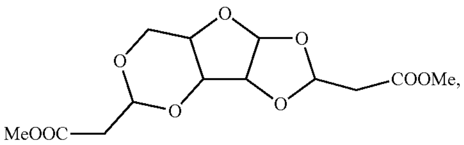

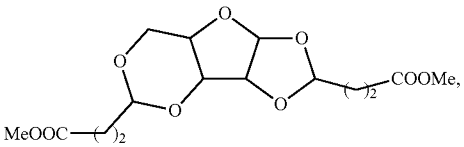

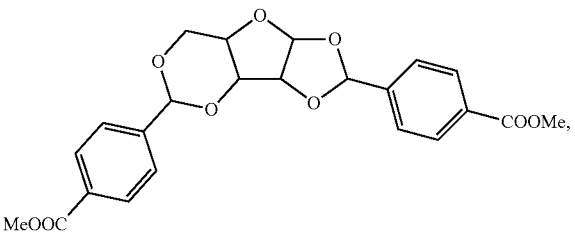

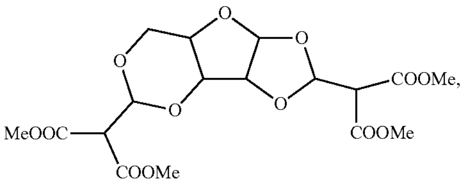

-continued
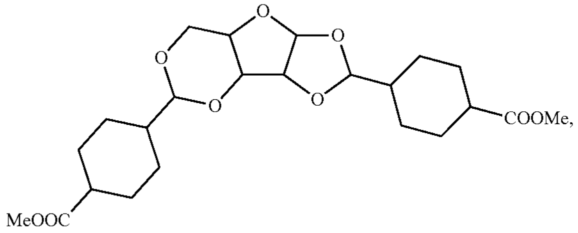
,
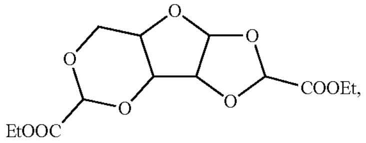
,
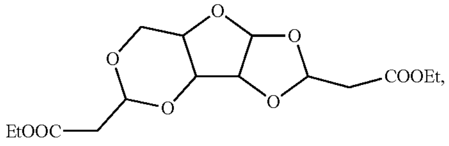
,
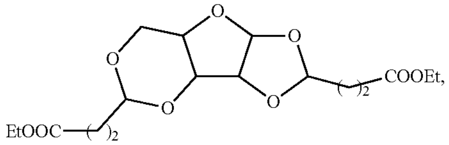
,
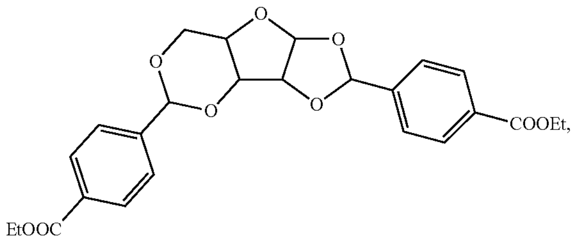
,
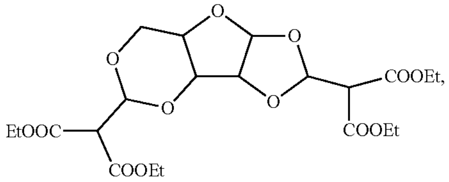
,
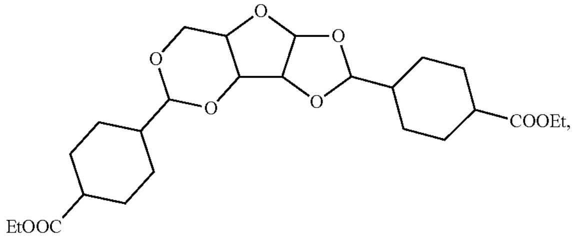
,
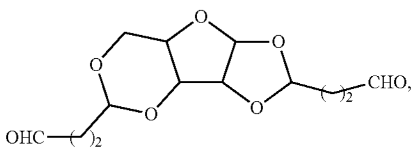
,
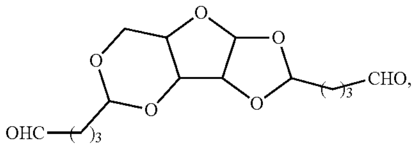
,
-continued
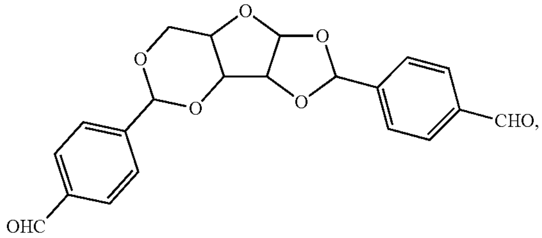
,
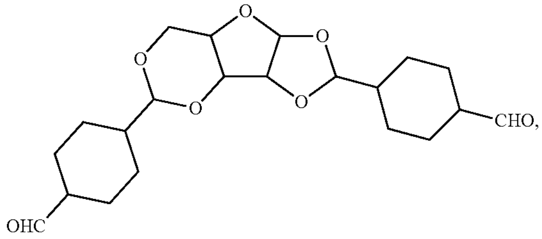
,
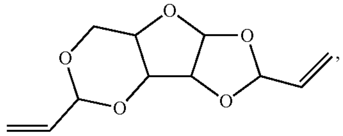
,
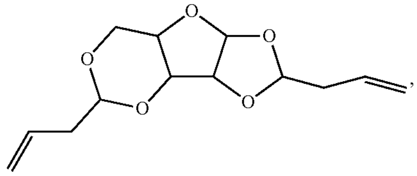
,
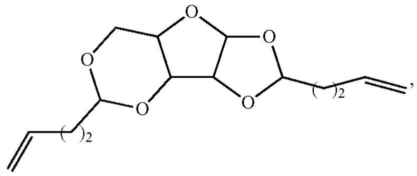
,
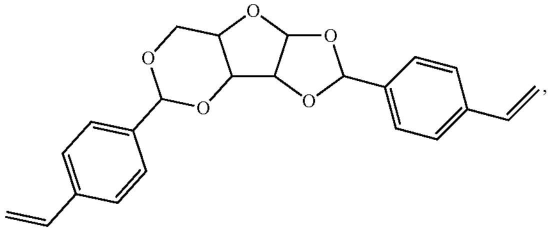
,
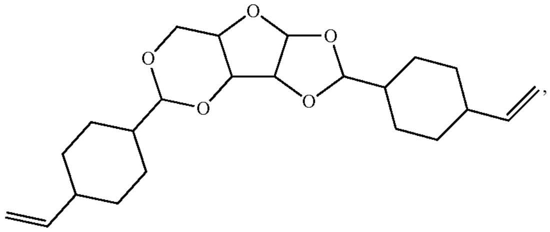
,
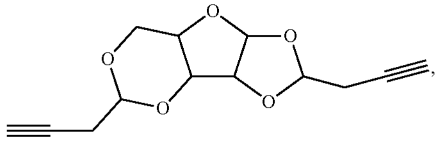
,
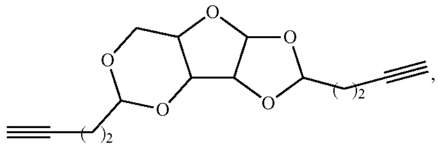
, -continued
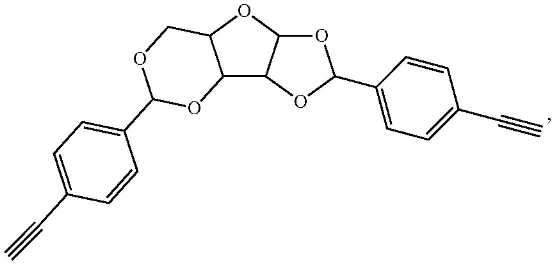
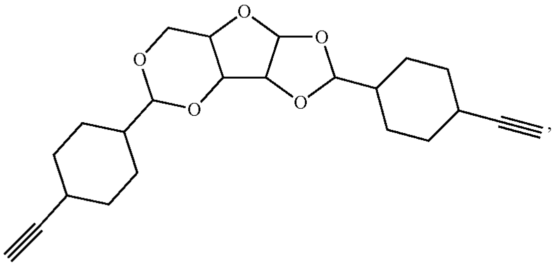
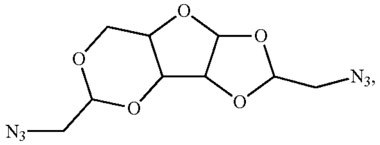
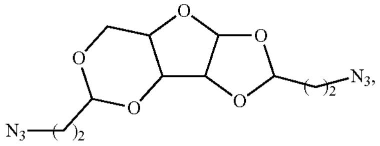
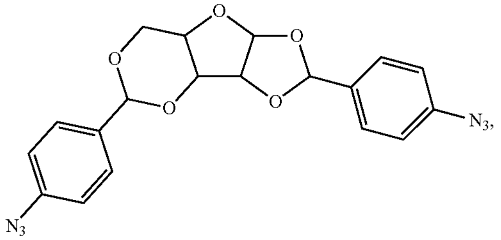
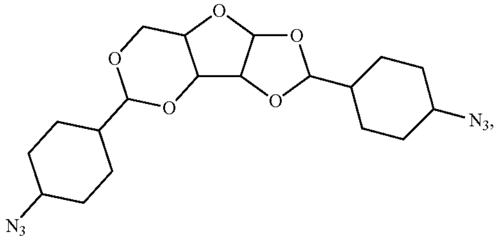
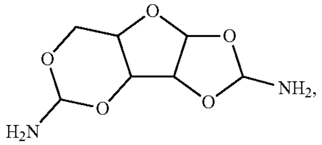
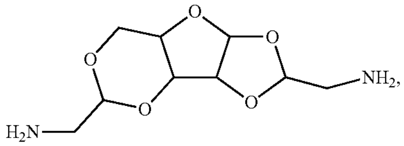
-continued
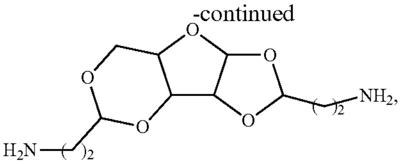
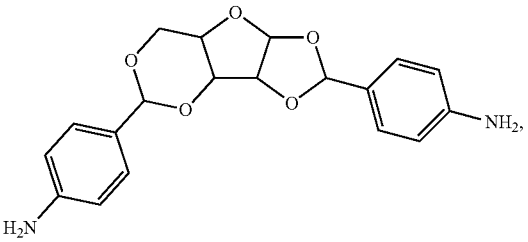 [SMILES: Nc1ccc(C2OCC3OC4OC(c5ccc(N)cc5)OC4C3O2)cc1]
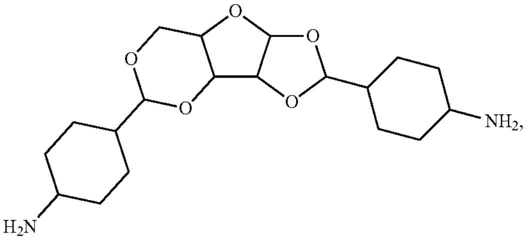
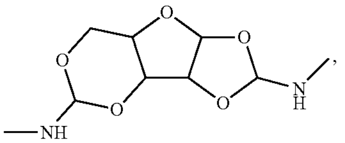
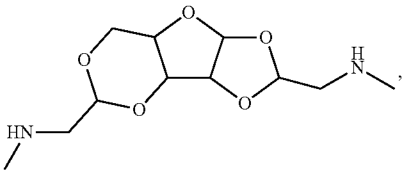
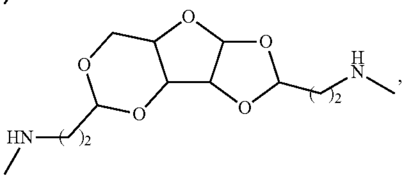
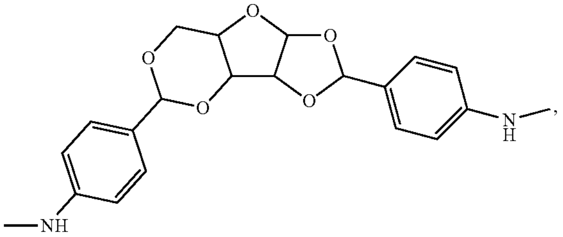
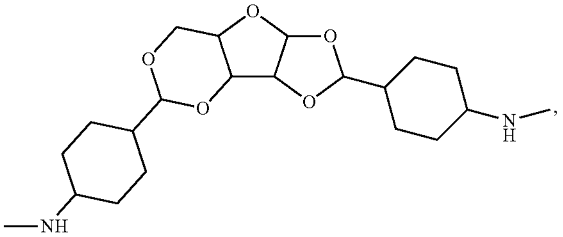
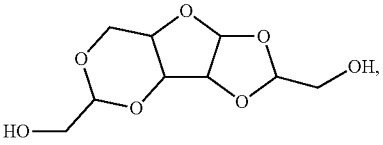

-continued
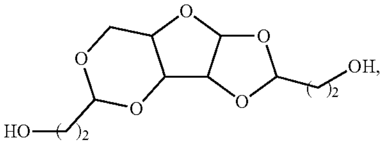
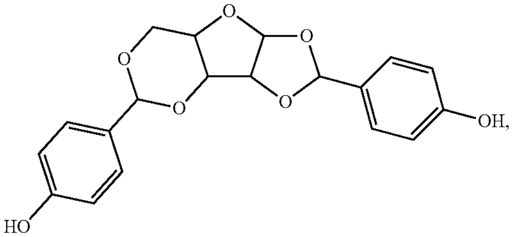
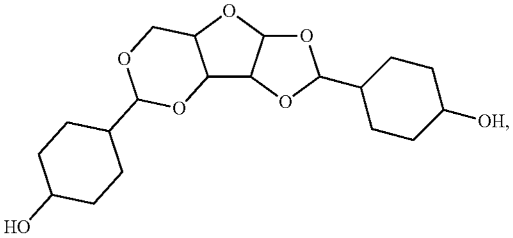
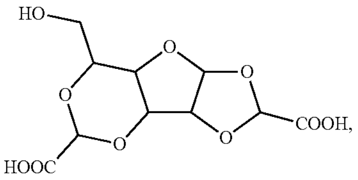
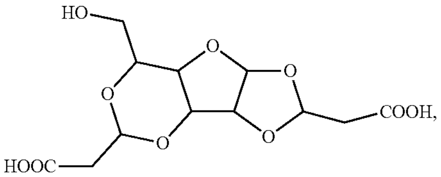
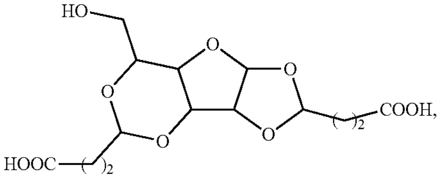
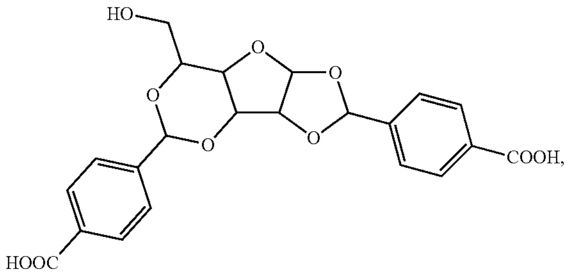
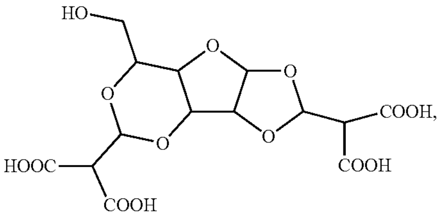
-continued
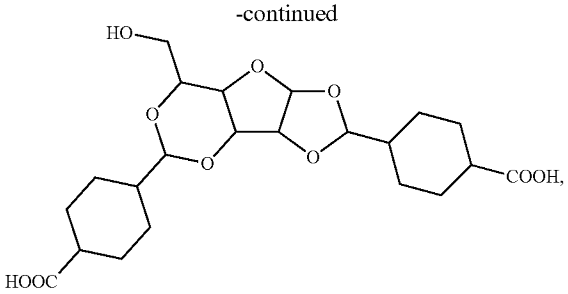
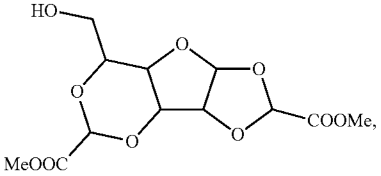
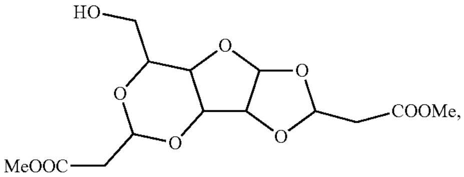
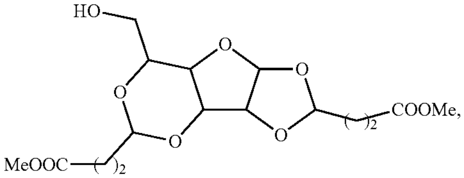
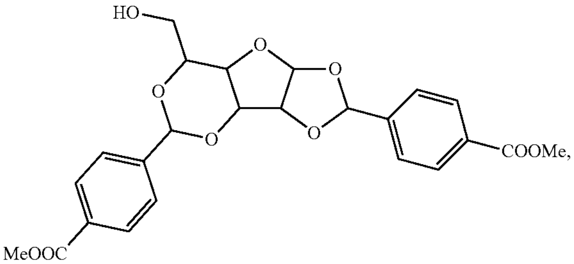
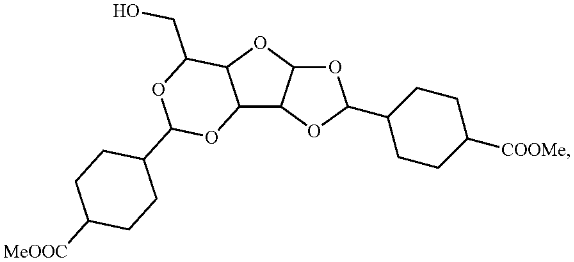
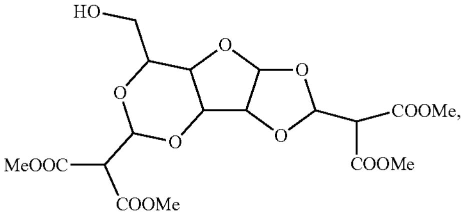
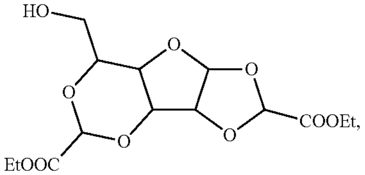

-continued
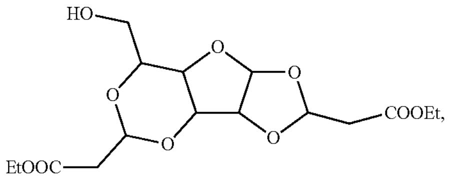
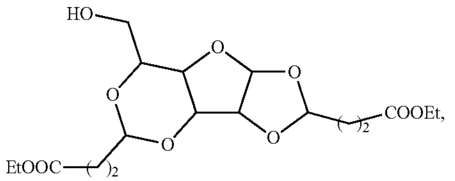
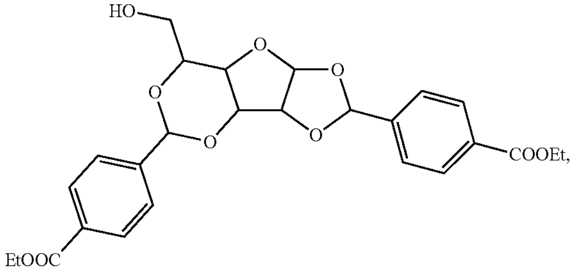
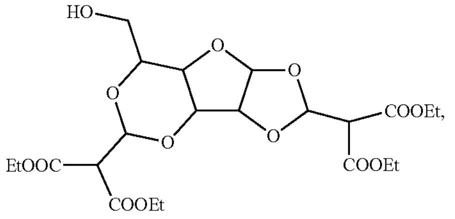
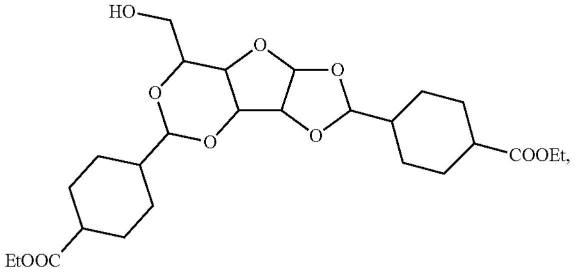
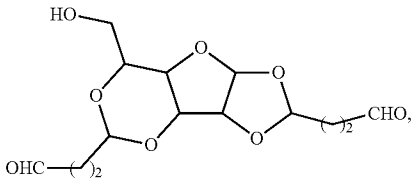
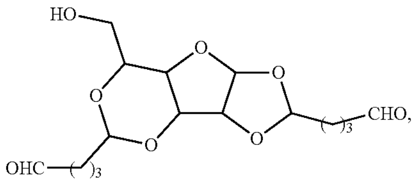
-continued
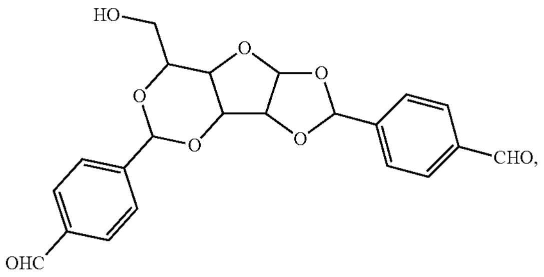
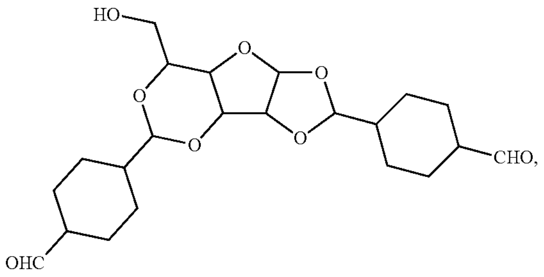
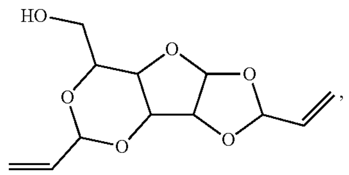
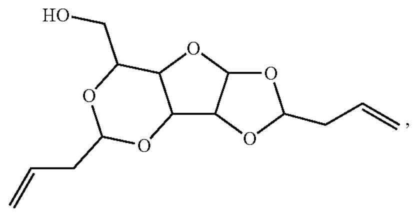
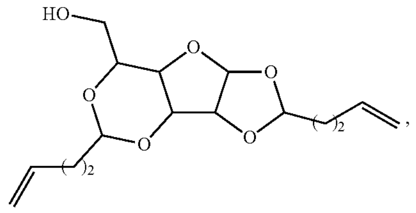
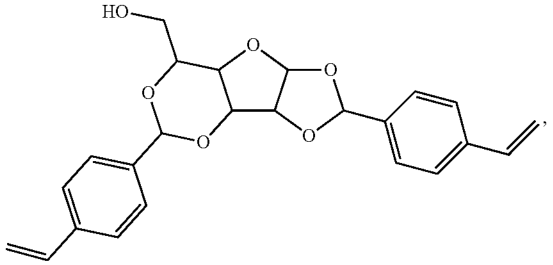
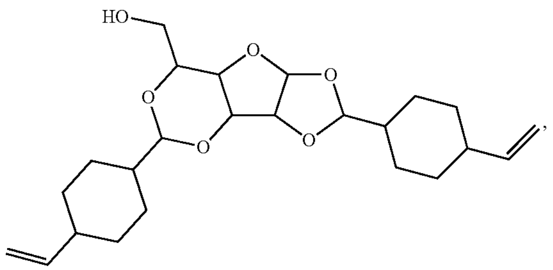

-continued
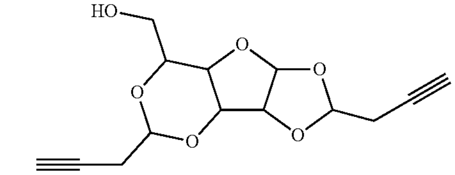
,
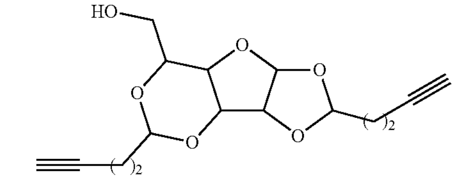
,
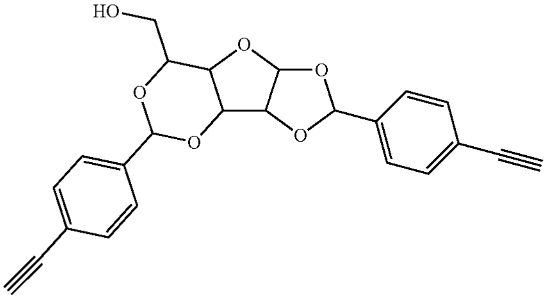
,
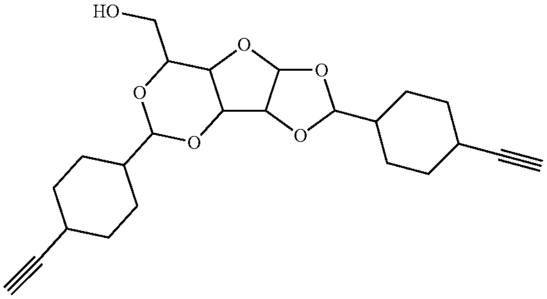
,
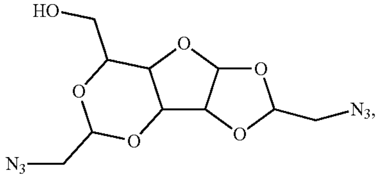
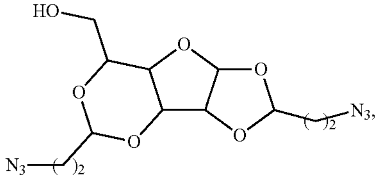
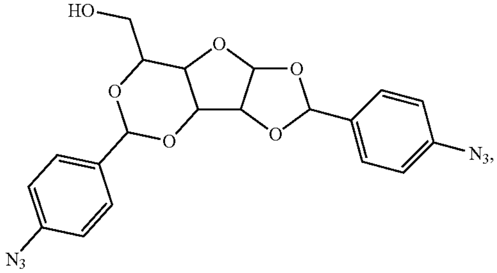
-continued
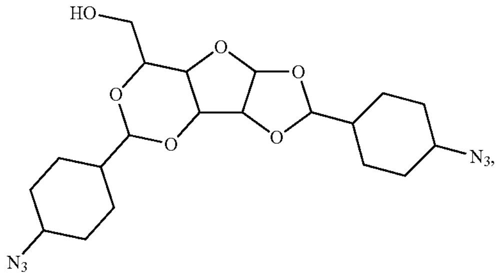
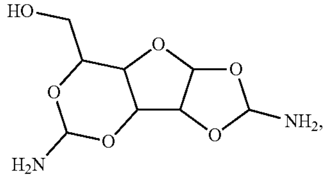
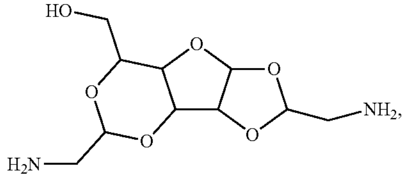
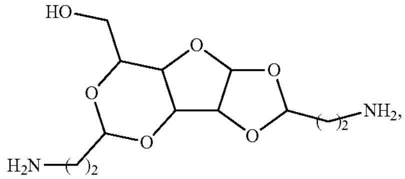
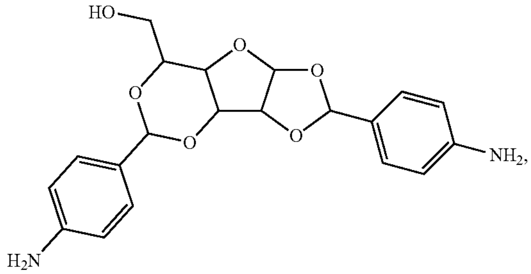
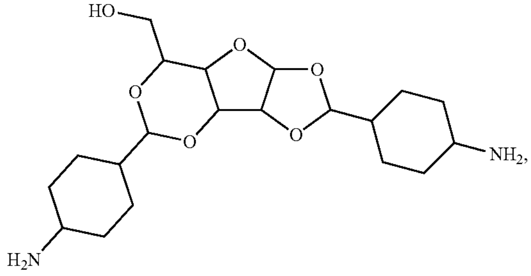 [SMILES: NC1CCC(C2OC3OC4C(CO)OC(C5CCC(N)CC5)OC4C3O2)CC1]
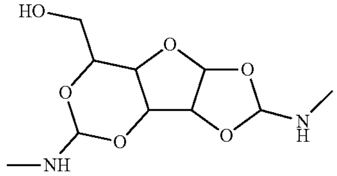
, -continued
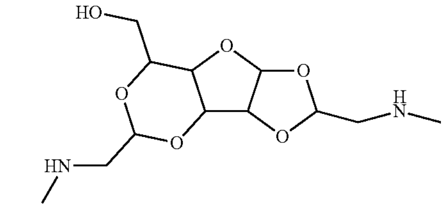
,
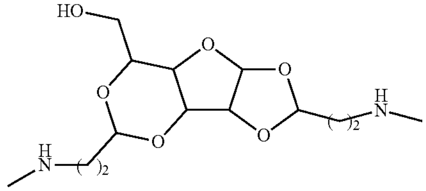
,
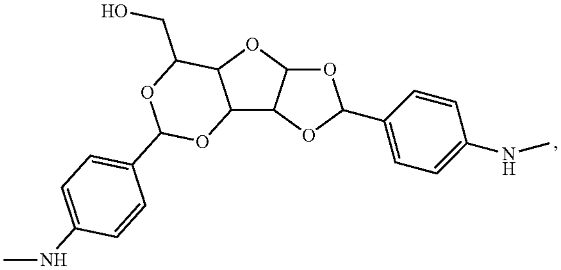
,
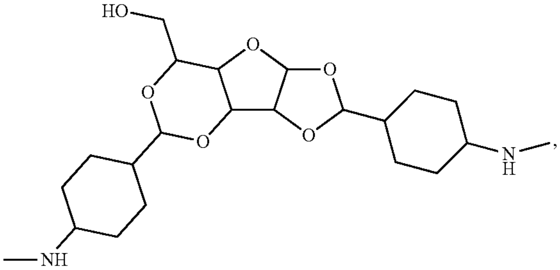
,
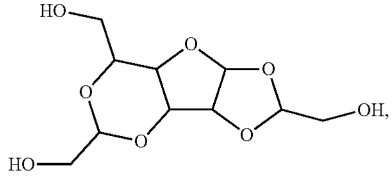
,
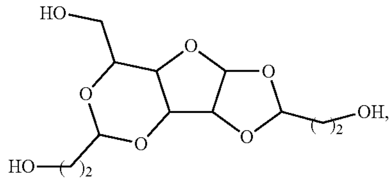
,
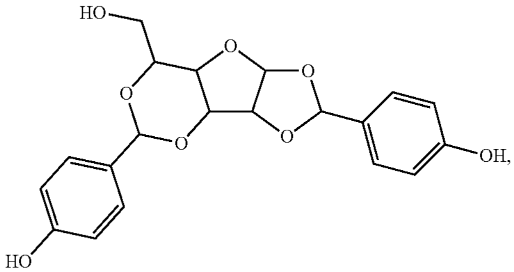
, or
-continued
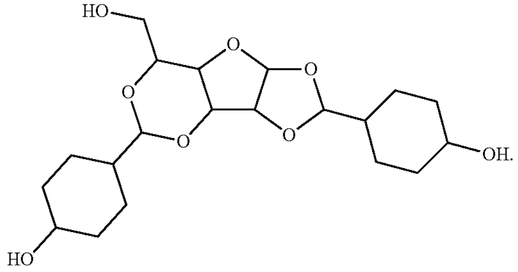
.
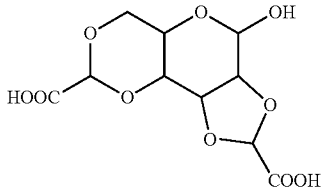
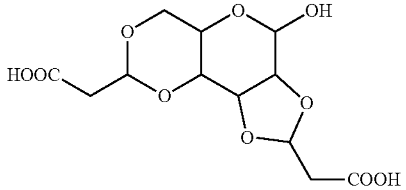
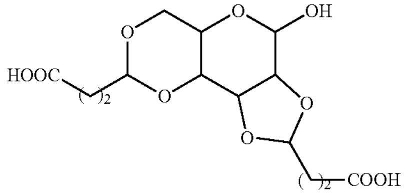
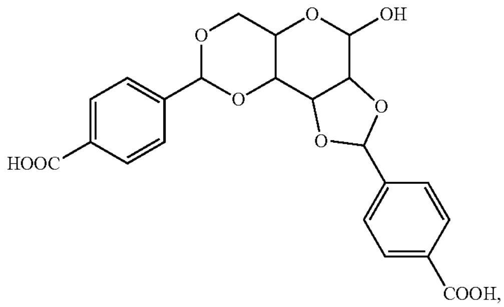
,
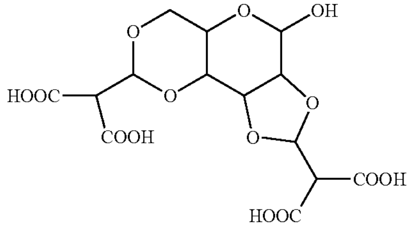
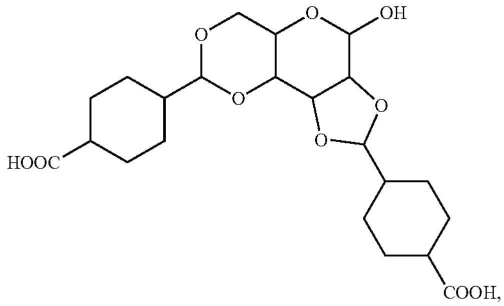
, -continued
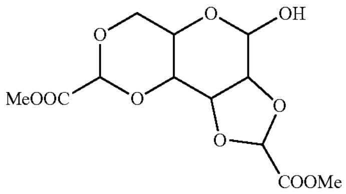
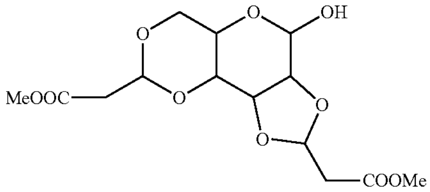
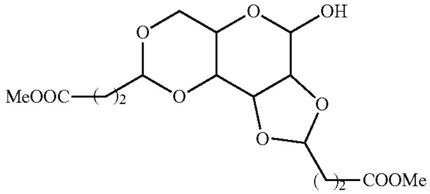
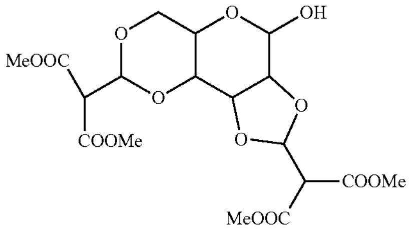
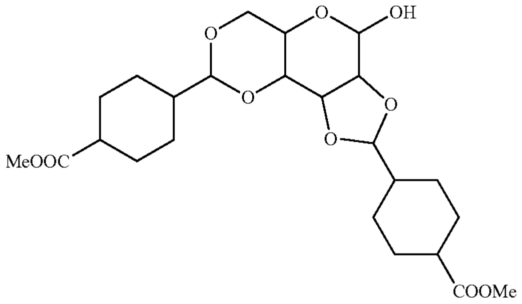
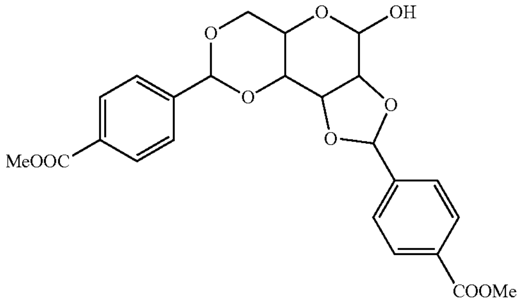
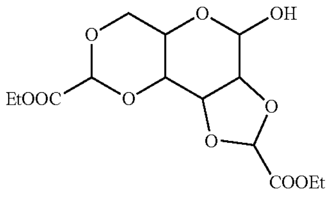
-continued
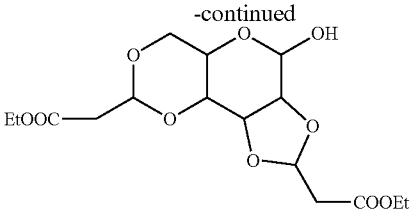
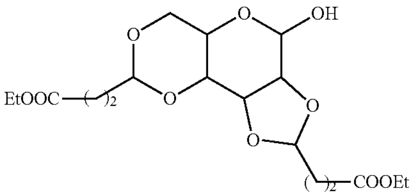
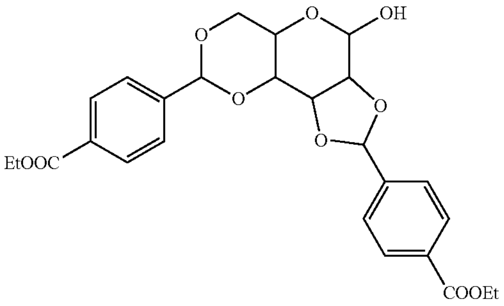
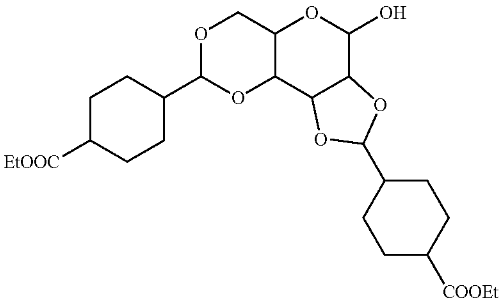
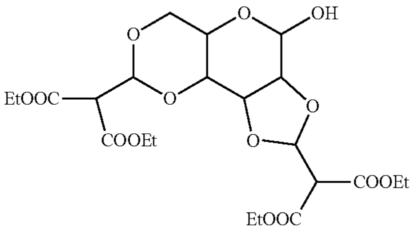
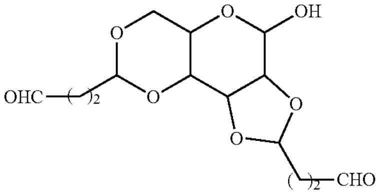
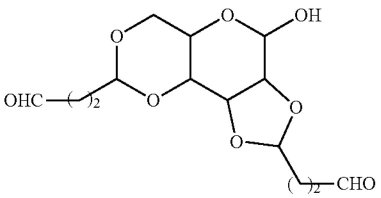

-continued
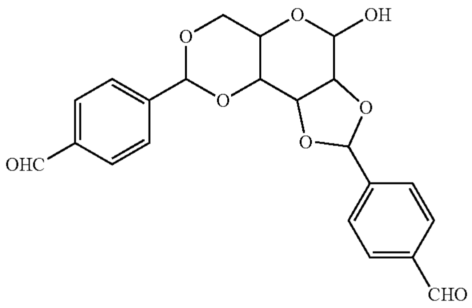
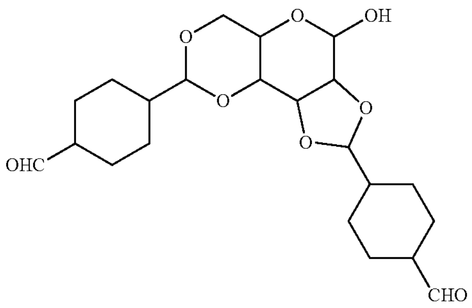
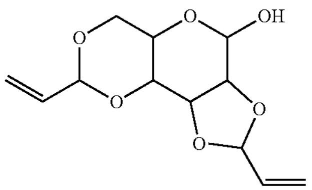
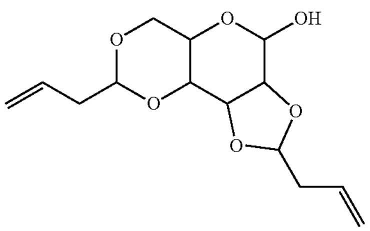
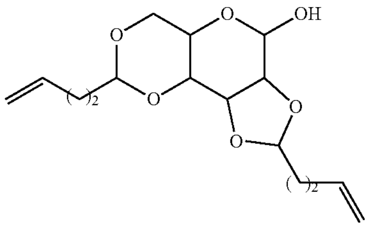
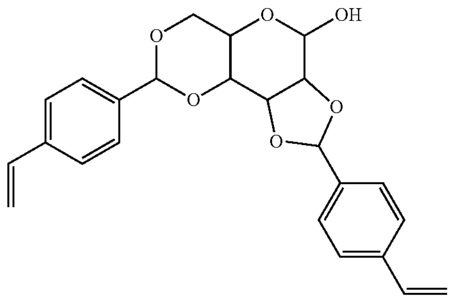
-continued
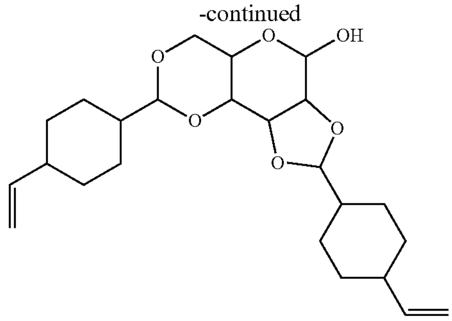
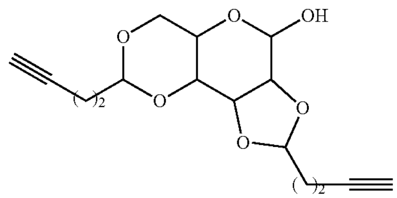
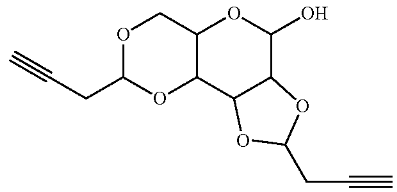
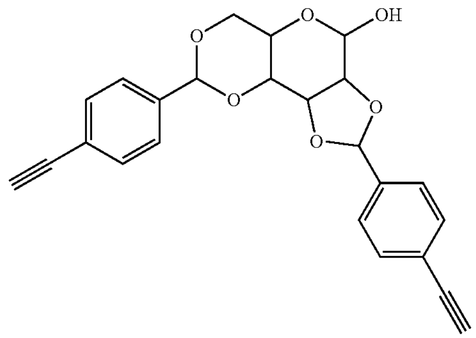
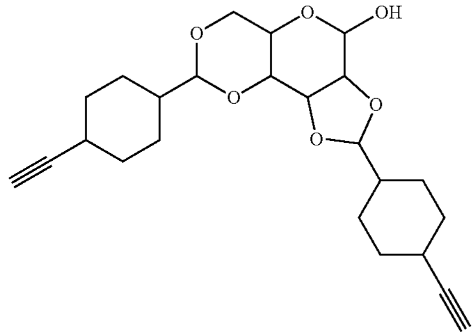
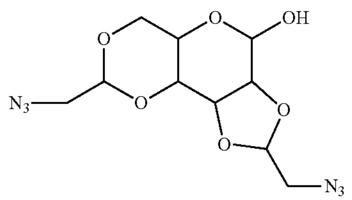

-continued
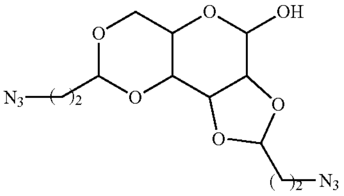
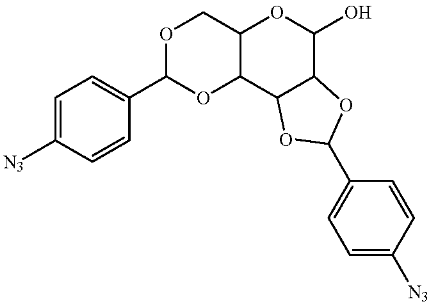
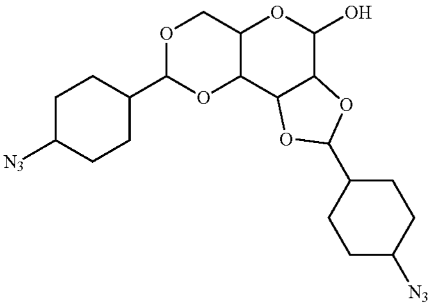
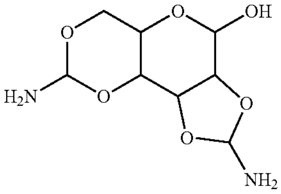
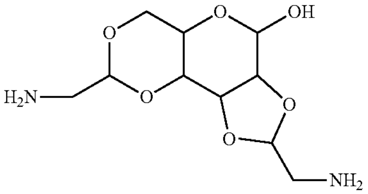
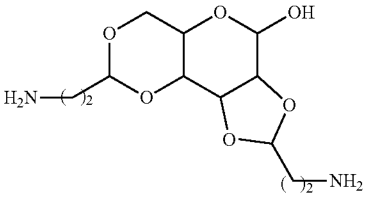
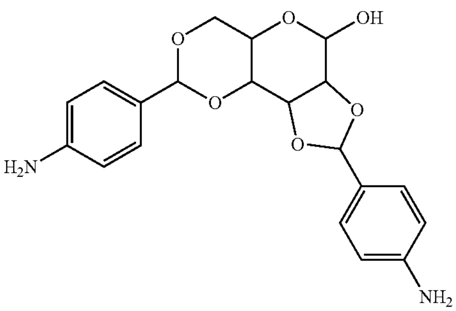
-continued
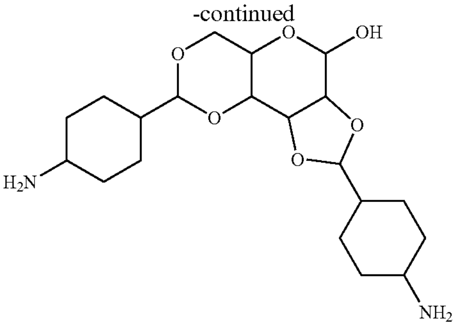
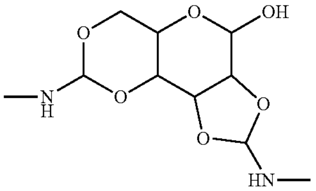
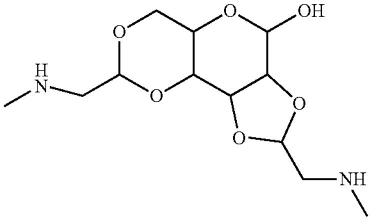
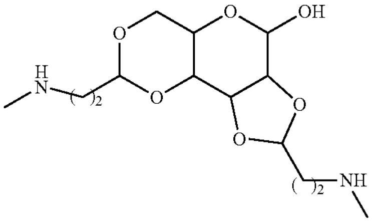
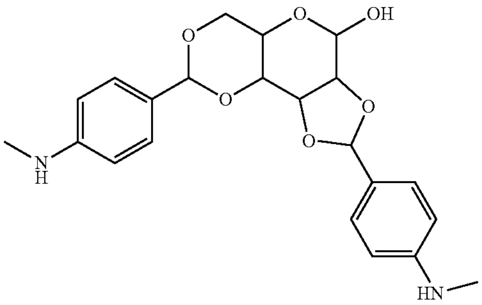
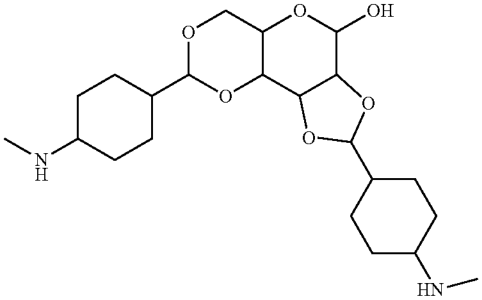
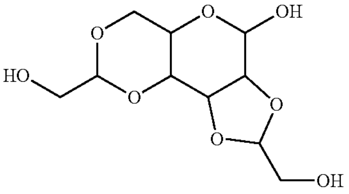

-continued
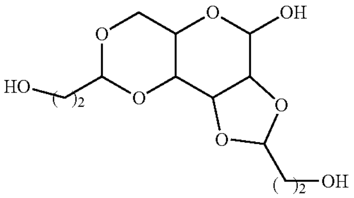
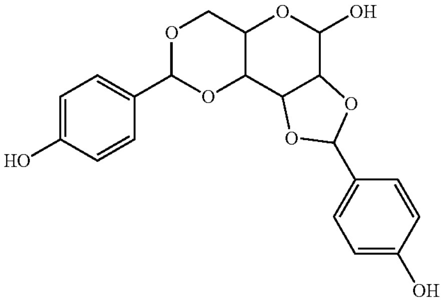
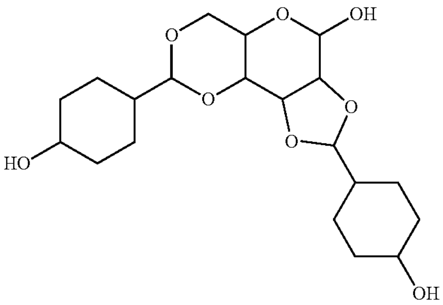
More preferably, the compound according to the invention has one of the following structures:
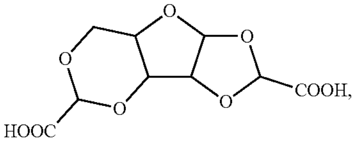
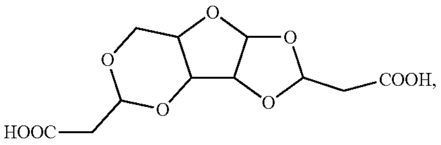
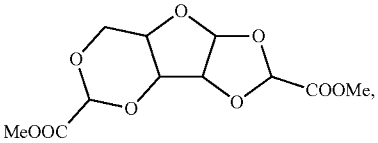
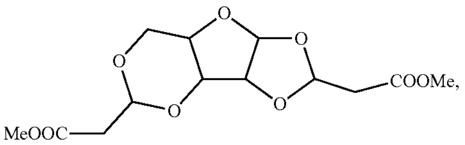
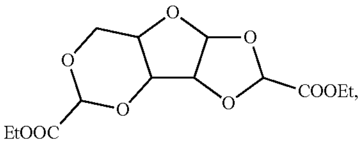
-continued
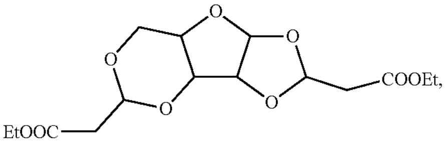
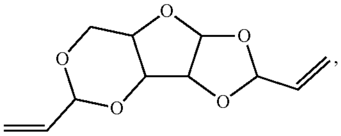
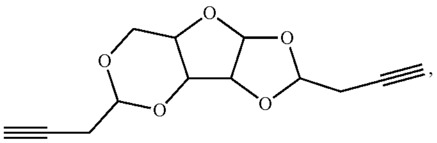
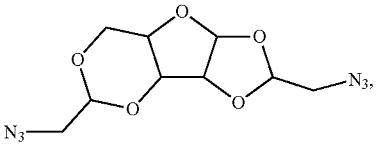
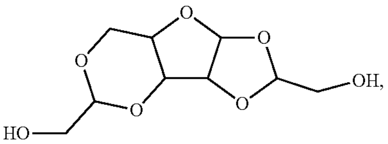
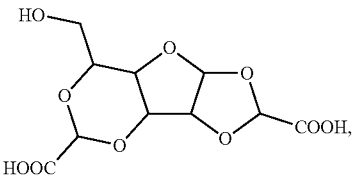
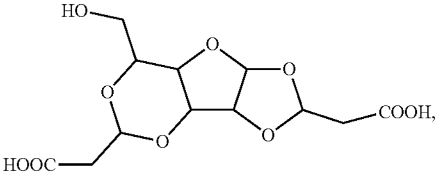
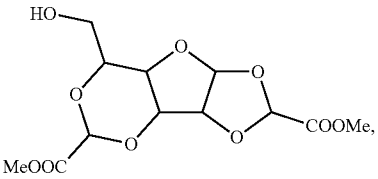
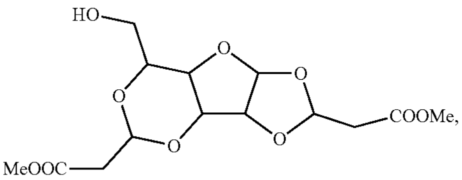
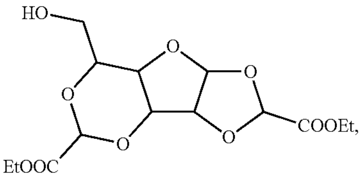

-continued
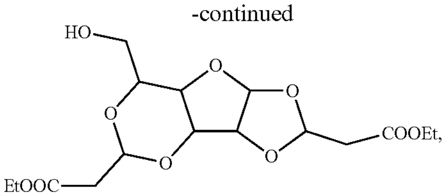
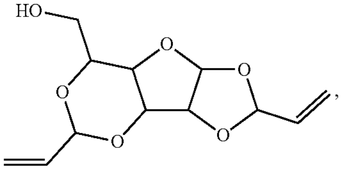
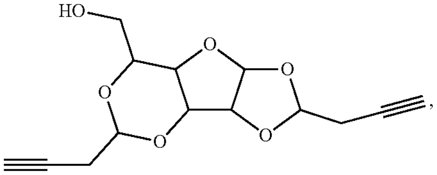
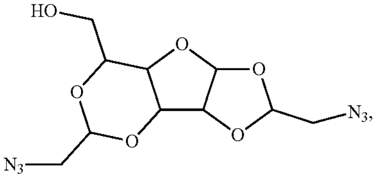
or
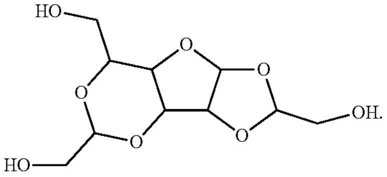
Still more preferably, the compound according to the invention has one of the following structures:
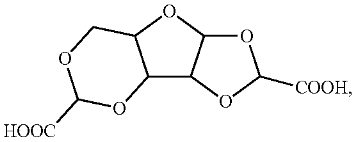
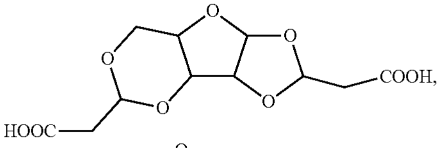
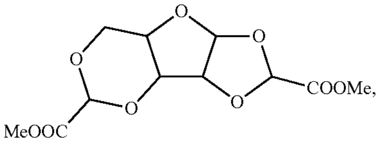
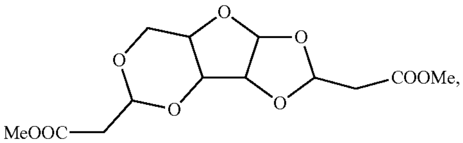
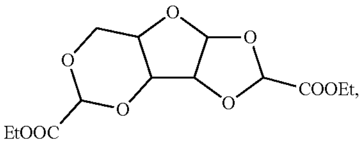
-continued
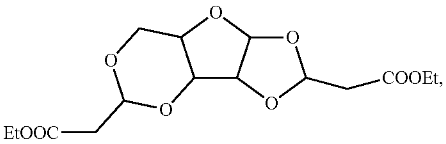
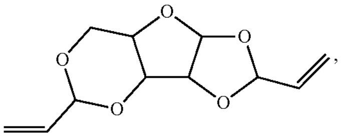
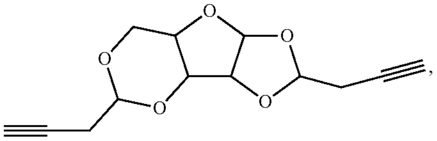
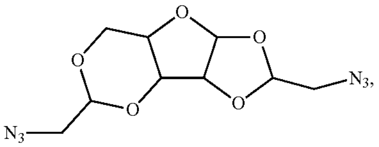
or
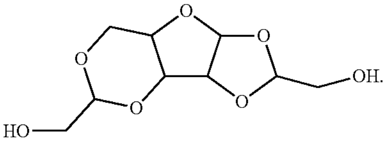
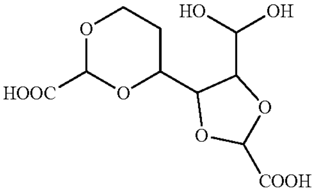
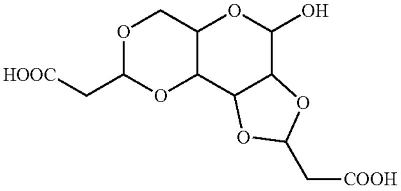
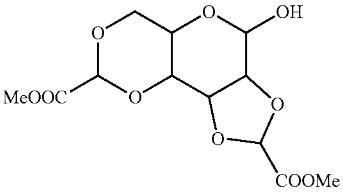
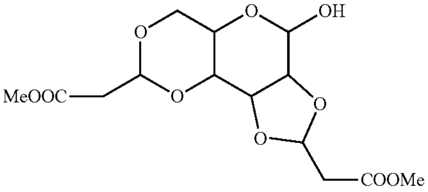
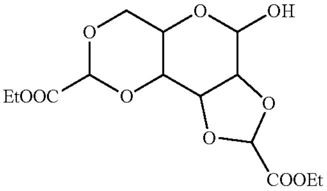

-continued

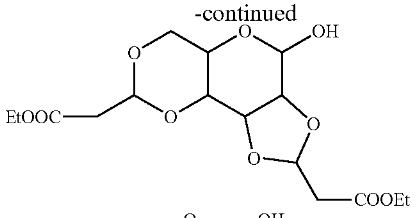

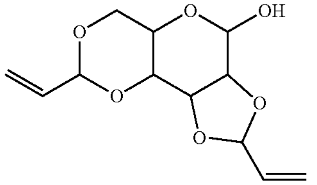

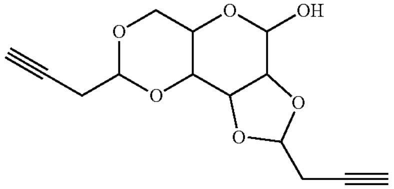

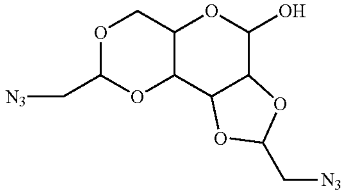

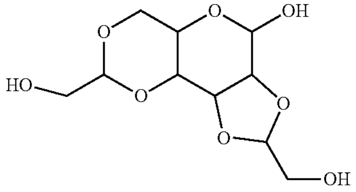

In the structures shown above, the ring systems preferably have the following stereochemistry:

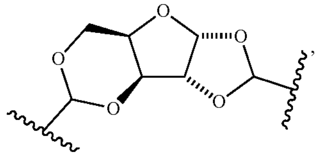

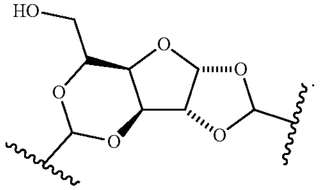

The Method for the Preparation of the Compound

The invention also provides for a method for the preparation of the compound according to the invention having the structure (I), (II) or (V). The method according to the invention comprises providing a carbohydrate and adding an aldehyde to the carbohydrate. If a mixture of carbohydrates is employed, a mixture of compounds having the structure (I), (II) or (V), in particular a mixture of compounds according to the invention having the structure (I), (II) or (V), may be obtained.

Thus, the invention provides for a method for the preparation of a compound according to the invention or a composition comprising at least two different compounds according to the invention, having one of the structures (I), (II) or (V), (I)

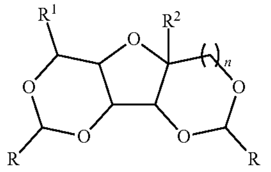

or (II)

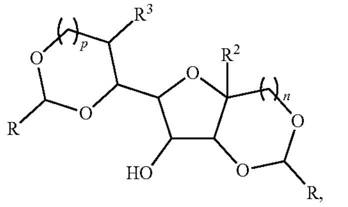

or (V)

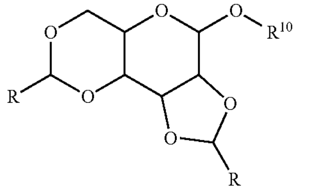

wherein

R, $R^1$, $R^2$, $R^3$, $R^{10}$, n, and p are as defined herein, comprising the steps of a. providing a carbohydrate or a lignocellulose-containing composition;

b. adding an aldehyde optionally comprising at least one functional group selected from the group consisting of carboxylic acid, carboxylic amide, ether, alkyne, alkene, aldehyde, chloride, hydroxyl, azide, carboxylic acid ester, aldehyde, vinyl, and amine to the carbohydrate or to the lignocellulose-containing composition to obtain a mixture;

c. heating the mixture under acidic conditions; and d. separating, in particular isolating, the compound according to the invention or the composition comprising at least two different compounds according to the invention, having one of the structures (I), (II) or (V)

(I)

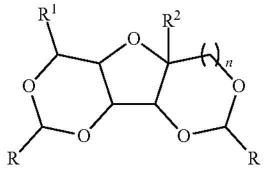

or

-continued (II)

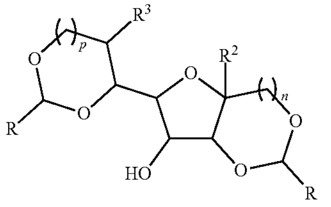

or (V)

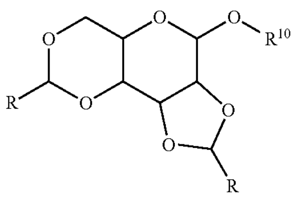

wherein R, $R^1$, $R^2$, $R^3$, $R^{10}$, n, and p are as defined herein.

In a preferred embodiment of the invention good results have been obtained when the aldehyde of step b) is selected from a group consisting of acetaldehyde, propionaldehyde, isobutyraldehyde, glyoxylic acid, dialdehyde, cyclopropanecarboxaldehyde, isobutyraldehyde, pivaldehyde, tolualdehyde, and benzaldehyde.

Different carbohydrates can be employed as carbohydrates in the method for the preparation of the compound according to the invention. The carbohydrate may be an aldose or a ketose. The carbohydrate may be a pentose, a hexose, or a heptose. Preferably, the carbohydrate is an aldopentose, an aldohexose, an aldoheptose, a ketohexose, a ketoheptose or a mixture thereof. More preferably, the carbohydrate is an aldopentose, an aldohexose, an aldoheptose, or a mixture thereof, in particular an aldopentose, an aldohexose, or a mixture thereof.

Advantageously, the carbohydrate is selected from the group consisting of ribose, arabinose, xylose, lyxose, allose, altrose, glucose, mannose, gulose, idose, galactose, talose, glucoheptose, mannoheptose, psicose, fructose, sorbose, tagatose, sedoheptulose, mannoheptulose, taloheptulose, alloheptulose, and mixtures thereof. Preferably, the carbohydrate is selected from the group consisting of ribose, arabinose, xylose, lyxose, allose, altrose, glucose, mannose, gulose, idose, galactose, glucoheptose, mannoheptose, or mixtures thereof, more preferably selected from the group consisting of ribose, arabinose, xylose, lyxose, allose, altrose, glucose, mannose, gulose, idose, galactose, or mixtures thereof. Most preferably, the carbohydrate is xylose, glucose, or a mixture thereof.

In the method for the preparation of the compound according to the invention, a lignocellulose-containing composition may be employed.

Lignocellulose is considered to be the most abundantly available raw material (biomass) on earth. Lignocellulosic biomass can be classified into virgin biomass, waste biomass and energy crops. Virgin lignocellulosic biomass includes all naturally occurring terrestrial plants such as trees, bushes and grass. Waste lignocellulosic biomass is produced as a low valuable byproduct of various industrial sectors, such as agriculture (corn stover, sugarcane bagasse, straw etc.) and forestry (sawmill and paper mill discards).

Lignocellulose comprises hemicellulose, cellulose and lignin. Hemicellulose and cellulose can both be regarded as carbohydrate polymers. The carbohydrate polymers contain five and six carbon sugar monomers and are bound to lignin.

Lignin can be regarded as an aromatic polymer. Said aromatic polymer contains methoxylated phenyl-propane subunits such as guaiacyl and syringyl subunits.

Xylan is a polysaccharide which belongs to the hemicelluloses, wherein the main monomer unit of xylan is D-xylose. Cellulose can be regarded as a polysaccharide, wherein the main monomer unit is D-glucose which is linked via β-1-4 bindings.

Preferably, the lignocellulose-containing composition is biomass, in particular, lignocellulosic biomass, preferably virgin lignocellulosic biomass, for example wood. The lignocellulosic biomass is preferably derived from trees, such as birch, beech, poplar, cedars, Douglas firs, cypresses, firs, junipers, kauri, larches, pines, hemlocks, redwoods, spruces, and yews. The most preferred wood is hardwood such as oak, poplar, maple, eucalyptus, birch and/or beach as lignocellulose-containing composition.

The lignocellulose-containing composition may also be derived from energy crops. Energy crops are crops with high yields of lignocellulosic biomass. In addition, energy crops are fast growing such that the lignocellulosic biomass is available already within a short period of time for example after a couple of months. Examples of energy crops include giant reed, big bluestem, Chinese tallow, camelina, duckweed, purging nut, millettia pinnata, switchgrass, and elephant grass.

According to an embodiment, the lignocellulose-containing composition is derived from corn cobbs.

It is preferred that the lignocellulose-containing composition is solid at a temperature of 23° C. Preferably, the lignocellulose-containing composition is air dried at temperatures 60° C. For example, the lignocellulose-containing composition is air dried for storage to remove excessive water. The air-dried lignocellulose-containing composition preferably comprises less than 50 wt. %, more preferably less than 30 wt. %, and in particular from 0 to 10 wt. % water.

The lignocellulose-containing composition may have a lignin content of 1 to 50 wt. %, preferably 10 to 30 wt. %, based on the total weight of the lignocellulose-containing composition. The lignin is preferably determined as Klason lignin.

For the determination of Klason lignin, the Klason lignin test is applied. In this test, wood particles (0.25 to 0.50 g) are loaded into 50 mL beaker with the addition of 7.5 mL of a 72 wt. % sulfuric acid solution. The mixture is left at room temperature for 2 hours and stirred with a glass rod every 10 minutes. Afterwards the slurry is transferred into a round bottom flask and 290 mL of water are added to reach a sulfuric acid concentration of 3 wt. %. The glass bottle is sealed with the screw cap and sterilized at 120° C. for 1 hour in an autoclave. The resulting solution is filtered, and the precipitate is washed with water, dried at 105° C., and weighed to determine the Klason lignin content.

The content of Klason lignin can be determined by the following equation:

Content of Klason lignin [%]=KL/LCC×100%, wherein

KL is the amount of Klason lignin in g, LCC is the amount of lignocellulose-containing composition in g.

Different aldehydes may be used in the method for the preparation of a compound according to the invention. Preferably, the aldehyde has the formula R—CHO, wherein R is as defined herein. More preferably, the aldehyde has the formula $CHO—(CH_2)_mCOOH$; $CHO—C_6H_4COOH$, wherein the aromatic ring is optionally substituted with 1 to 4 $C_1$-$C_4$-alkyl groups; CHO—$C_6H_{10}$COOH, wherein the aliphatic ring is optionally substituted with 1 to 4 $C_1$-$C_4$-alkyl groups; or CHO—$(CH_2)_m$CH$(COOH)_2$.

The lignocellulose-containing composition may be mixed with a solvent for example ethereal solvent such as dioxane, 2-methyltetrahydrofuran, 3-methyltetrahydrofuran, tetrahydrofuran, or γ-valerolactone, glyme, or diglyme.

To produce the monomers, the mixture containing the substrate (sugars or lignocellulose) and aldehyde may be heated at various temperatures in step c. Advantageously, the mixture is heated at 50 to 120° C., preferably at 60 to 110° C., more preferably at 60 to 100° C., most preferably at 60 to 85° C. It was found that at temperature below 50° C., the reaction proceeds very slowly. At all temperatures, the reaction can be accelerated by the presence of an acid catalyst. At temperatures above 120° C., it was found that undesired by-products are formed.

Heating of the mixture may also be conducted under various pressures depending on the feedstock. For carbohydrates, the heating is advantageously conducted at a pressure below 150 mbar. In particular, the reaction may be conducted at a pressure of 70 to 130 mbar, preferably at 80 to 120 mbar, more preferably at 90 to 110 mbar. It was found that the reaction proceeds faster at reduced pressures.

For carbohydrates, very good results are obtained, when the mixture is heated at 50 to 120° C., preferably at 60 to 110° C., more preferably at 60 to 100° C., most preferably at 60 to 85° C. and at a pressure of 70 to 130 mbar, preferably at 80 to 120 mbar, more preferably at 90 to 110 mbar. Under these conditions, water produced in the course of the reaction can be removed from the reaction which aids in obtaining high yields of the desired products and also aids in accelerating the reaction.

According to an embodiment, for biomass, steps a. to c. are advantageously conducted in a solvent that is preferably a polar aprotic solvent, and even more preferably ethereal, most preferably dioxane, γ-valerolactone, 2-methyltetrahydrofuran, 3-methyltetrahydrofuran, or tetrahydrofuran. According to this embodiment, steps a. to c. are preferably conducted for 0.5 to 72 hours, more preferably 1 to 24 hours, and most preferably 2 to 4 hours. According to this embodiment, steps a. to c. are advantageously conducted at temperatures of 50 to 120° C., preferably at 60 to 110° C., more preferably at 60 to 100° C., and most preferably at 60 to 85° C. The cellulose is then preferably removed by filtration from the reaction mixture. Also the solvent is then preferably removed by evaporation at reduced pressure such as 1 mbar to 150 mbar from the reaction mixture. The lignin is then preferably removed by precipitation in a solvent followed by filtration of the precipitation mixture yielding a filtrate solution. The resulting filtrate solution is then preferably concentrated and an acid is added followed by heating and reducing the pressure as described for the carbohydrates above.

Acidic conditions of the mixture may be effected by various means. Advantageously, an acid is added to the mixture. Different acids can be used for this purpose. Examples of suitable acids are sulfuric acid, hydrochloric acid, hydrobromic acid, hydroiodic acid, perchloric acid, phosphoric acid, nitric acid, formic acid, acetic acid, trifluoroacetic acid, methanesulfonic acid, and toluenesulfonic acid. The acids are preferably used at a concentration of 0.1 to 1 M, more preferably 0.2 to 0.6 M. Preferably, sulfuric acid is added to the mixture. An acidic aldehyde such as, but not limited to glyoxylic acid can self-catalyze the reaction.

The method for the preparation of the compound according to the invention may comprise additional steps. Advantageously, the method according to the invention comprises the step of adding an alcohol. In particular, an alcohol may be added if the aldehyde comprises a carboxylic acid group, more particularly if the aldehyde has the formula CHO—$(CH_2)_m$COOH; CHO—$C_6H_4$COOH, wherein the aromatic ring is optionally substituted with 1 to 4 $C_1$-$C_4$-alkyl groups; CHO—$C_6H_{10}$COOH, wherein the aliphatic ring is optionally substituted with 1 to 4 $C_1$-$C_4$-alkyl groups; or CHO—$(CH_2)_m$CH$(COOH)_2$, wherein m is an integer from 0 to 10, preferably from 0 to 4. The alcohol is preferably added after the mixture is heated under acidic conditions. Preferably, the alcohol is a $C_1$-$C_4$-alkylalcohol, more preferably methanol.

Advantageously, the aldehyde has the formula CHO—$(CH_2)_m$COOH; CHO—$C_6H_4$COOH, wherein the aromatic ring is optionally substituted with 1 to 4 $C_1$-$C_4$-alkyl groups; CHO—$C_6H_{10}$COOH, wherein the aliphatic ring is optionally substituted with 1 to 4 $C_1$-$C_4$-alkyl groups; or CHO—$(CH_2)_m$CH$(COOH)_2$, wherein m is an integer from 0 to 10, preferably from 0 to 4, and wherein the method comprises the additional step of adding a $C_1$-$C_4$-alkylalcohol, preferably methanol, after step c. and before step d.

The alcohol such as the $C_1$-$C_4$-alkylalcohol, preferably methanol, may be added to the mixture at a ratio of 1:1 volume of alcohol to mass of reaction mixture to 20:1 volume of alcohol to mass of reaction mixture, preferably 5:1 volume of alcohol to mass of reaction mixture to 15:1 volume of alcohol to mass of reaction mixture, more preferably 10:1 volume of alcohol to mass of reaction mixture.

The mixture containing the $C_1$-$C_4$-alkylalcohol, preferably methanol, may then be heated, preferably to the boiling temperature of the mixture. The heating may be continued for 1 to 10 hours, preferably for 2 to 5 hours, more preferably for 2 to 4 hours.

Step d. may comprise a neutralization step. Neutralization is preferably conducted using a weak base. Examples for suitable weak bases are bicarbonates such as sodium bicarbonate or potassium bicarbonate, preferably as aqueous solutions.

Separating, in particular isolating, of the compound according to the invention or the composition comprising at least two different compounds according to the invention may comprise several steps. Separating may comprise dissolving the compound or the compounds according to the invention with an organic solvent. Separating may also comprise one or more filtration and/or drying steps, preferably before dissolving the compound or the compounds according to the invention in an organic solvent. Examples for suitable organic solvents are diethyl ether, tetrahydrofuran, ethyl acetate, glyme, diglyme, dichloromethane, chloroform and tetrachloromethane, in particular diethyl ether, tetrahydrofuran, ethyl acetate, and dichloromethane, more particularly ethyl acetate or dichloromethane. Separating may also comprise one or more washing steps, for example with aqueous solutions such as aqueous sodium bicarbonate solution and/or aqueous sodium chloride solution. Separating may also comprise a purification step, for example distilling. Distilling is preferably conducted as the last purification step. Alternatively, crystallization can be carried out as a final purification step before polymerization. For example, for dimethylglyoxylate xylose, cyclopentylmethyl ether, toluene, or alcohols can be used for crystallization. By carrying out a temperature-controlled crystallization it is even possible to obtain chiral resolution of the isomers.

The Polymer According to the Invention

The compounds according to the invention can be used for the preparation of polymers. For example, the compounds according to the invention can be used as monomers for the preparation of polyesters or polyamides.

Accordingly, the invention also provides for a polymer comprising as repeat unit (III)

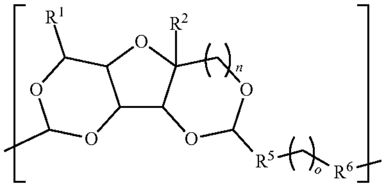

and/or (IV)

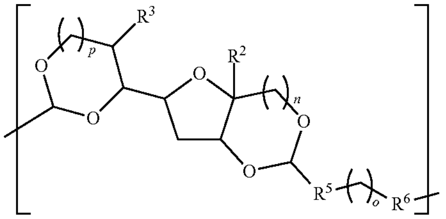

and/or (VI)

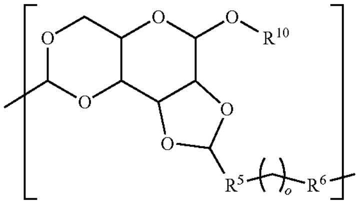

wherein $R^1$, $R^2$, $R^3$, $R^{10}$, n, and p are as defined herein; and $R^5$ is —Z—$F^1$— and $R^6$ is —$F^2$—Z—, wherein Z is a hydrocarbon moiety with 0 to 10 carbon atoms, optionally substituted with 1 to 4 $C_1$-$C_4$-alkyl groups or 1 to 4 halogen atoms, and wherein $F^1$ is —C(═O)O—, —OC(═O)—, —C(═O)$NR^8$—, —$R^8$NC(═O)—, or a covalent bond, and $F^2$ is —OC(═O)—, —C(═O)O—, —$R^8$NC(═O)—, —C(═O)$NR^8$—, or a covalent bond;

wherein $R^8$ is H or a $C_1$-$C_4$-alkyl group; and o is an integer from 2 to 10, in particular from 2 to 4.

The residues $R^1$, $R^2$, and $R^3$ differ depending on the type of carbohydrate from which the monomers used in the preparation of the polymer according to the invention have been obtained. If the monomers have been obtained from aldoses, $R^1$ may be —H, —$CH_2OH$ or —CH(OH)$CH_2OH$, $R^2$ may be —H, and $R^3$ may be —H, —OH, or —$CH_2OH$. If the monomers have been obtained from ketoses, $R^1$ may be —H or —$CH_2OH$, $R^2$ may be —OH or —$CH_2OH$, and $R^3$ may be —H.

Accordingly, the polymer according to the invention preferably comprises as repeat unit at least one of the following structures:

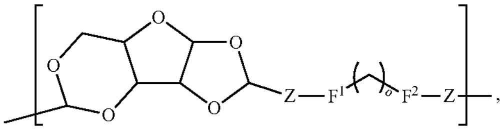

,

-continued

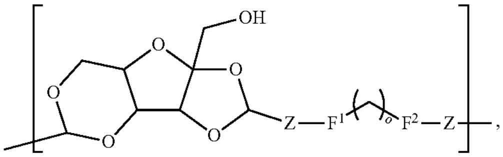

,

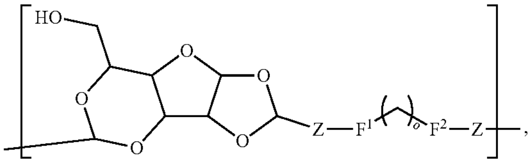

,

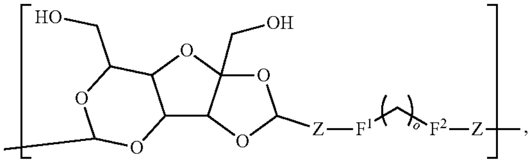

,

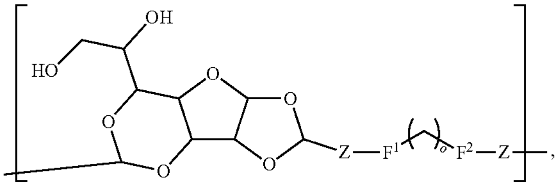

,

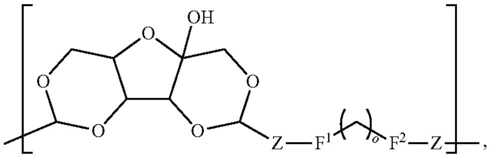

,

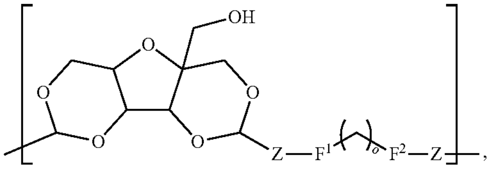

,

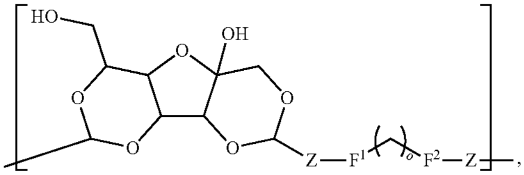

,

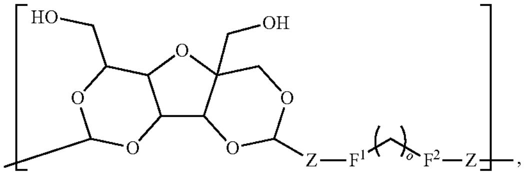

,

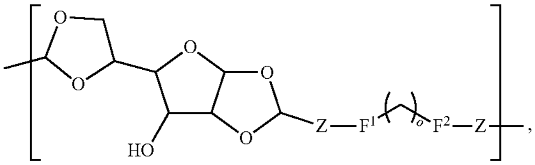

,

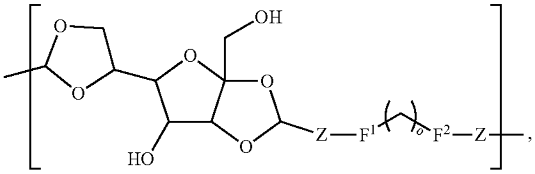

,

-continued

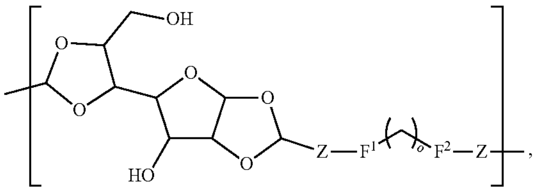

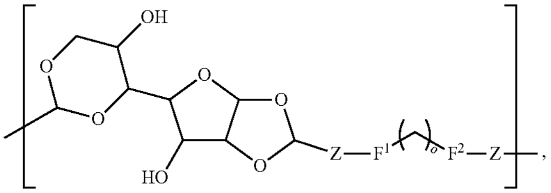

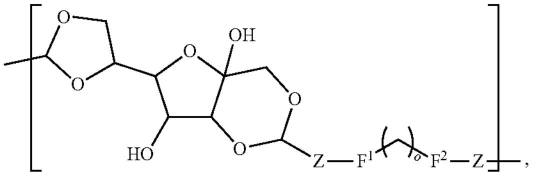

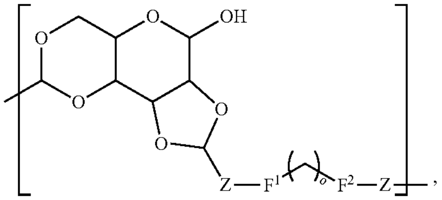

or

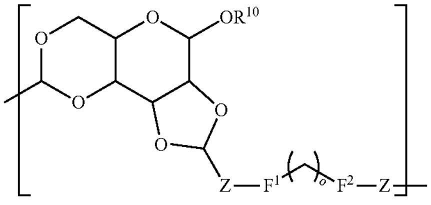

wherein Z is a hydrocarbon moiety with 0 to 10 carbon atoms, optionally substituted with 1 to 4 $C_1$-$C_4$-alkyl groups or 1 to 4 halogen atoms, and wherein $F^1$ is —C(═O)O—, —OC(═O)—, —C(═O)$NR^8$—, —$R^8$NC(═O)—, or a covalent bond, and $F^2$ is —OC(═O)—, —C(═O)O—, —$R^8$NC(═O)—, —C(═O)$NR^8$—, or a covalent bond;

wherein $R^8$ is H or a $C_1$-$C_4$-alkyl group;

$R^{10}$ is hydrogen or a hydrocarbon moiety with 1 to 20 carbon atoms, wherein each hydrogen atom of the hydrocarbon moiety may optionally be substituted with a $C_1$-$C_4$-alkyl group or a halogen atom; and o is an integer from 2 to 10, in particular from 2 to 4.

More preferably, the polymer according to the invention comprises as repeat unit at least one of the following structures:

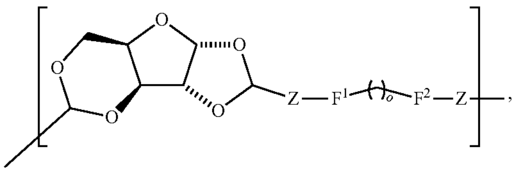

-continued

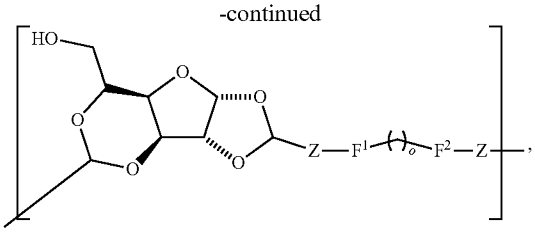

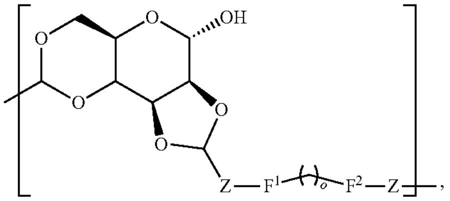

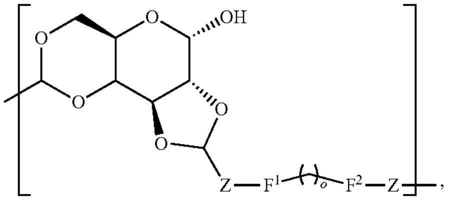

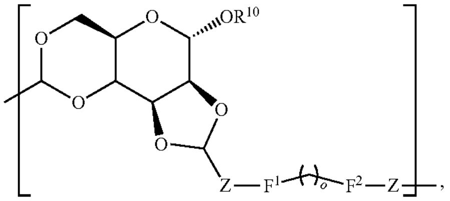

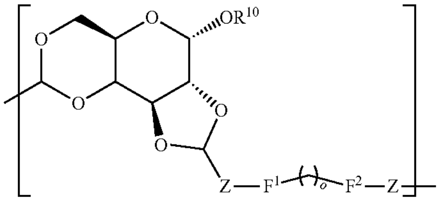

in particular

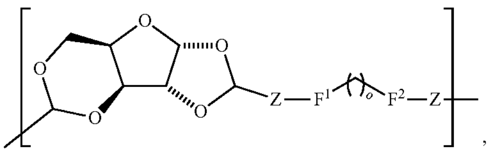

wherein Z is a hydrocarbon moiety with 0 to 10 carbon atoms, optionally substituted with 1 to 4 $C_1$-$C_4$-alkyl groups or 1 to 4 halogen atoms, and wherein $F^1$ is —C(═O)O—, —OC(═O)—, —C(═O)$NR^8$—, —$R^8$NC(═O)—, or a covalent bond, and $F^2$ is —OC(═O)—, —C(═O)O—, —$R^8$NC(═O)—, —C(═O)$NR^8$—, or a covalent bond;

wherein $R^8$ is H or a $C_1$-$C_4$-alkyl group;

$R^{10}$ is hydrogen or a hydrocarbon moiety with 1 to 20 carbon atoms, wherein each hydrogen atom of the hydrocarbon moiety may optionally be substituted with a $C_1$-$C_4$-alkyl group or a halogen atom; and o is an integer from 2 to 10, in particular from 2 to 4.

Z may also be an alkylene moiety with 0 to 10, preferably 0 to 4, carbon atoms. Further, Z may also be an aromatic ring system with 5 to 10, preferably 6, carbon atoms. Even further, Z may be a cyclic aliphatic ring system with 5 to 10, preferably 6, carbon atoms.

Z is preferably —$(CH_2)_m$—, wherein m is an integer from 0 to 10, in particular from 0 to 4; —$C_6H_4$—, wherein the aromatic ring is optionally substituted with 1 to 4 $C_1$-$C_4$-alkyl groups or 1 to 4 halogen atoms; or —$C_6H_{10}$—, wherein the aliphatic ring is optionally substituted with 1 to 4 $C_1$-$C_4$-alkyl groups. F is preferably —COOH, —$COOR^4$, —$C_2H_3$, wherein $R^4$ is a $C_1$-$C_4$-alkyl group.

Preferably, $R^2$ is —H. More preferably, $R^2$ is H, $R^1$ is H or $CH_2OH$, and $R^3$ is —H.

In the structures (III) and (IV), n is preferably 0. This is particularly the case when the structures (III) or (IV) have been obtained from aldoses.

As described, in the structures (I), (II) and (V), R is —Z—F, wherein Z is a hydrocarbon moiety with 0 to 10 carbon atoms, optionally substituted with 1 to 4 $C_1$-$C_4$-alkyl groups or 1 to 4 halogen atoms, and F is —COOH, —CH$(COOH)_2$, —$COOR^4$, —CHO, —CH$(CHO)_2$, —$C_2H_3$, —$NH_2$, —$NHR^7$, —OH, —CH$(CH_2OH)_2$, wherein $R^4$ is a $C_1$-$C_4$-alkyl group; and $R^7$ is a $C_1$-$C_4$-alkyl group.

According to an embodiment of the invention, in the structures (III), (IV) and (VI), $R^5$ is preferably —$(CH_2)_m$C(═O)O— and $R^6$ is —OC(═O)$(CH_2)_m$—; or $R^5$ is —$C_6H_4$C(═O)O— and $R^6$ is —OC(═O)$C_6H_4$—, wherein the aromatic ring is optionally substituted with 1 to 4 $C_1$-$C_4$-alkyl groups or 1 to 4 halogen atoms; or $R^5$ is —$C_6H_{10}$C(═O)O— and $R^6$ is —OC(═O)$C_6H_{10}$—, wherein the aliphatic ring is optionally substituted with 1 to 4 $C_1$-$C_4$-alkyl groups; or $R^5$ is —$(CH_2)_m$OC(═O)— and $R^6$ is —C(═O)O$(CH_2)_m$—; or $R^5$ is —$C_6H_4$OC(═O)— and $R^6$ is —C(═O)O$C_6H_4$—, wherein the aromatic ring is optionally substituted with 1 to 4 $C_1$-$C_4$-alkyl groups or 1 to 4 halogen atoms; or $R^5$ is —$C_6H_{10}$OC(═O)— and $R^6$ is —C(═O)O$C_6H_{10}$—, wherein the aliphatic ring is optionally substituted with 1 to 4 $C_1$-$C_4$-alkyl groups; or $R^5$ is —$(CH_2)_m$C(═O)$NR^8$— and $R^6$ is —$R^8$NC(═O)$(CH_2)_m$—; or $R^5$ is —$C_6H_4$C(═O)$NR^8$— and $R^6$ is —$R^8$NC(═O)$C_6H_4$—, wherein the aromatic ring is optionally substituted with 1 to 4 $C_1$-$C_4$-alkyl groups or 1 to 4 halogen atoms; or $R^5$ is —$C_6H_{10}$C(═O)$NR^8$— and $R^6$ is —$R^8$NC(═O)$C_6H_{10}$—, wherein the aliphatic ring is optionally substituted with 1 to 4 $C_1$-$C_4$-alkyl groups; or $R^5$ is —$(CH_2)_m R^8$NC(═O)— and $R^6$ is —C(═O)$NR^8$$(CH_2)_m$—; or $R^5$ is —$C_6H_4R^8$NC(═O)— and $R^6$ is —C(═O)$NR^8C_6H_4$—, wherein the aromatic ring is optionally substituted with 1 to 4 $C_1$-$C_4$-alkyl groups or 1 to 4 halogen atoms; or $R^5$ is —$C_6H_{10}R^8$NC(═O)— and $R^6$ is —C(═O)$NR^8C_6H_{10}$—, wherein the aliphatic ring is optionally substituted with 1 to 4 $C_1$-$C_4$-alkyl groups;

wherein $R^8$ is H or a $C_1$-$C_4$-alkyl group; and m is an integer from 0 to 10, in particular from 0 to 4.

More preferably, in the structures (III), (IV) and (VI), $R^5$ is preferably —$(CH_2)_m$C(═O)O— and $R^6$ is —OC(═O)$(CH_2)_m$—; or $R^5$ is —$C_6H_4$C(═O)O— and $R^6$ is —OC(═O)$C_6H_4$—, wherein the aromatic ring is optionally substituted with 1 to 4 $C_1$-$C_4$-alkyl groups or 1 to 4 halogen atoms; or $R^5$ is —$C_6H_{10}$C(═O)O— and $R^6$ is —OC(═O)$C_6H_{10}$—, wherein the aliphatic ring is optionally substituted with 1 to 4 $C_1$-$C_4$-alkyl groups; or $R^5$ is —$(CH_2)_m$OC(═O)— and $R^6$ is —C(═O)O$(CH_2)_m$—; or $R^5$ is —$C_6H_4$OC(═O)— and $R^6$ is —C(═O)O$C_6H_4$—, wherein the aromatic ring is optionally substituted with 1 to 4 $C_1$-$C_4$-alkyl groups or 1 to 4 halogen atoms; or $R^5$ is —$C_6H_{10}$OC(═O)— and $R^6$ is —C(═O)O$C_6H_{10}$—, wherein the aliphatic ring is optionally substituted with 1 to 4 $C_1$-$C_4$-alkyl groups;

wherein m is an integer from 0 to 10, in particular from 0 to 4.

Thus, preferably, the polymer according to the invention comprises as repeat unit at least one of the following structures:

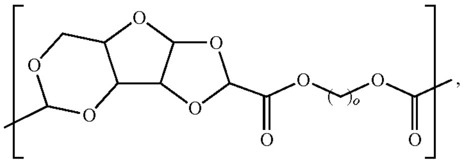
,

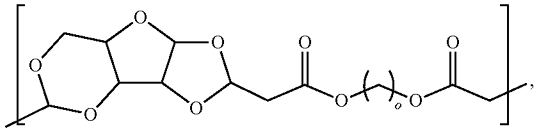
,

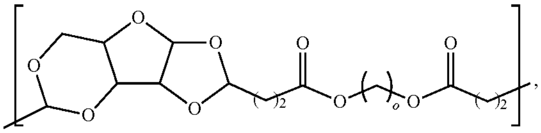
,

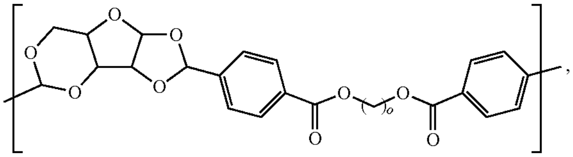
,

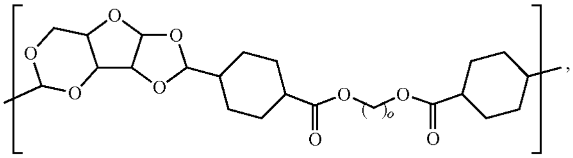
,

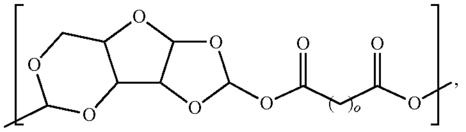
,

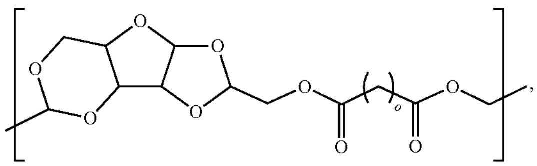
,

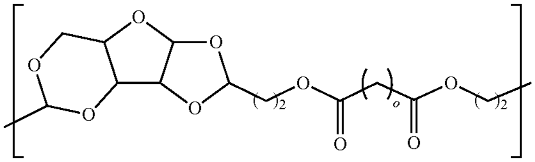
,

-continued
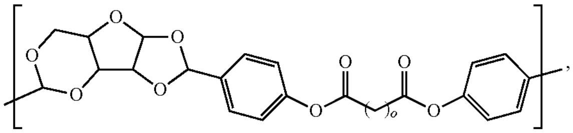,
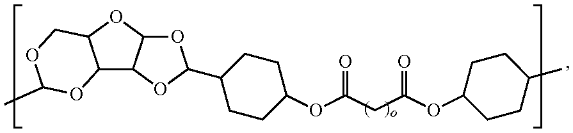,
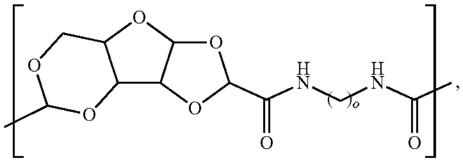,
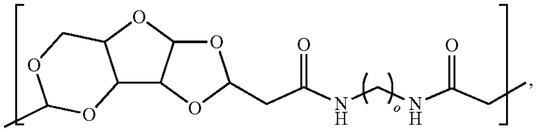,
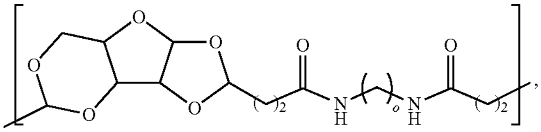,
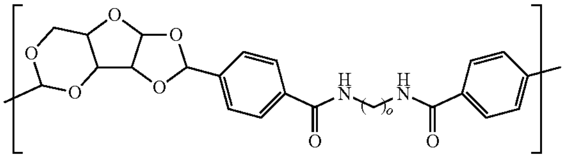,
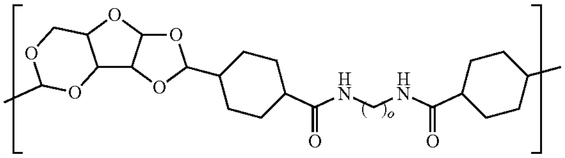,
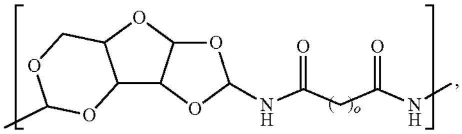,
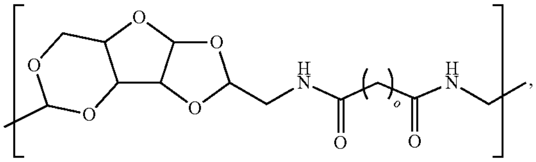,
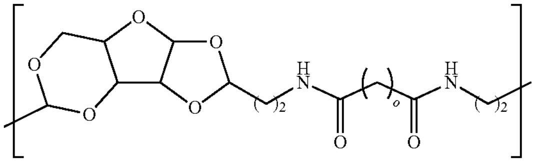,
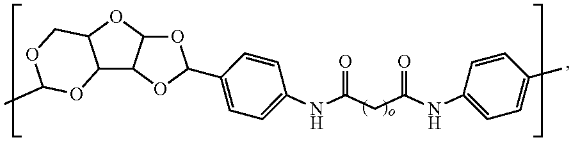,
-continued
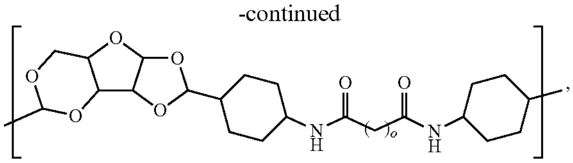,
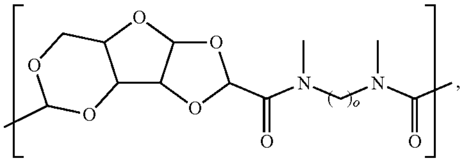,
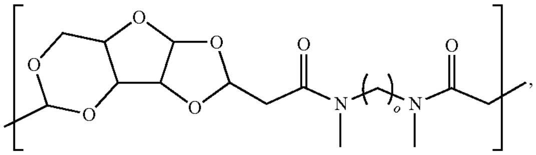,
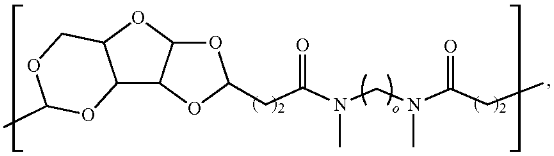,
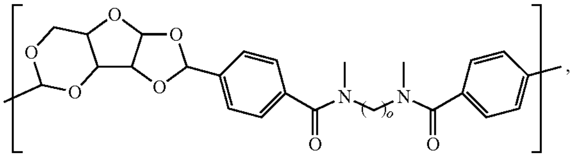,
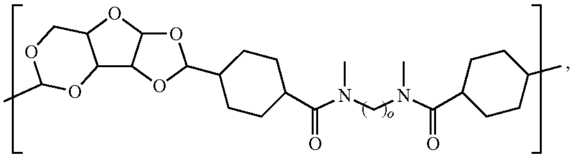,
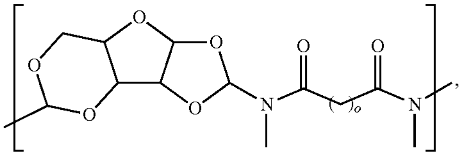,
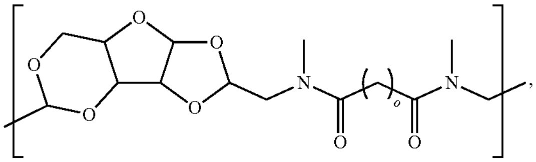,
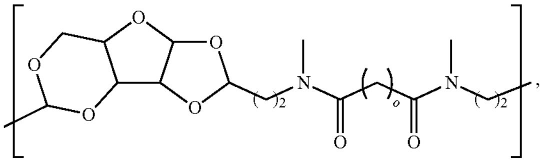,
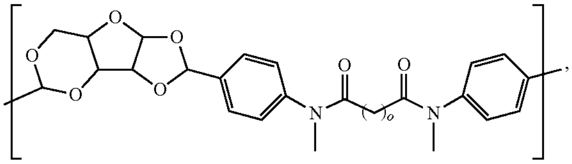,
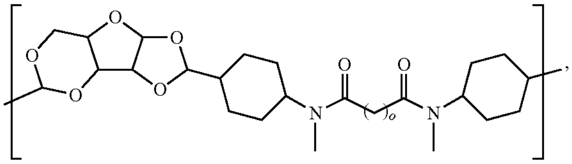, -continued
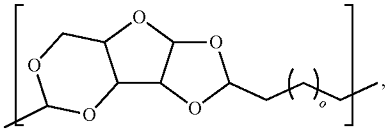
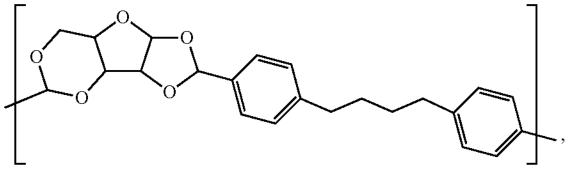
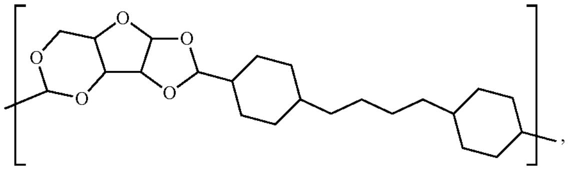
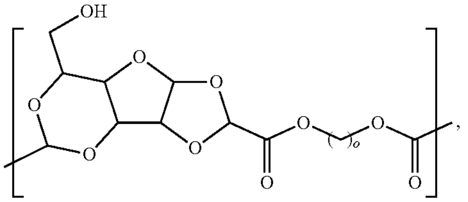
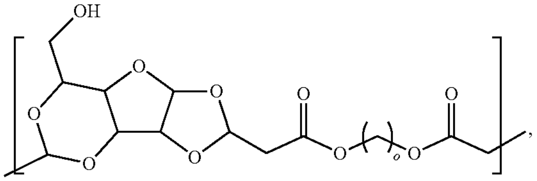
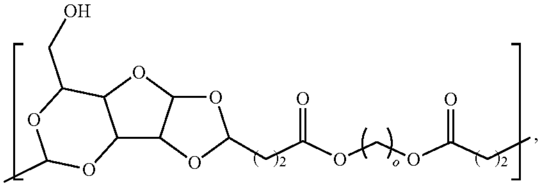
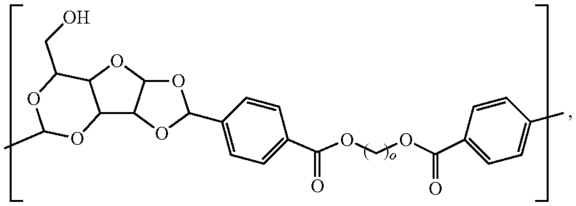
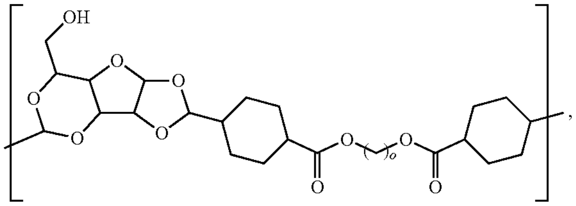
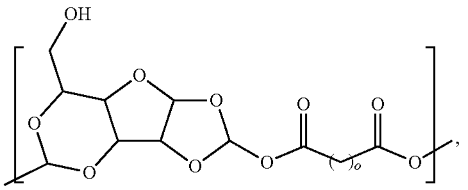
-continued
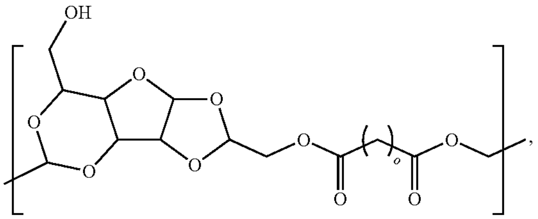
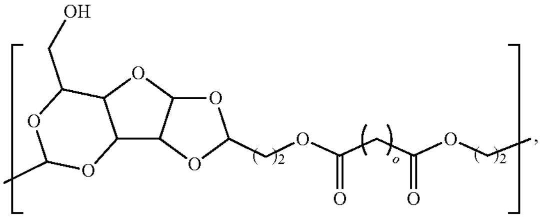
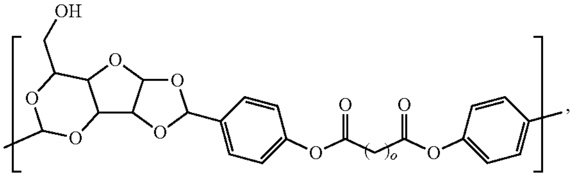
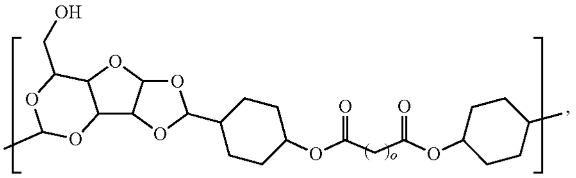
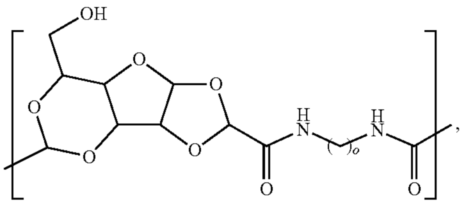
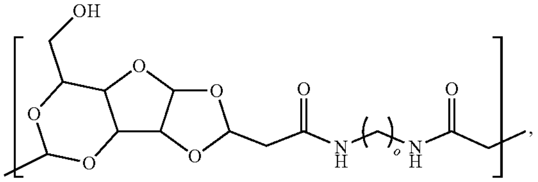
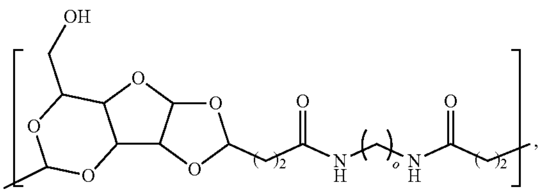
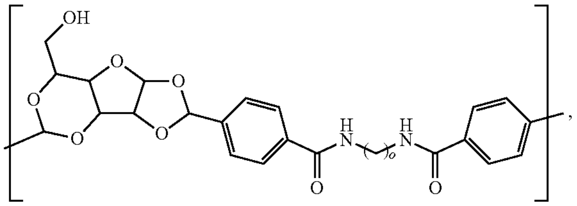

-continued
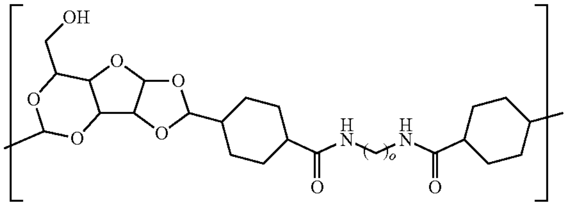,
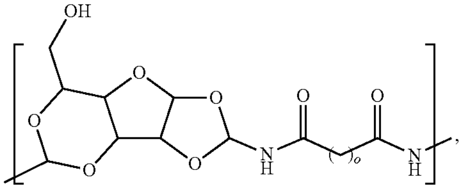,
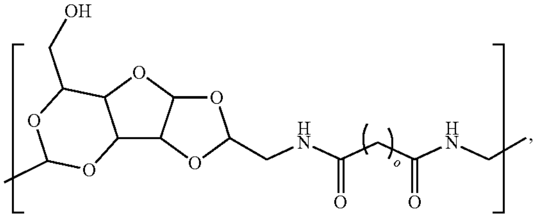,
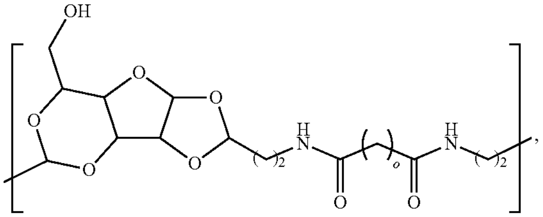,
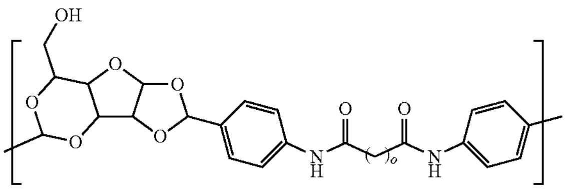,
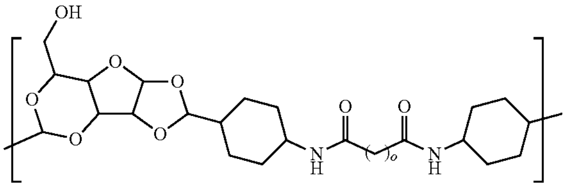,
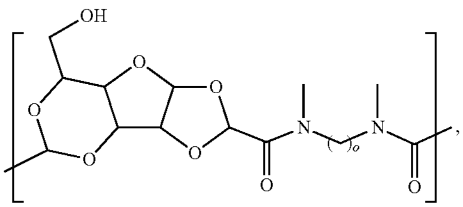,
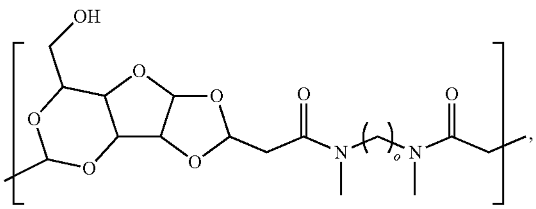,
-continued
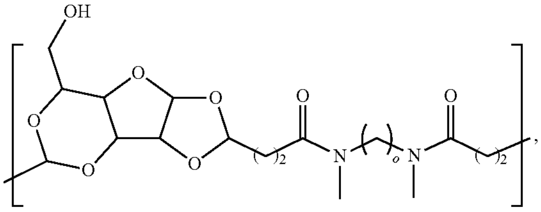,
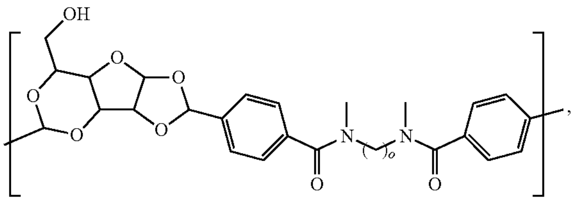,
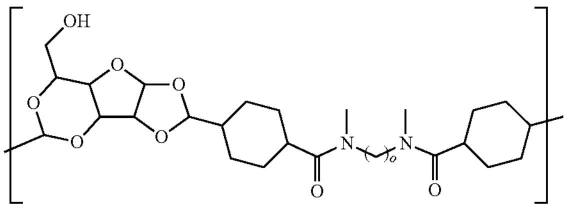,
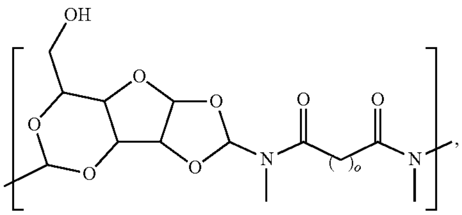,
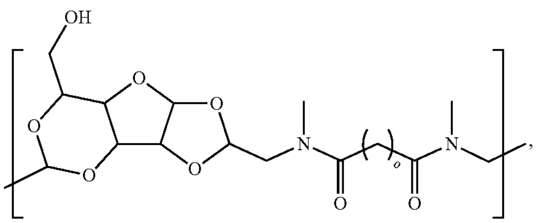,
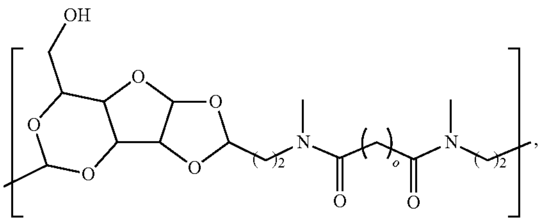,
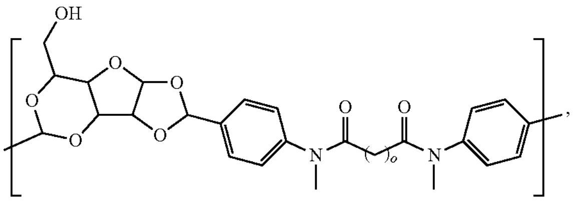,
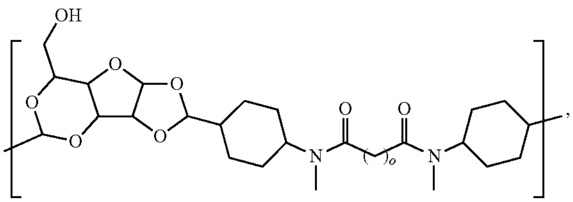, -continued
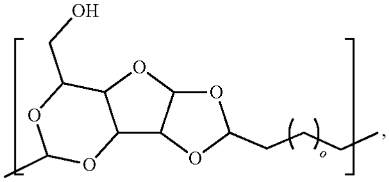,
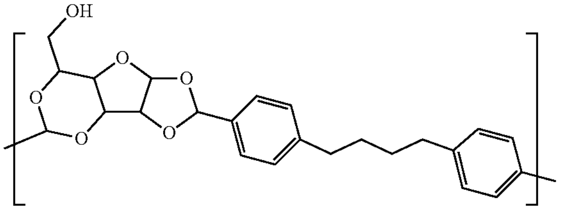,
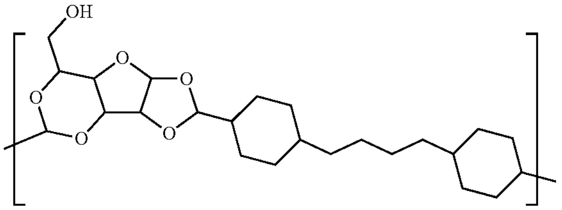,
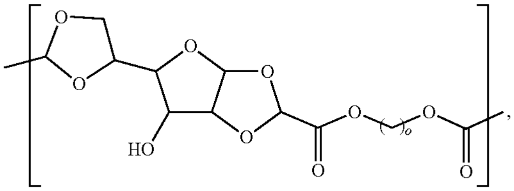,
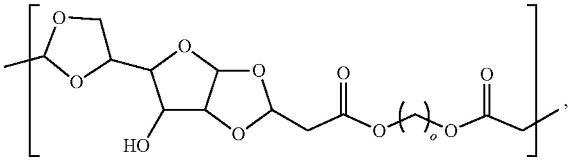,
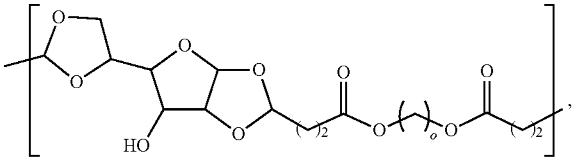,
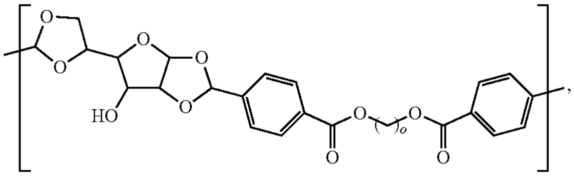,
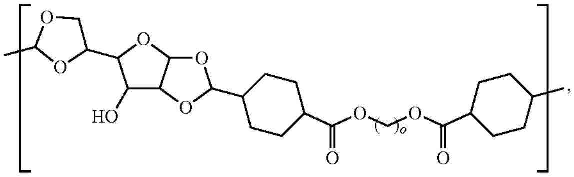,
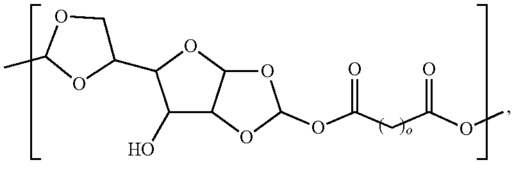,
-continued
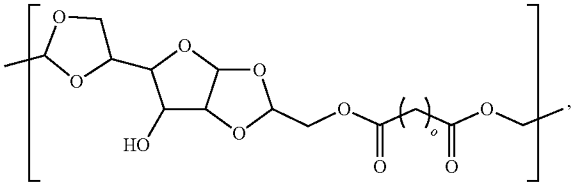,
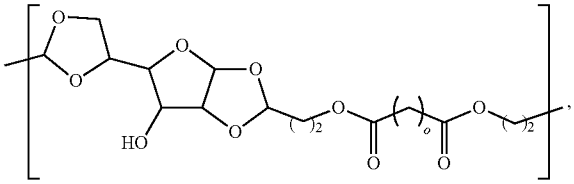,
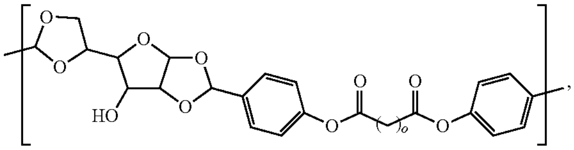,
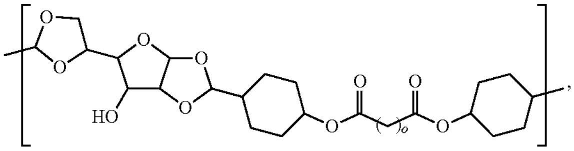,
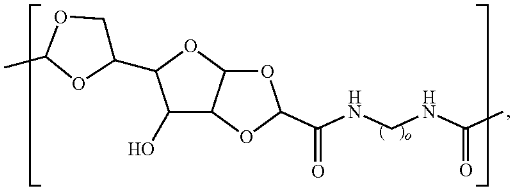,
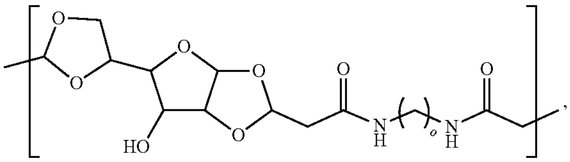,
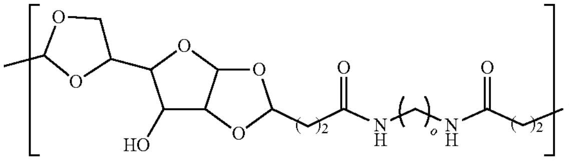,
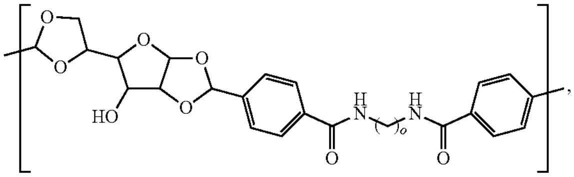,
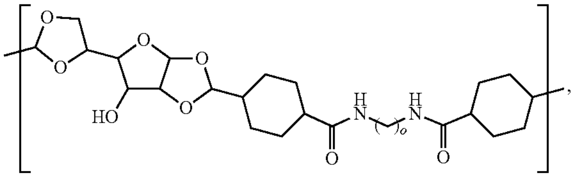,
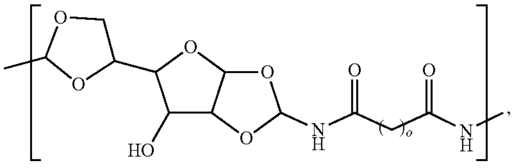, -continued
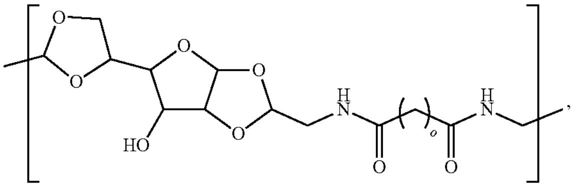
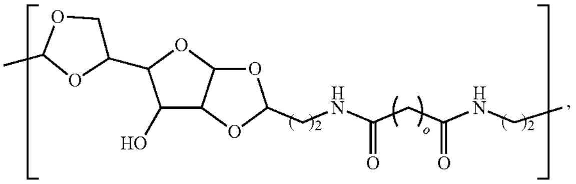
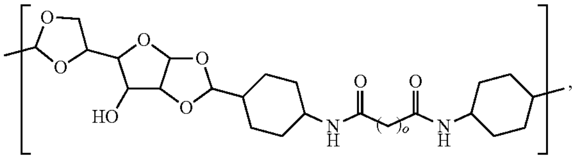
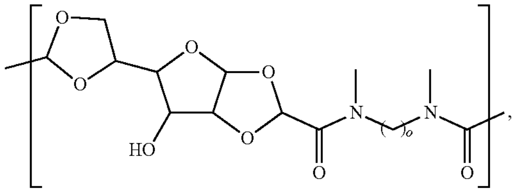
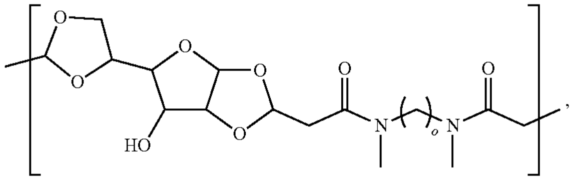
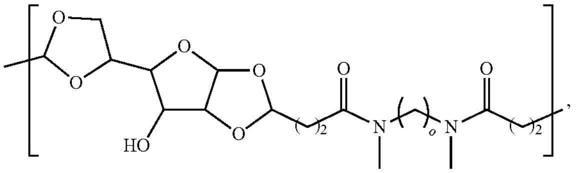
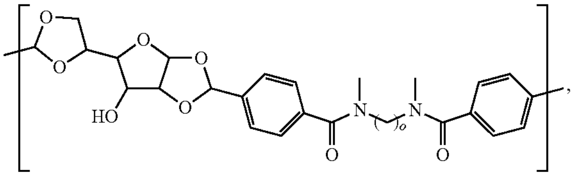
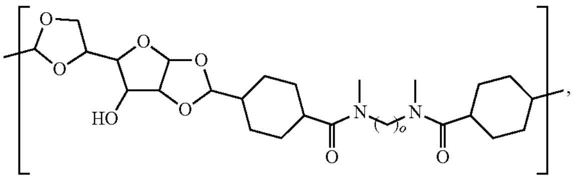
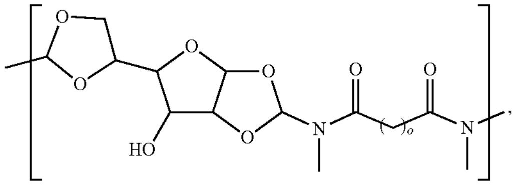
-continued
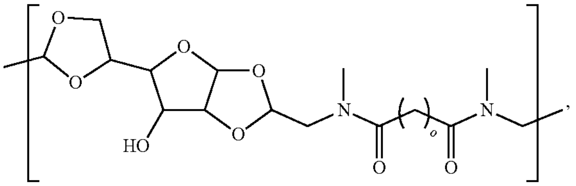
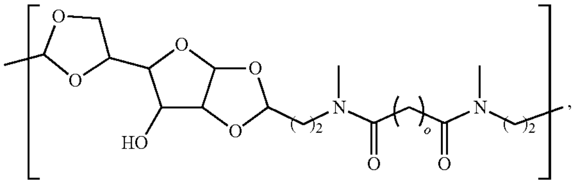
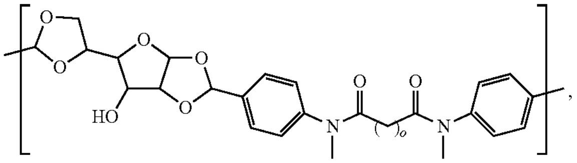
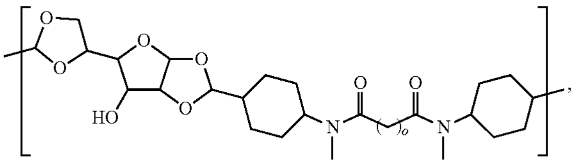
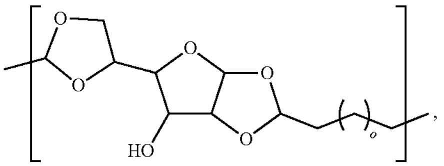
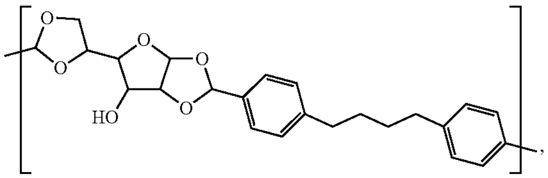
or
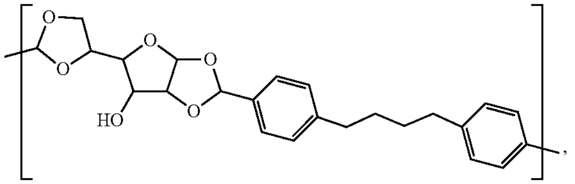
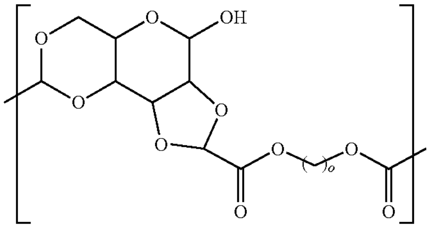
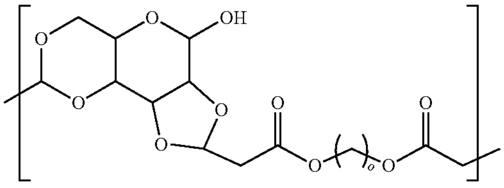

-continued
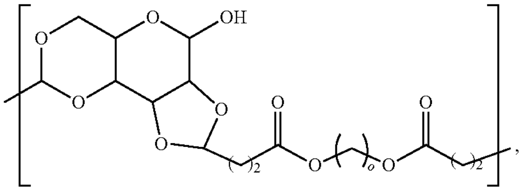
,
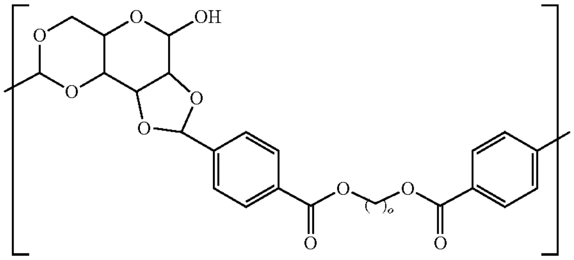
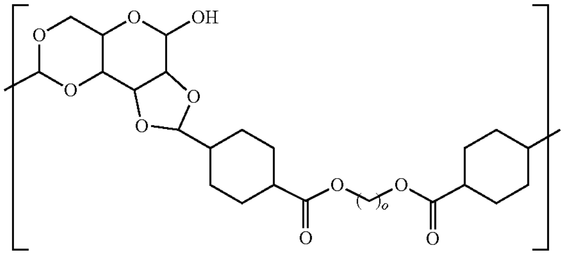
,
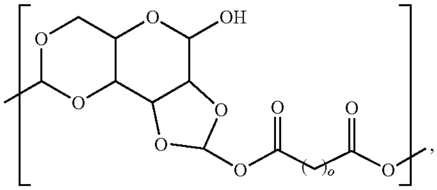
,
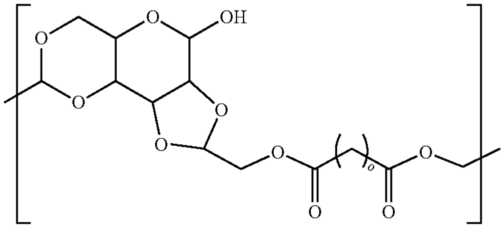
,
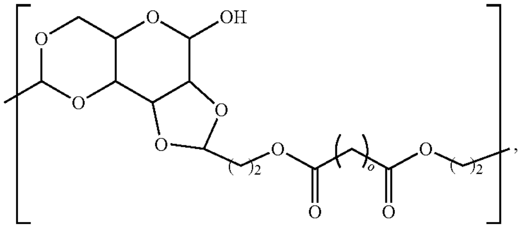
,
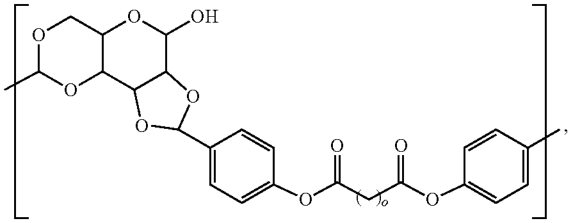
,
-continued
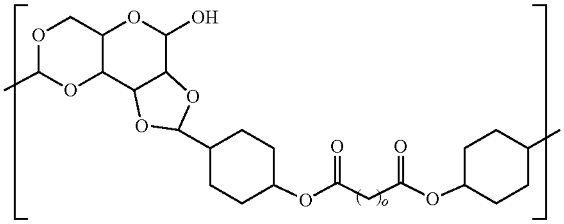
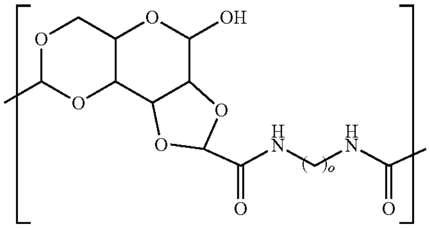
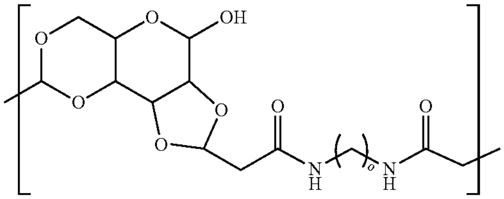
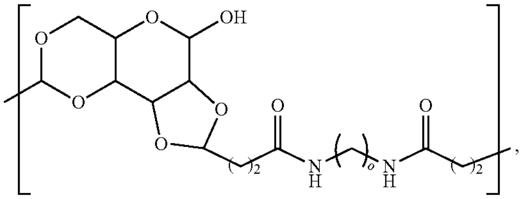
,
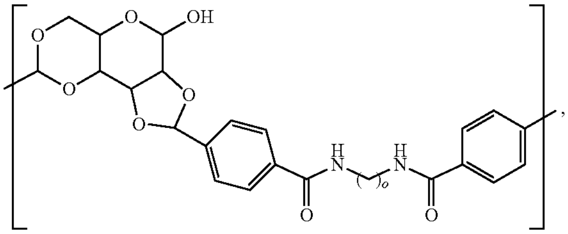
,
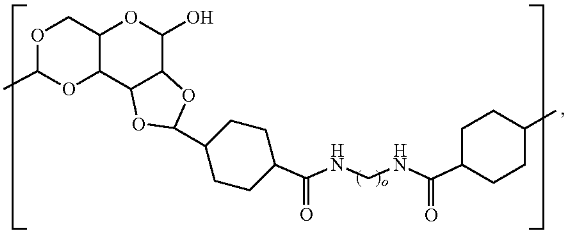
,
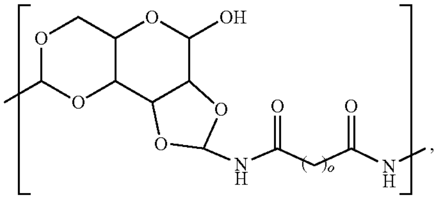
, -continued
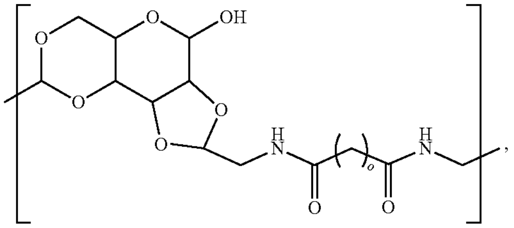
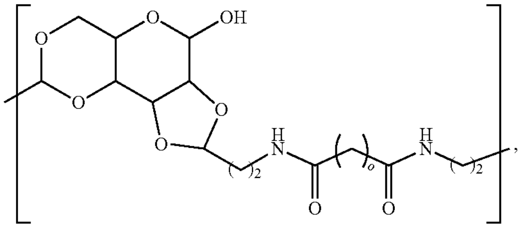
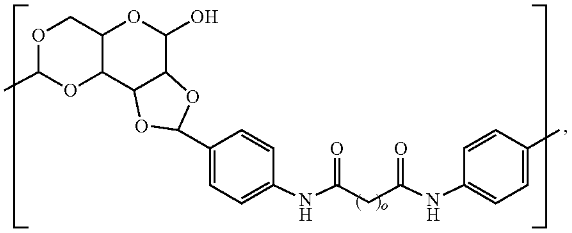
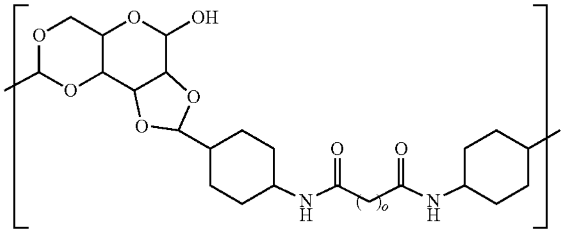
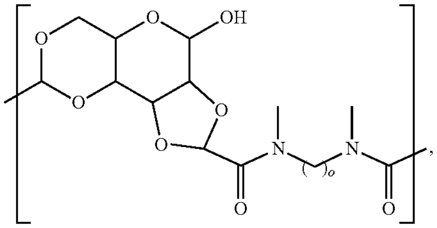
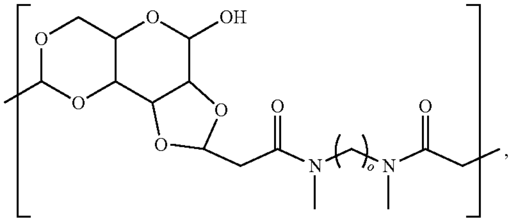
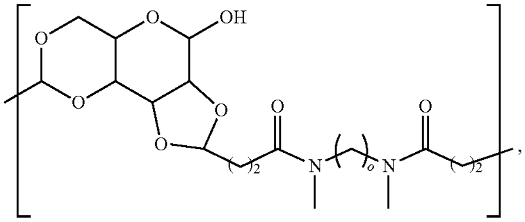
-continued
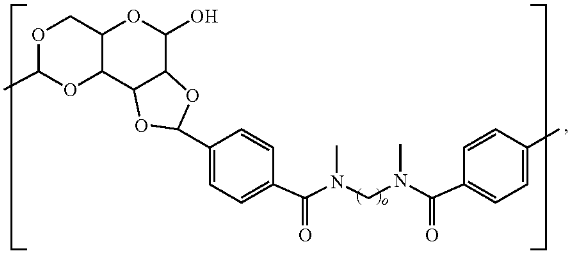
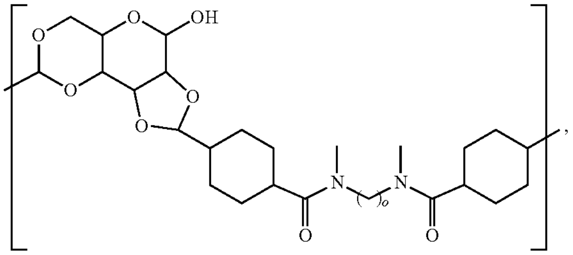
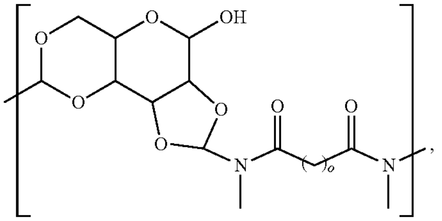
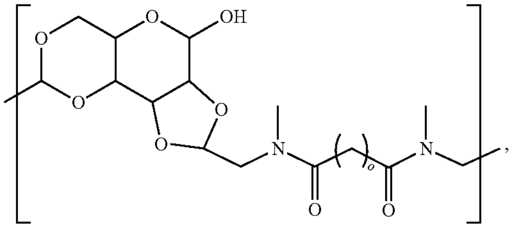
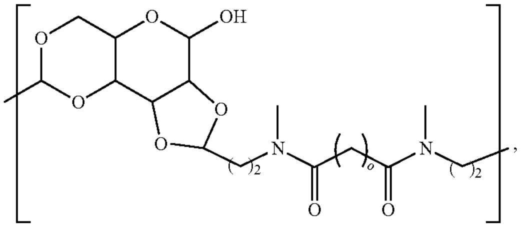
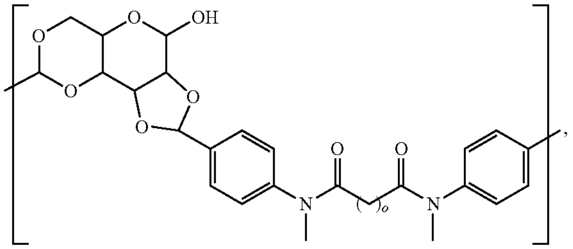
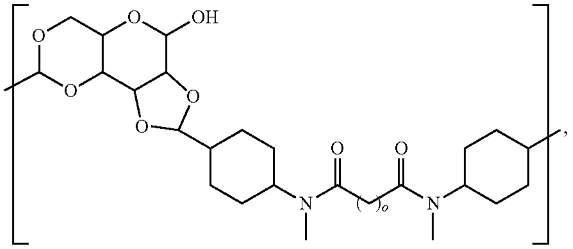

-continued

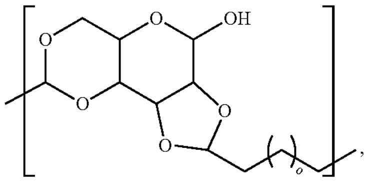

,

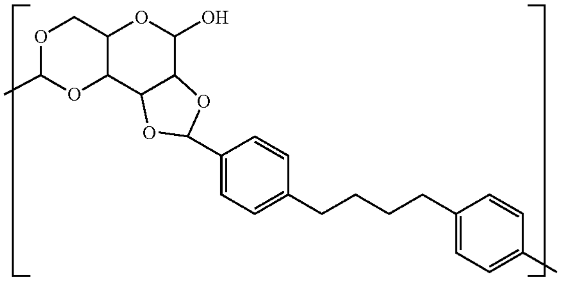

,

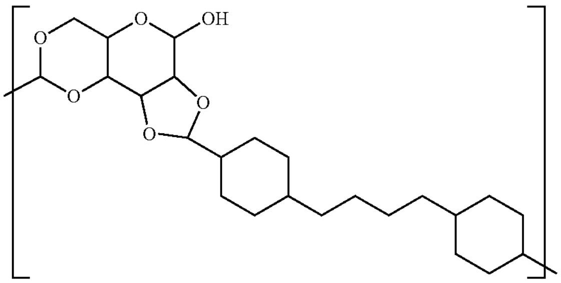

wherein o is an integer from 2 to 10, in particular from 2 to 4.

Preferably, the polymer according to the invention comprises the repeat unit with the structure (III), wherein n is 0 and $R^2$ is —H and $R^1$ is H or $CH_2OH$, in particular $R^1$ is H, and m is 0.

According to an embodiment of the invention, the polymer does not comprise the repeat unit with the structure (IV).

Very good results have been obtained, when in the structures (III), (IV) and (VI), $R^5$ is —C(═O)O— and $R^6$ is —OC(═O)— and o is 2.

Most preferably, the polymer according to the invention comprises as repeat unit

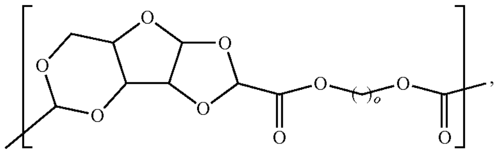

,

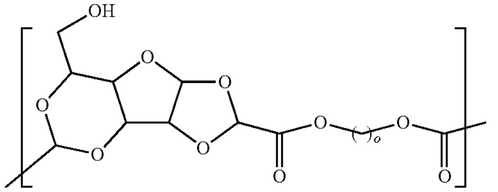

or

-continued

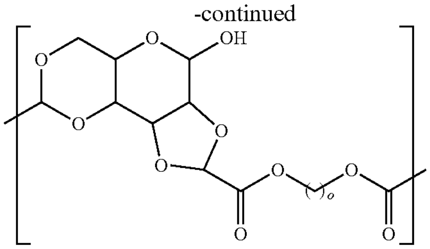

in particular

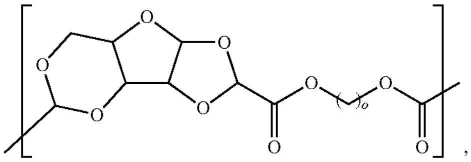

, wherein o is 2; and does not comprise the repeat unit with the structure (IV).

In the structures shown above, the ring systems preferably have the following stereochemistry:

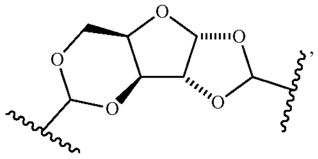

,

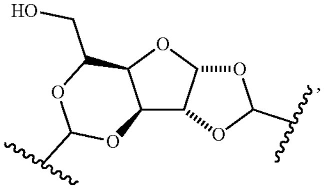

,

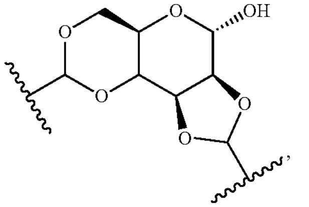

,

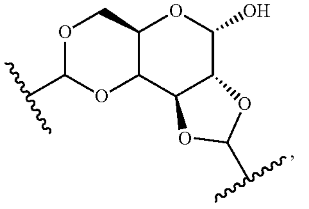

,

It was found that polymers comprising the aforementioned repeat units, in particular the repeat unit derived from xylose, show good thermal and/or mechanical properties. Moreover, these polymers can be easily prepared from cheap and abundant resources in a simple process.

The Method for the Preparation of the Polymer

The present invention also provides for a method for the preparation of a polymer according to the invention, wherein at least one compound according to the invention is subjected to a reaction, optionally with a compound with the formula $R^9$-L-$R^{9A}$, wherein $R^9$ and $R^{9A}$ are independently selected from the group consisting of —$OR^{11}$, —OH, —$NHR^8$, —COOH, —$COOR^4$ and a halogen atom;

wherein $R^{11}$ is selected from the group consisting of aryl and alkyl or $R^{11}$ of residue $R^9$ and $R^{11}$ of residue $R^{9A}$ form together a ring system;

wherein the halogen atom is selected from the group consisting of fluorine, chlorine, bromine and iodine;

wherein $R^4$, $R^8$, and o are as defined herein. This means that $R^9$ and $R^{9A}$ can be the same or different from each other.

Very good results have been obtained in a preferred embodiment of the invention, wherein $R^9$ and $R^{9A}$ are identical.

In another preferred embodiment of the invention good results have been obtained when L is $(CH_2)_O$.

In a further preferred embodiment of the invention good results have been obtained when $R^9$-L-$R^{9A}$ is a bis-(4-halogenphenyl) sulfone, in particular bis-(4-chlorophenyl) sulfone or a bis-(4-fluorophenyl) sulfone.

In a further preferred embodiment of the invention good results have been obtained when $R^9$-L-$R^{9A}$ is an organic carbonate that is L CO of formula (VIII) and $R^9$ and $R^{9A}$ are the same or different and $OR^{11}$, wherein $R^{11}$ is selected from the group consisting of aryl and alkyl or $R^{11}$ of residue $R^9$ and $R^{11}$ of residue $R^{9A}$ form together a ring system, i.e. forming a cyclic carbonate. For example, the organic carbonate can be a dialkyl carbonate, a diaryl carbonate or a cyclic carbonate. Examples for dialkyl carbonate are dimethyl carbonate, diethyl carbonate or methylethyl carbonate. Examples for diaryl carbonate are diphenyl carbonate or dimethylphenyl carbonate. Examples for cyclic carbonate are ethylene carbonate or trimethylene carbonate.

Preferably, the reaction is a polymerization reaction.

The at least one compound according to the invention and the compound with the formula $R^9$-L-$R^{9A}$ may be provided in different ratios, for example from 1:10 to 10:1. Preferably, the at least one compound according to the invention and the compound with the formula $R^9$-L-$R^{9A}$ are provided in a ratio of from 1:1 to 1:10, more preferably from 1:1 to 1:8, most preferably from 1:1 to 1:5.

Preferably, the reaction is conducted in the presence of a catalyst. A non-exhaustive list of polycondensation catalysts that can be used include: antimony trioxide, titanium isopropoxide, titanium butoxide, dibutyltin oxide, and zinc acetate.

The reaction may also be conducted in the presence of an initiator, in particular a radical initiator. This is particularly the case when the compound according to the invention contains a vinyl group.

The reaction may be carried out at different temperatures. Preferably, the reaction is carried out at a temperature of 30 to 250° C., more preferably at a temperature of 50 to 230° C., most preferably at a temperature of 100 to 220° C. If the reaction is conducted in the presence of a radical initiator, the temperature is preferably adjusted in view of the radical initiator, in particular in view of the half-life of the initiator. Examples for suitable radical initiators are peroxides such as benzoyl peroxide or azo initiators such as azoisobutyronitrile.

The reaction in the method for the preparation of a polymer according to the invention may also contain several steps. According to an embodiment of the method for the preparation of a polymer according to the invention, in a first step, the compound according to the invention and the compound with the formula $R^9$-L-$R^{9A}$ may be reacted to yield an intermediate. For example, a compound with the structure

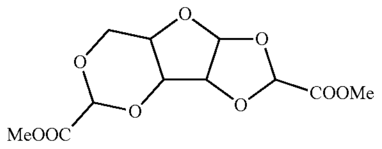 [SMILES: COC(=O)C1OCC2OC3OC(C(=O)OC)OC3C2O1]

may be reacted with ethanediol to yield as intermediate the corresponding transesterification intermediate containing two ethanediol units:

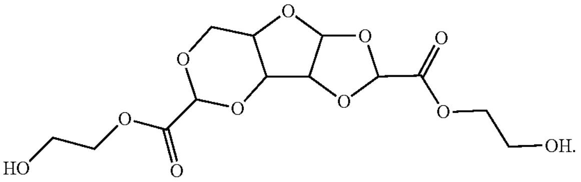 [SMILES: O=C(OCCO)C1OCC2OC3OC(C(=O)OCCO)OC3C2O1]

In a second step, the intermediate may then be polymerized to yield the polymer according to the invention. For example, the intermediate with the structure

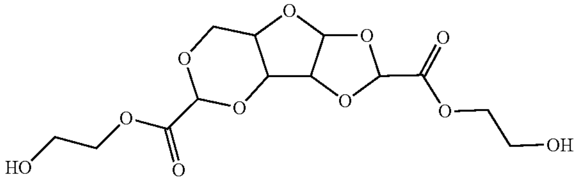 [SMILES: O=C(OCCO)C1OCC2OC3OC(C(=O)OCCO)OC3C2O1]

may be polymerized in a second step.

The first and the second step may be conducted at different temperatures. for example, the first step may be conducted at a temperature of from 100° C. to 200° C., preferably from 120° C. to 160° C., most preferably from 130° C. to 150° C. Further, the second step may be conducted at a temperature of from 150° C. to 250° C., preferably from 170° C. to 230° C., most preferably from 180° C. to 220° C.

The steps of the reaction may be conducted for various periods of times. For example, the first step of the reaction may be conducted for 1 to 15 hours, preferably for 1 to 10 hours, more preferably for 1 to 7 hours. The second step of the reaction may be conducted for 2 to 15 hours, preferably for 3 to 10 hours, more preferably for 3 to 8 hours.

In order to achieve high yields and also high molecular weights in the first and second step, in particular in the case of transesterification reactions, the pressure may be reduced. For example, in the transesterification reaction with ethanediol as a reagent described above, the reaction may be conducted first at normal pressure, then the pressure may be reduced. However, this may also be applied in the preparation of amides, polyesters, or polyamides.

Preferably, during the first step, the pressure is reduced to 100 mbar or less, more preferably 50 mbar or less, most preferably 10 mbar or less. Advantageously, during the second step, the pressure is reduced to 100 mbar or less, more preferably 50 mbar or less, more preferably 10 mbar or less, most preferably 1 mbar or less. By reducing the pressure during the reaction, in particular during the first and/or second step, higher yields and/or higher molecular weights of the polymers can be achieved.

The method according to the invention may also contain a purification step. The polymer may be purified by precipitation, extraction, and/or column chromatography. Preferably, the polymer is purified by precipitation.

The polymers according to the invention are promising candidates to replace poly(ethylene terephthalate). Therefore, the invention also provides for the use of the polymer according to the invention for the manufacture of sheets, fibers or molded objects, in particular as a replacement for poly(ethylene terephthalate).

Hereinafter, examples are described that are in no way meant to be limiting.

EXAMPLES

Methods

MALDI-TOF: Matrix-assisted laser desorption/ionization time-of-flight mass spectrometry (MALDI-TOF-MS) spectra of the synthesized polymers were acquired using a Bruker AutoFlex Speed instrument (Bremen, Germany). Samples were prepared by dissolving the polymers in 1,1,1,3,3,3-Hexafluoro-2-propanol (HFIP) at a concentration of 1 mg·mL$^{-1}$. A solution of 10 mg of 2,5-dihydroxbenzoic acid and 10 μL of trifluoroacetic acid (TFA) in 1 ml of THF was prepared. Subsequently, 0.5 μL of the polymer/HFIP solution was deposited on the steel analysis plate followed by 0.5 μL of the DHB/TFA solution. The laser power was set between 60-90% for the different polymer samples in order to achieve the optimal signal.

Gel Permeation Chromatography: The number- and weight-average molecular weights, $M_n$ and $M_w$, of the synthesized polymers were determined via gel permeation chromatography (GPC). An Agilent 1100 GPC/SEC was equipped with one PFG linear M column (PSS) and attached to an Agilent 1100 VWD/UV detector operated at 294 nm, a DAWN HELEOS II multi-angle laser light scattering (MALS) detector (Wyatt Technology Europe) and an Optilab TrEX RI detector (Wyatt). Samples were eluted in HFIP with 0.03 M K-TFAc at 1 mL min-1 at room temperature. Each polymer sample was analyzed twice to ensure precision of the instrument. To measure accurate molecular weight, polymethylmethacrylate (PMMA) standards purchased from PSS Polymer Standards Service, Germany were used to build a calibration curve that was applied to our data.

GC-MS Analysis: Gas chromatography-mass spectrometry spectra were obtained using an Agilent 7890B series GC equipped with a HP5-MS capillary column and an Agilent 5977A series Mass Spectroscopy detector. The GC-MS method was performed as follows: an injection temperature of 250° C., a column temperature program beginning at 50° C. for 1 min, followed by a ramp of 15° C./min to 300° C., a hold at 300° C. for 7 min, and a detection temperature of 290° C.

NMR Analysis: All NMR spectra were acquired using a Bruker Avance III 400 MHz spectrometer.

Syntheses

General Reaction Scheme a

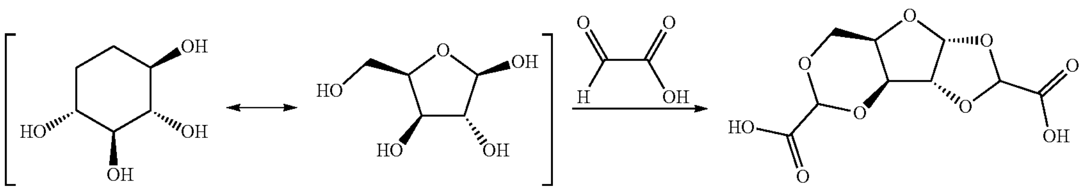

b

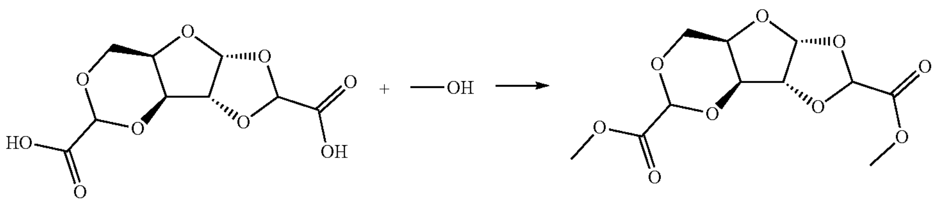

c

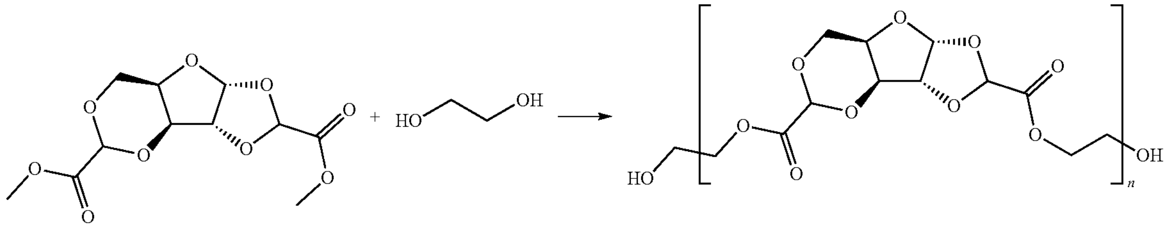

For the preparation of the monomer, glyoxylic acid, which is produced at commercial scale and can be readily produced from renewable ethylene glycol, was reacted with D-xylose (step a in the scheme above). The glyoxylic acid protected xylose was then esterified with methanol to enhance polycondensation rates and facilitate separation of the protected sugar (step b in the scheme above). Finally, the diester protected xylose, dimethylglyoxylate xylose (DMGX), was polymerized with ethylene glycol to form the fully renewable polyester, poly(ethylene dimethylglyoxylate xylose) (PEDMGX) (step c in the scheme above).

Synthesis of Dimethyl Glyoxylatexylose from Xylose.

D-xylose (200 g, 1.33 mol, 1.00 equiv.) was combined with glyoxylic acid monohydrate (500 g, 5.43 mol, 4.08 equiv.) in a 2 L, round-bottom flask and heated at 95° C. on a rotary evaporator. After dissolution of the xylose in the molten glyoxylic acid, 98 wt/wt % sulfuric acid (28.57 g, 270.8 mmol, 0.2 equiv.) was added dropwise. The pressure on the rotary evaporator was then slowly reduced to 20 mbar to continuously pull off the water that is produced as a by-product of the reaction. The reaction was stopped after yields of diglyoxylic acid protected xylose exceeded 93% (~3 h), as determined by. Methanol (1 L) was then added to the reaction mixture and the resulting solution was heated to reflux using an oil bath at 80° C. until yields of the dimethyl ester of the diglyoxylic acid-protected xylose exceeded 95% (~1 h) as determined by GC-FID. The reaction was then cooled to room temperature and neutralized with sodium hydroxide. The resulting salts were removed by filtration and the filtrate was concentrated in vacuo on a rotavap at 45° C. and 100 mbar. The residue was then dissolved in DCM (0.6 L) and transferred to a (2 L) separatory funnel. The organic phase was then washed with deionized water (1 L) three times to remove darkly coloured sugar degradation products and unreacted carboxylates. The organic phase was then extracted once with brine (1 L) and then transferred to a 1 L, round-bottom flask and concentrated in vacuo. The resulting residue was distilled using a distillation bridge at a pressure of 0.02 mbar and an oil bath temperature of 80-180° C. The distillate containing methyl glyoxylates and residual solvent obtained during the ramp between 80° C. and 180° C. was discarded. A second flask was equipped and a second fraction was collected, which contains the product. This viscous, yellow oil that was dissolved in DCM (0.5 L) and treated with activated carbon (30 g). After stirring at 700 RPM using a PTFE coated stir-bar for 4 h, the solution was filtered through a 0.2 μm nylon membrane filter to remove the activated carbon and concentrated in vacuo to afford the dimethylglyoxylate xylose as a viscous-colourless oil (205 g, 53%). This oil is a mixture of four stereoisomers. Alternatively, crystallization can be used instead of activated carbon treatment to remove yellow impurities. Cyrstallization was successfully persormed in methanol, cyclopentylmethyl ether, and toluene. Also, by using controlled-temperature crystallization we have managed to selectively crystallize the most abundant isomer, leaving the other 3 isomers in the mother liquor.

Figure 2:
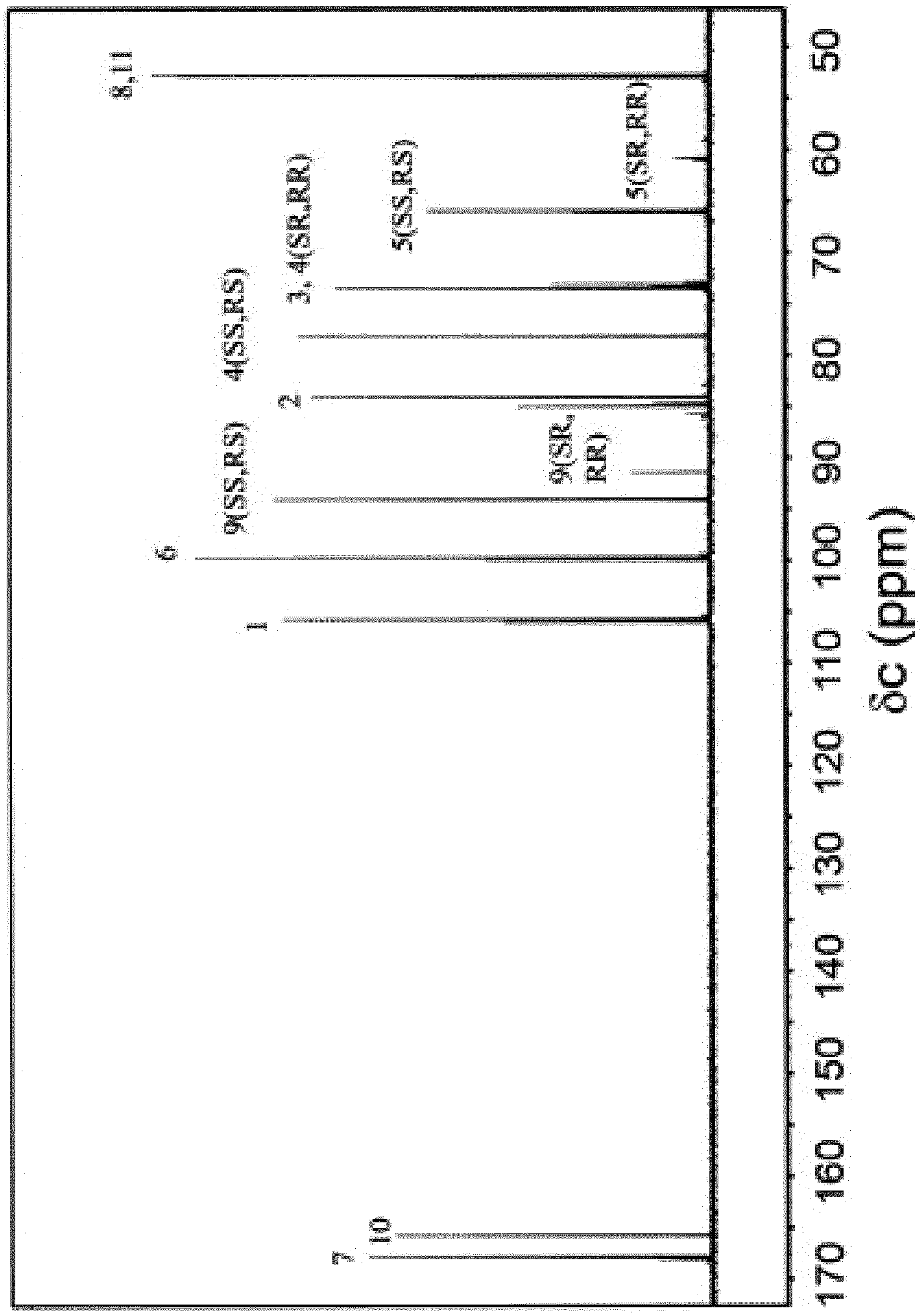
FIG. 2 shows a $^{13}C$ NMR spectrum of DMGX isomers in DMSO-d6.
Figure 3:
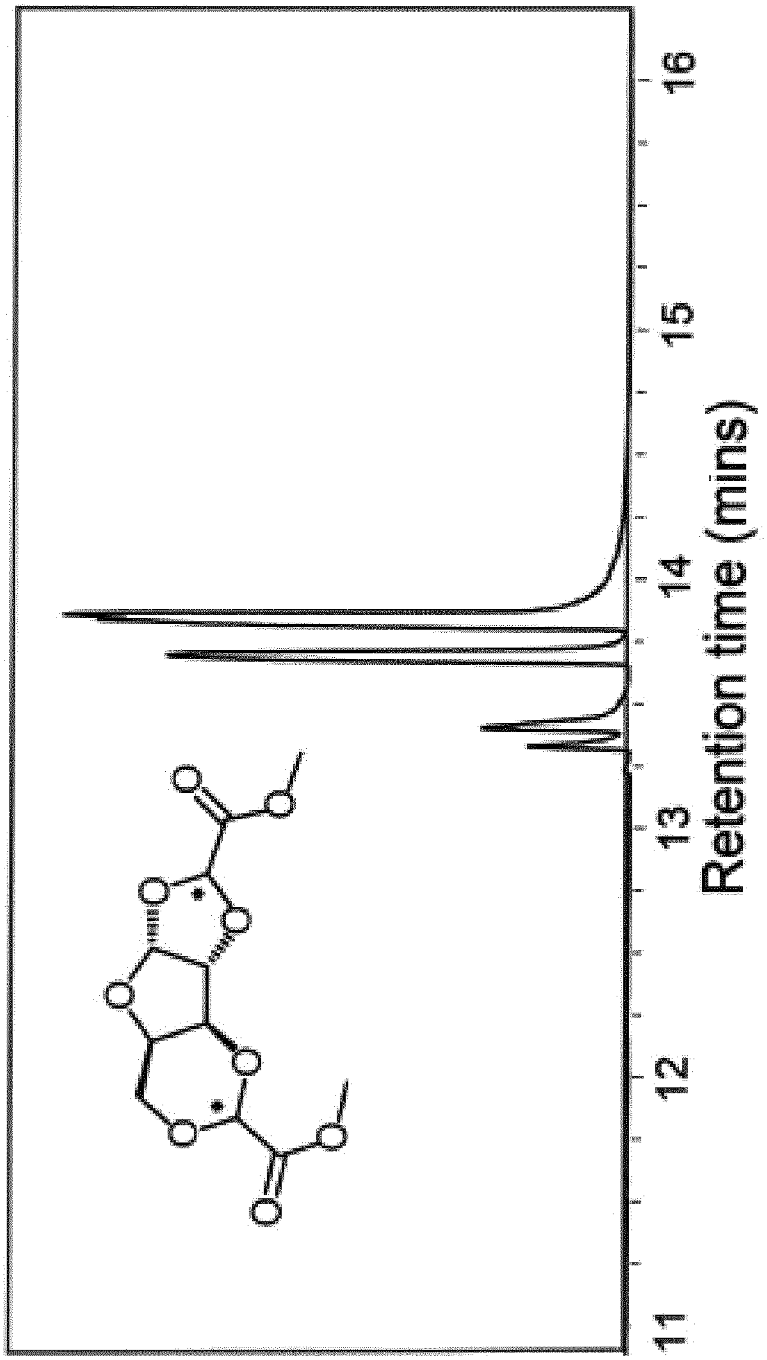
FIG. 3 shows a gas chromatography chromatogram (GC) of purified DMGX isomers.
Figure 4:
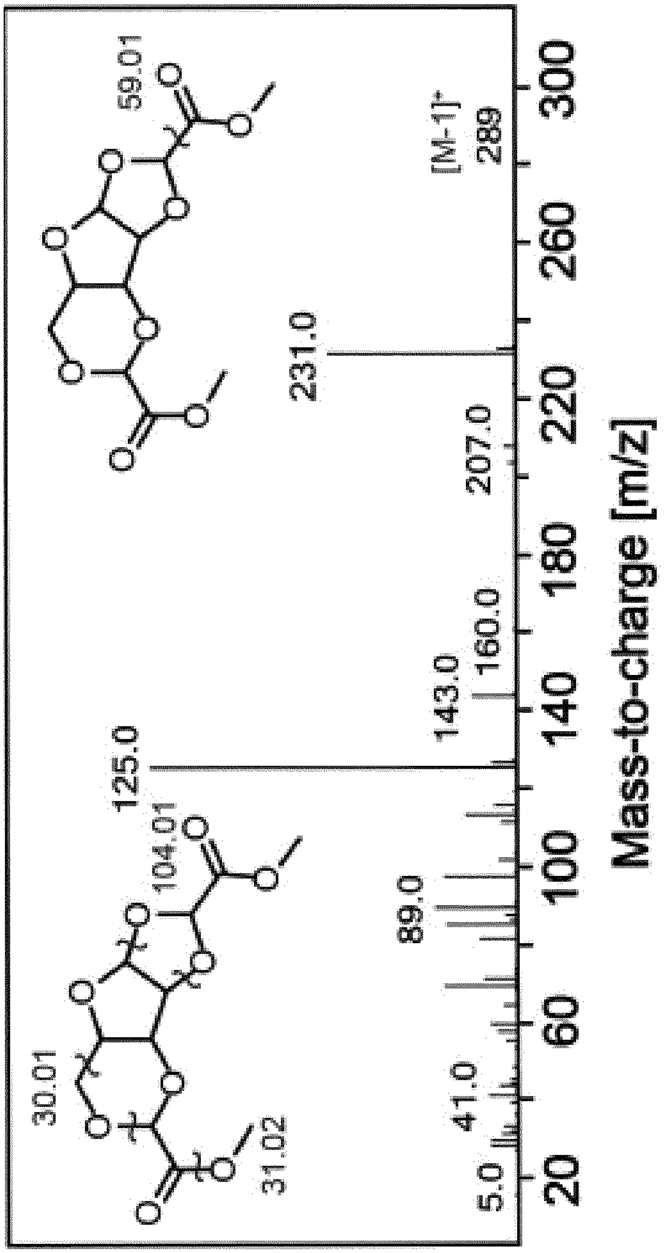
FIG. 4 shows a mass spectrum (MS) and fragmentation of DMGX isomers from GC-MS.

FIGS. 1 to 4 show analytical data for DMGX. FIG. 1 shows a 2D HSQC NMR showing the successful synthesis of DMGX isomers. The different isomers of DMGX give rise to different sets of peaks in the NMR spectrum. The letters in parentheses next to the peaks indicate the stereochemistry at carbons 6 and 9, respectively. FIG. 2 shows the $^{13}C$ NMR spectrum of DMGX isomers alone. The letters in parentheses next to the peaks indicate the stereochemistry at carbons 6 and 9, respectively. In FIG. 3, the different retention times in gas chromatography of the purified DMGX isomers become apparent. FIG. 4 shows the corresponding GC-MS mass peaks of the DMGX isomers as well as fragmentation products.

Exemplary Synthesis of Poly(Ethylene Dimethylglyoxylatexylose)

In a 2-neck round bottom flask, 1 molar equivalent of dimethyl glyoxylatexylose was charged with an excess of freshly distilled ethanediol (2.2 eq) and 0.4 wt % of antimony trioxide. The reaction vessel was attached to a distillation tube and was purged with nitrogen three times prior to heating. The vessel was heated to 140° C. in a sand bath with continuous stirring under a steady nitrogen flow for 2 h with methanol being pulled off by distillation. The bath was then brought to 200° C. for 2 h under continuous nitrogen flow. Vacuum was then applied at a pressure of 0.1 mbar and the reaction was allowed to continue for an additional 3 h with ethylene glycol being distilled off to drive the transesterification forward. The reaction was allowed to cool to room temperature and was subsequently dissolved in the minimum volume of 1,1,1,3,3,3-hexafluoro-2-propanol and precipitated by dropwise addition to methanol while stirring. The polymer was filtered out of solution and washed with methanol followed by drying under vacuum. Various transesterification catalysts, reaction times, and temperature can be used to produce the same polymer of various molecular weights.

Figure 5:
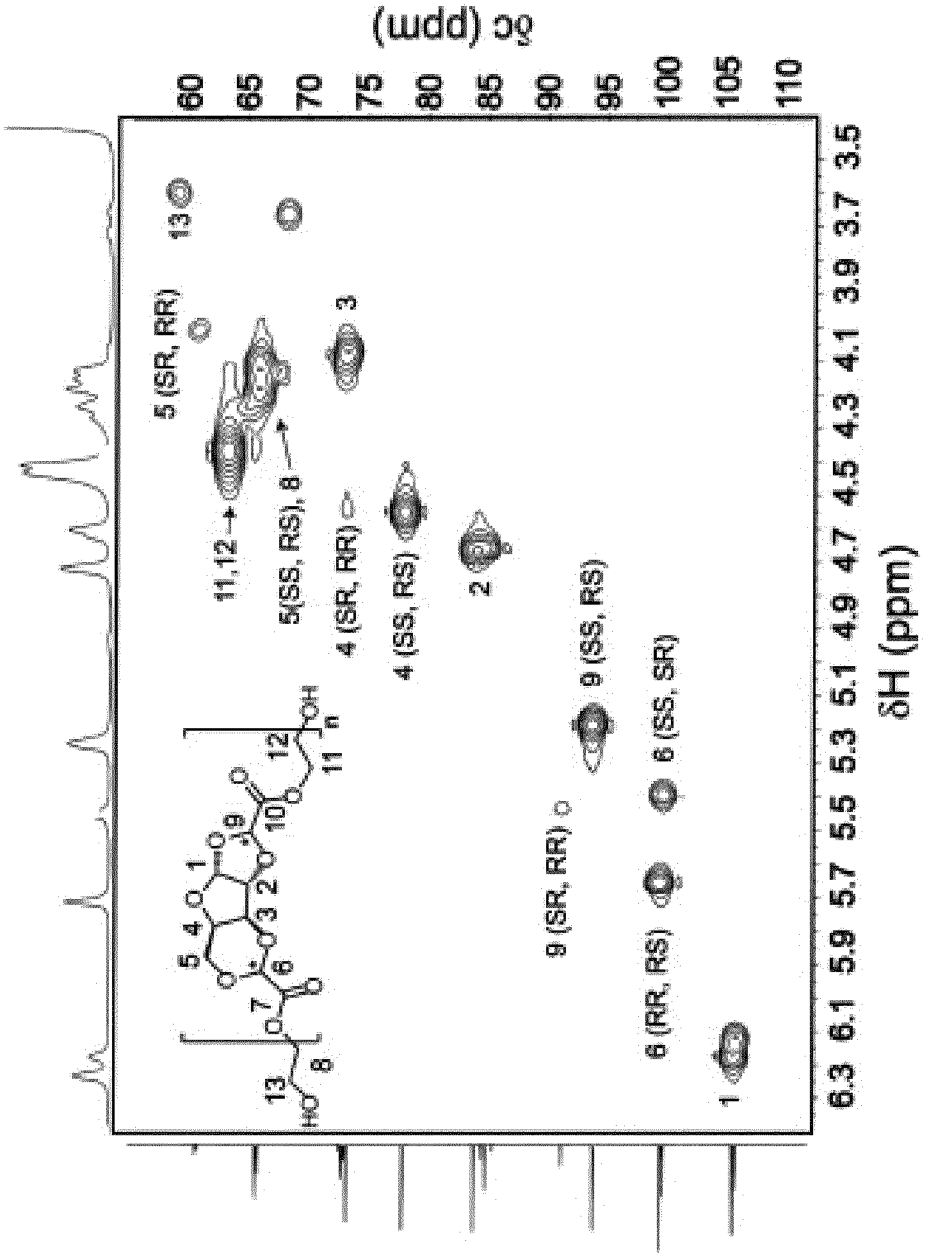
FIG. 5 shows a 2D HSQC NMR spectrum of poly (ethylene dimethylglyoxylate xylose) (PEDMGX).
Figure 6:
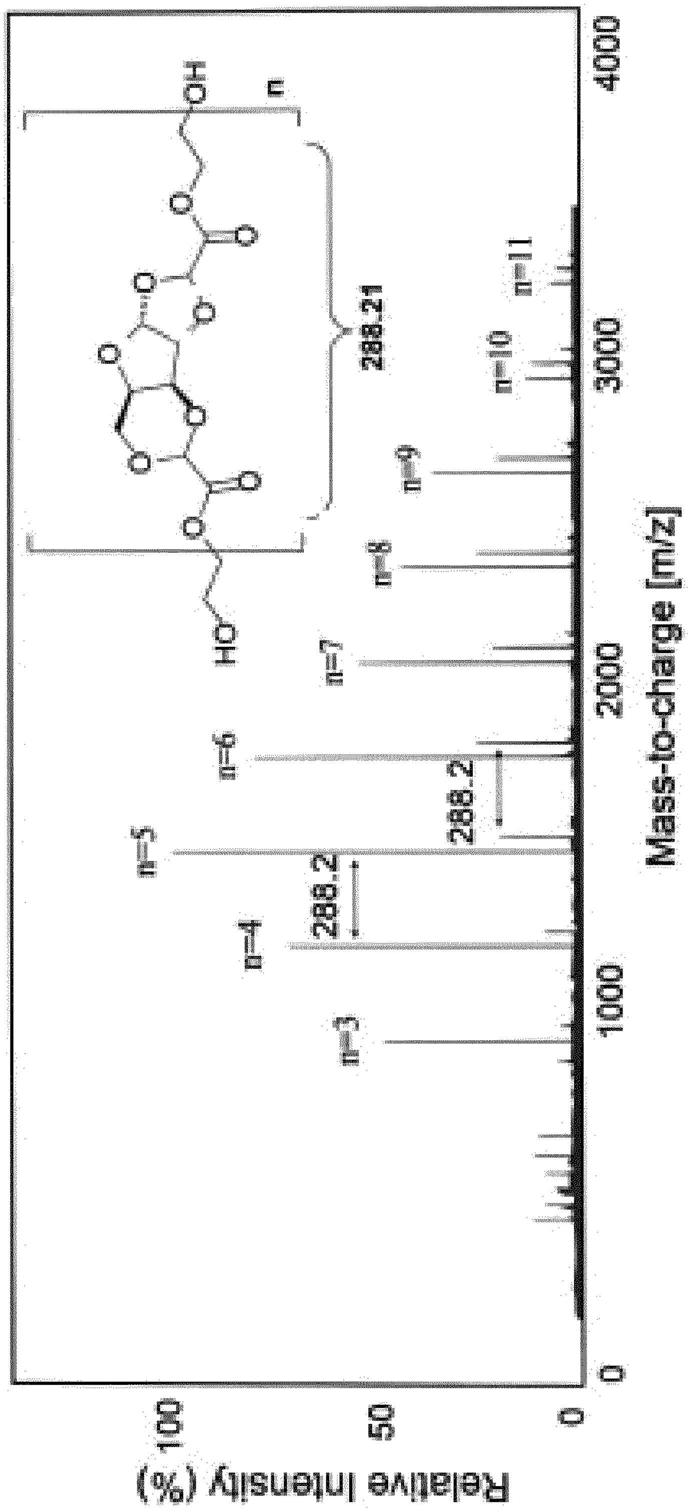
FIG. 6 shows a reflector positive MALDI spectrum of PEDMGX.
Figure 7:
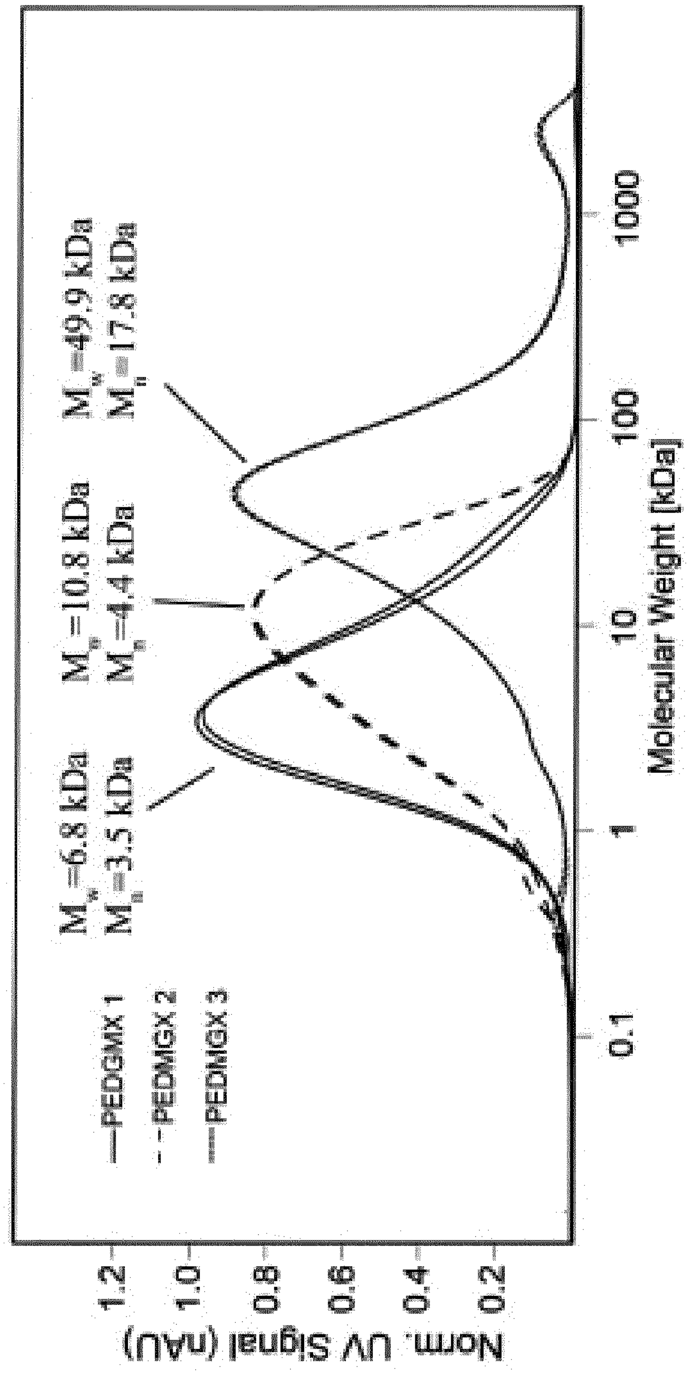
FIG. 7 shows a GPC chromatograms of three PEDMGX samples synthesized at various temperatures and durations.
Figure 8:
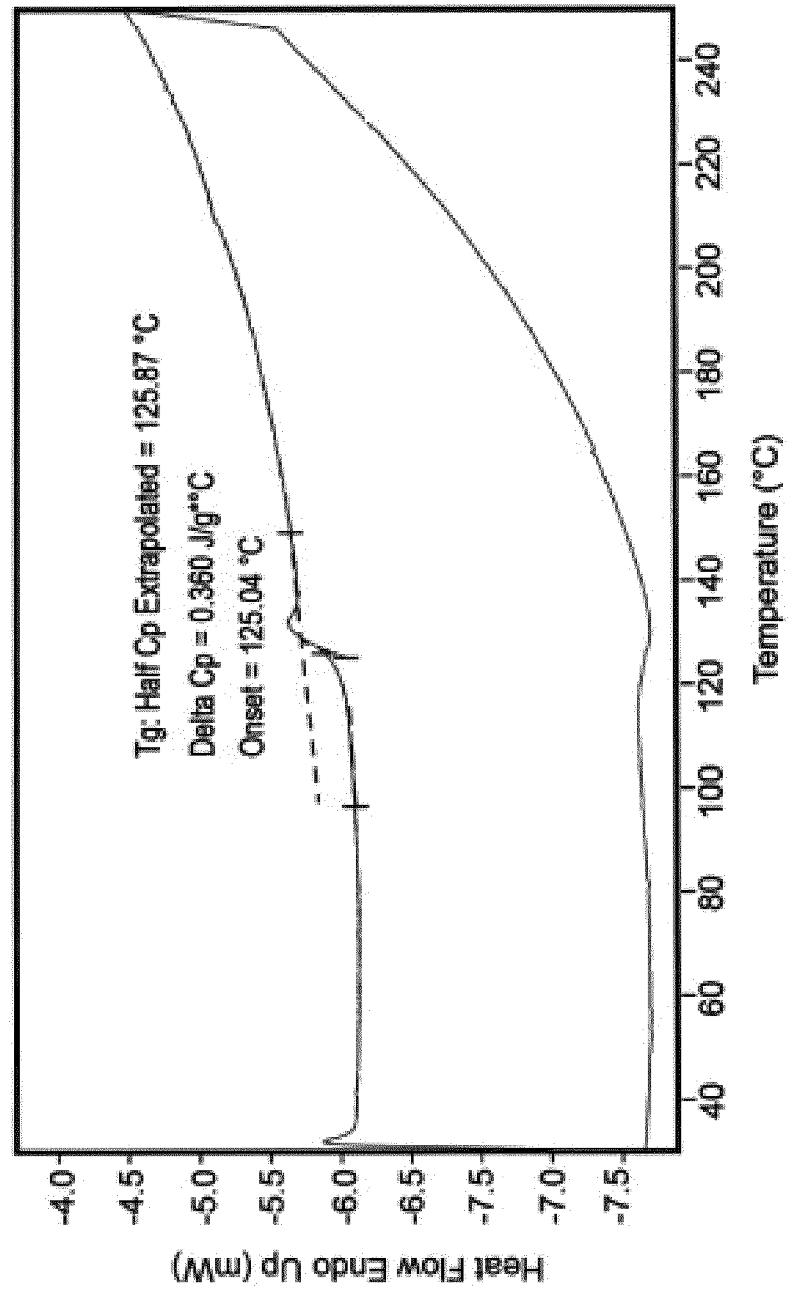
FIG. 8 shows a differential scanning calorimetry (DSC) curve of PEDMGX heating from 30° C. to 250° C. and cooling back down to 30° C.
Figure 9:
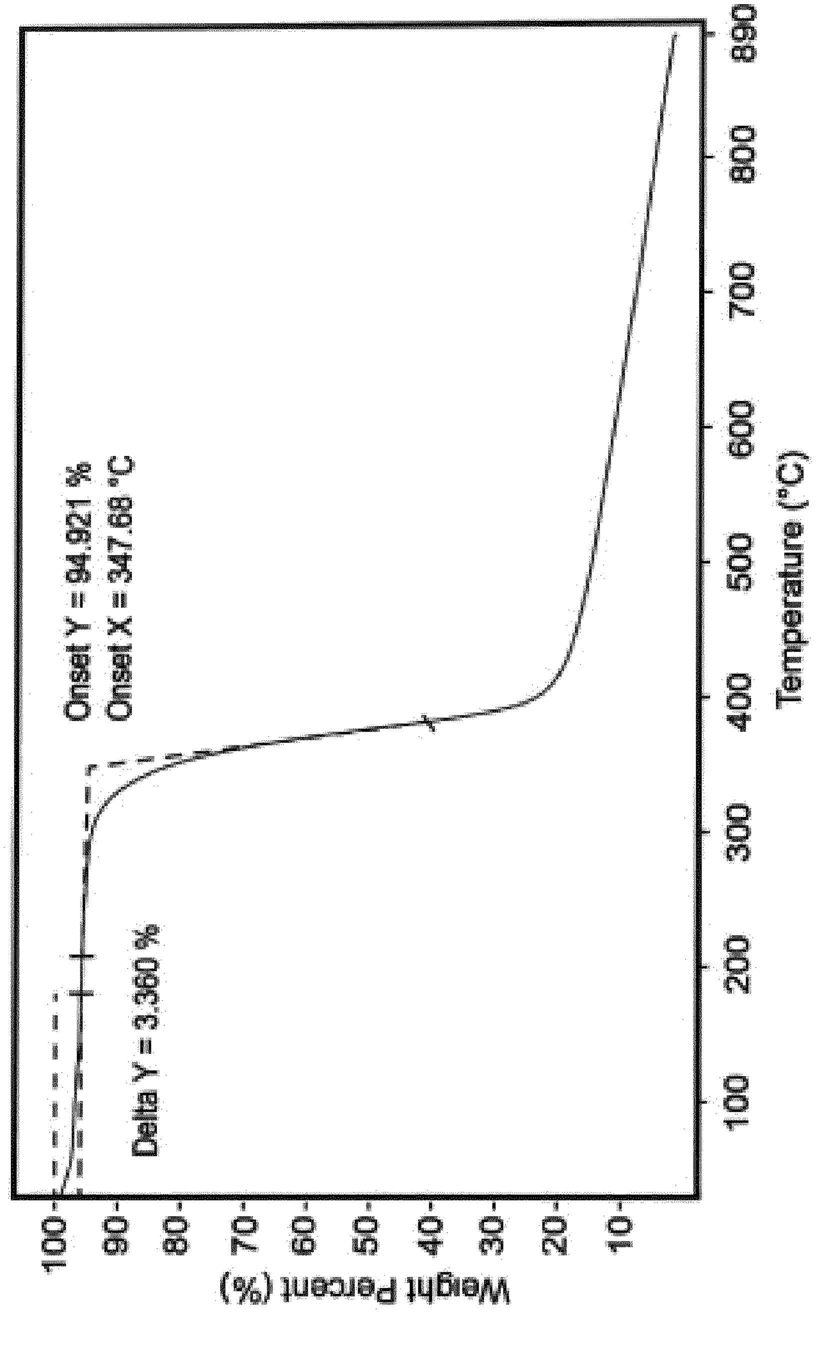
FIG. 9 shows a thermogravimetric analysis (TGA) curve of PEGDMX.

FIGS. 5 to 9 show analytical data for PEDMGX. FIG. 5 shows a 2D HSQC NMR spectrum showing the successful synthesis of PEDMGX. The letters in parentheses next to the peaks indicate the stereochemistry at carbons 6 and 9, respectively. FIG. 6 shows a reflector positive MALDI spectrum of PEDMGX. The distances between prominent peaks correspond to the molecular weight of the repeat unit. FIG. 7 shows the GPC chromatograms of three different PEDMGX samples synthesized at various temperatures and durations (not all of them described herein). Each polymer sample was analyzed twice to ensure precision of the instrument. For the measurements, polymethylmethacrylate (PMMA) molecular weight standards from PSS Polymer Standards Service, Germany, were used as external standards for molecular weight determination. Molecular weights ranging from 10 to 50 kDa were achieved, which is well within the commercial range of PET (20 to 60 kDa). FIG. 8 shows a DSC curve of PEDMGX heating from 30° C. to 250° C. and cooling back down to 30° C. DSC reveals a glass transition of 125° C., which is 45 to 55° C. higher than that of PET and 30° C. higher than that of PEF. This would enable the polyester to be used for significantly higher temperature applications without it loosing its properties, notably including those that require contact with boiling water. FIG. 9 shows a TGA curve of PEGDMX. TGA indicates a degradation temperature of approximately 348° C., which is lower than the 400° C. degradation temperature of PET, but it is still well above the processing and end-use temperatures of the polymer.

General Procedure for the Preparation of DMGX-Based Polyesters

The following polymers have been synthesized using the following method: Poly(ethylene dimethylglyoxylatexylose), Poly(propylene dimethylglyoxylatexylose), Poly (butylene dimethylglyoxylatexylose), Poly(pentylene dimethylglyoxylatexylose), Poly(hexylene dimethylglyoxylatexylose) by polymerizing DMGX with ethanediol, propanediol, butanediol, pentanediol, and hexanediol, respectively. Dimethylglyoxylate xylose (10 g, 34.4 mmol, 1.0 equiv.) was combined with diol (86 mmol, 2.5 equiv.), the re-esterification catalyst: zinc acetate (2 mg, 0.011 mmol, 0.00032 equiv), antioxidants: pentaerythritol tetrakis(3,5-di-tert-butyl-4-hydroxyhydrocinnamate) (13 mg, 0.011 mmol, 0.00032 equiv.) and triphenyl phosphite (13 mg, 0.042 mmol, 0.0012 equiv.) in a 250 mL, 2-neck, round-bottom flask. The reaction vessel was then equipped with a distillation bridge, a vacuum adapter, a valve for nitrogen flow, and a 250 mL collection flask and connected to a Schlenk line. The reaction vessel was back filled with nitrogen three times. Under a steady stream of nitrogen, the reaction mixture was then heated with stirring to 140° C. with an oil bath.

Over the course of the reaction, the methanol by-product was distilled from the reaction mixture and collected in the collection flask. Conversion was monitored by 1H-NMR and once complete re-esterification was observed (~1-4 h), the transesterification catalyst, antimony trioxide (2 mg, 0.0069 mmol, 0.0002 equiv), was added to the reaction mixture as a suspension in the diol (0.5 mL) under a positive nitrogen pressure. The reaction mixture was then heated to 190° C. and slowly over the course of 30 min the reaction vessel was evacuated to a pressure of 0.02 mbar to distil the diol reaction by-product and drive the polycondensation reaction. The reaction was monitored by 1H-NMR and the reaction was halted once the desired molecular weight was observed by end group analysis (high molecular weight ~8-14 h). Polymers derived from the mixture of 4 DMGX isomers were typically orange in color. Polymers synthesized from the most abundant DMGX isomer were generally highly transparent, and colorless. The reaction was cooled to room temperature and dissolved in a minimum volume of 1,1,1,3,3,3-hexafluoroisopropanol (250 mL). The resulting solution was added dropwise to a stirred solution of isopropanol (1 L) for the butanediol, pentanediol and hexanediol polymers and methanol (1 L) for the shorter chain diols, precipitating the polymer. The polymer was collected by filtration, washed with isopropanol, followed by diethyl ether, and dried in vacuo overnight at 60° C. and 0.02 mbar to afford the product as a brilliant-white powder. For the polymerizations with ethanediol and propanediol, where high molecular weights were more difficult to achieve, a more active transesterification catalyst, dibutyltin oxide (45 mg, 0.184 mmol, 0.0053 equiv.), was used in place of zinc acetate and antimony trioxide.

Synthesis of Dimethylglyoxylate xylose from Lignocellulosic Biomass

Biomass (extractives free and dried, 90.0 g) was massed into a tared, 1 L reagent bottle. To the bottle was then added the glyoxylic acid monohydrate (60.753 g, 660 mmol, 3.3 equiv.), 1,4-dioxane (250 mL), hydrochloric acid (37 wt %, 16.7 mL, 200 mmol, 1.0 equiv.), and two large PTFE coated stir bars. The flask was sealed with a GL 45 cap and placed in a shaking incubator for 24 hours at 300 RPM. Once completed, the reaction was cooled to room temperature (~23-30° C.). A filtration apparatus was assembled consisting of a 2 L filter flask, neoprene adapter, and a Buchner funnel with a piece of qualitative filter paper. The reaction was filtered through the Buchner funnel washing with dioxane (250 mL) to remove the cellulose-rich solids. The filtrate was then transferred to a 29/32, 2 L round-bottom flask and concentrated on a rotavap with a bath temperature of 45° C. and an ultimate pressure of 10 mbar. Into the concentrated lignin solution was then added an oval-type PTFE coated stir-bar followed by de-ionized water (1 L), which precipitated the lignin. The mixture was stirred at 500 RPM for 30 minutes to break the large agglomerations. The stir-bar was then removed. A filtration apparatus was assembled consisting of a 2 L filter flask, neoprene adapter, and membrane filtration apparatus with a 0.8 μm nylon membrane filter. The precipitated lignin solution was then filtered washing with deionized water (100 mL) through the nylon membrane filter to collect the lignin. The filtrate was transferred to a 29/32 2 L round bottom flask and sulfuric acid (1.7 mL, 31 mmol, 0.16 equiv., 98 wt %) was added. The reaction solution was then concentrated in vacuo on a rotavap (90° C., 200 mbar to 50 mbar) for three hours until all the water was evaporated from the reaction solution. To the reaction mixture was added methanol (400 mL) and an oval-type PTFE-coated stir bar. The reaction was then stirred for 12 hours at room temperature then neutralized with 10 N NaOH (3.1 mL). A filtration apparatus was assembled consisting of a 1 L filter flask, neoprene adapter, and a Buchner funnel (ground glass frit, porosity grade 3). The resultant salts and stir bars in the neutralized reaction solution were filtered off and the filtrate was dried on a rotary evaporator at 45° C. and 100 mbar. The residue was then dissolved in DCM (250 mL) and transferred to a 1 L separatory funnel. The solution as diluted with 250 mL of water and the funnel was sealed and shaken. The organic and aqueous phases were separated, and the aqueous phase was returned to the separatory funnel. It was extracted once more with DCM (250 mL). The layers were separated again, and the organic phases were combined and dried with magnesium sulfate (1-2 g). A filtration apparatus was assembled consisting of a 1 L filter flask, neoprene adapter, and a Buchner funnel (ground glass frit, porosity grade 3). The organic phase was then filtered to remove the magnesium sulfate and then transferred into a 29/32 1 L round bottom flask. The dichloromethane was removed by using a rotary evaporator at 45° C. and 500 mbar. The resulting oil was transferred to a 50 mL pear shaped round bottom flask and a PTFE coated stirbar was added. The flask was then fitted with a distillation train, two-neck round bottom flask, and a gas adapter and connected to a Schlenk line. Using an oil bath, the reaction solution was slowly heated to 180° C. Residual methyl glyoxylate was distilled off at 90-180° C. and 0.1 mbar. The collection flask was then swapped, and the desired product was pulled off as a distillate at 180° C. and 0.01 mbar. The distilled product was used for polymerization.

The invention claimed is:

1. A compound having the structure (I)

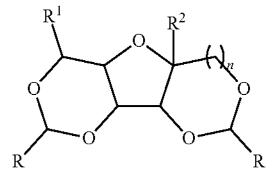

(I)

wherein $R^1$ is —H, —$CH_2OH$ or —$CH(OH)CH_2OH$;

$R^2$ is —H, —OH, or —$CH_2OH$;

n is 0 or 1;

R is either —Z—F or Y, and wherein Z is a hydrocarbon moiety with 0 to 10 carbon atoms, optionally substituted with 1 to 4 $C_1$-$C_4$-alkyl groups or 1 to 4 halogen atoms, and F is —COOH, —$CH(COOH)_2$, —$COOR^4$, —CHO, —$CH(CHO)_2$, —$C_2H_3$, —$C_2H$, —$N_3$, —$NH_2$, —$NHR^7$, —OH, —$CH(CH_2OH)_2$, and Y is hydrogen or a linear, branched or cyclic organic residue having 1 to 20 carbon atoms wherein $R^4$ is a $C_1$-$C_4$-alkyl group;

$R^7$ is a $C_1$-$C_4$-alkyl group, with the proviso that if R is Y and n is 0 at least one of $R^1$ or $R^2$ is not hydrogen.

2. The compound according to claim 1, wherein R is —Z—F, wherein Z is a hydrocarbon moiety with 0 to 10 carbon atoms, optionally substituted with 1 to 4 $C_1$-$C_4$-alkyl groups or 1 to 4 halogen atoms, and F is —COOH, —CH$(COOH)_2$, —$COOR^4$, —CHO, —$CH(CHO)_2$, —$C_2H_3$, —$C_2H$, —$N_3$, —$NH_2$, —$NHR_7$, —OH, or —$CH(CH_2OH)_2$.

3. The compound according to claim 1, wherein R is —$(CH_2)_mCOOH$;

—$(CH_2)_mCH(COOH)_2$; —$(CH_2)_mCOOR^4$; —$(CH_2)_mCH(COOR^4)_2$; —$(CH_2)_mCHO$;

—$(CH_2)_mCH(CHO)_2$; —$(CH_2)_mC_2H_3$; —$(CH_2)_mCH(C_2H_3)_2$; —$(CH_2)_mC_2H$; —$(CH_2)_mN_3$;

—$(CH_2)_mNH_2$; —$(CH_2)_mCH(NH_2)_2$; —$(CH_2)_mNHR_7$; —$(CH_2)_mCH(NHR_7)_2$; —$(CH_2)_mOH$; or —$(CH_2)_mCH(CH_2OH)_2$, where m is an integer from 0 to 10.

4. The compound according to claim 1, wherein R is

—$C_6H_4COOH$, wherein the aromatic ring is optionally substituted with 1 to 4 $C_1$-$C_4$-alkyl groups or 1 to 4 halogen atoms;

—$C_6H_{10}COOH$, wherein the aliphatic ring is optionally substituted with 1 to 4 $C_1$-$C_4$-alkyl groups;

—$C_6H_4COOR^4$, wherein the aromatic ring is optionally substituted with 1 to 4 $C_1$-$C_4$-alkyl groups or 1 to 4 halogen atoms;

—$C_6H_{10}COOR^4$, wherein the aliphatic ring is optionally substituted with 1 to 4 $C_1$-$C_4$-alkyl groups;

—$C_6H_4CHO$, wherein the aromatic ring is optionally substituted with 1 to 4 $C_1$-$C_4$-alkyl groups or 1 to 4 halogen atoms;

—$C_6H_{10}CHO$, wherein the aliphatic ring is optionally substituted with 1 to 4 $C_1$-$C_4$-alkyl groups;

—$C_6H_4C_2H_3$, wherein the aromatic ring is optionally substituted with 1 to 4 $C_1$-$C_4$-alkyl groups or 1 to 4 halogen atoms;

—$C_6H_{10}C_2H_3$, wherein the aliphatic ring is optionally substituted with 1 to 4 $C_1$-$C_4$-alkyl groups;

—$C_6H_4C_2H$, wherein the aromatic ring is optionally substituted with 1 to 4 $C_1$-$C_4$-alkyl groups or 1 to 4 halogen atoms;

—$C_6H_{10}C_2H$, wherein the aliphatic ring is optionally substituted with 1 to 4 $C_1$-$C_4$-alkyl groups;

—$C_6H_4N_3$, wherein the aromatic ring is optionally substituted with 1 to 4 $C_1$-$C_4$-alkyl groups or 1 to 4 halogen atoms;

—$C_6H_{10}N_3$, wherein the aliphatic ring is optionally substituted with 1 to 4 $C_1$-$C_4$-alkyl groups;

—$C_6H_4NH_2$, wherein the aromatic ring is optionally substituted with 1 to 4 $C_1$-$C_4$-alkyl groups or 1 to 4 halogen atoms;

—$C_6H_{10}NH_2$, wherein the aliphatic ring is optionally substituted with 1 to 4 $C_1$-$C_4$-alkyl groups;

—$C_6H_4NHR_7$, wherein the aromatic ring is optionally substituted with 1 to 4 $C_1$-$C_4$-alkyl groups or 1 to 4 halogen atoms;

—$C_6H_{10}NHR_7$, wherein the aliphatic ring is optionally substituted with 1 to 4 $C_1$-$C_4$-alkyl groups;

—$C_6H_4OH$, wherein the aromatic ring is optionally substituted with 1 to 4 $C_1$-$C_4$-alkyl groups or 1 to 4 halogen atoms; or —$C_6H_{10}OH$, wherein the aliphatic ring is optionally substituted with 1 to 4 $C_1$-$C_4$-alkyl groups.

5. The compound according to claim 1, wherein n is 0 and $R^2$ is —H.

6. The compound according to claim 1, wherein R is:

—$(CH_2)_mCOOR^4$; —$C_6H_4COOR^4$, wherein the aromatic ring is optionally substituted with 1 to 4 $C_1$-$C_4$-alkyl groups; —$C_6H_{10}COOR^4$, wherein the aliphatic ring is optionally substituted with 1 to 4 $C_1$-$C_4$-alkyl groups; or —$(CH_2)_mCH(COOR^4)_2$;

wherein m is 0 to 4, and $R^4$ is a $C_1$-$C_4$-alkyl group.

7. The compound according to claim 1, wherein the compound has the structure (I), and wherein n is 0.

8. The compound according to claim 1, wherein Y is a linear or branched organic residue with 1 to 10 carbon atoms.

9. A method for preparing a compound according to claim 1 having the structure (I):

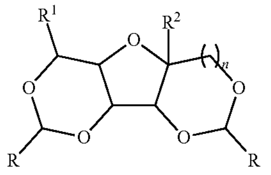

(I)

said method comprising the steps of a. providing a carbohydrate or a lignocellulose-containing composition;

b. adding an aldehyde optionally comprising at least one functional group selected from the group consisting of carboxylic acid, carboxylic amide, ether, alkyne, alkene, aldehyde, chloride, hydroxyl, azide, carboxylic acid ester, aldehyde, vinyl, and amine to the carbohydrate or to the lignocellulose-containing composition to obtain a mixture;

c. heating the mixture under acidic conditions; and d. separating, the compound.

10. The method according to claim 9, wherein the aldehyde of step b) is selected from a group consisting of acetaldehyde, propionaldehyde, isobutyraldehyde, glyoxylic acid, dialdehyde, cyclopropanecarboxaldehyde, isobutyraldehyde, pivaldehyde, tolualdehyde, and benzaldehyde.

11. The method according to claim 9, wherein the carbohydrate or lignocellulose-containing composition is an aldopentose, an aldohexose, an aldoheptose, a ketohexose, a ketoheptose, a lignocellulose-containing composition having a lignin content of 20 to 40 wt. %, based on the total weight of the lignocellulose-containing composition, or a mixture thereof.

12. The method according to claim 9, wherein the aldehyde has the formula:

CHO—$(CH_2)_mCOOH$; CHO—$C_6H_4COOH$, wherein the aromatic ring is optionally substituted with 1 to 4 $C_1$-$C_4$-alkyl groups; CHO—$C_6H_{10}COOH$, wherein the aliphatic ring is optionally substituted with 1 to 4 $C_1$-$C_4$-alkyl groups; or CHO—$(CH_2)_mCH(COOH)_2$, and wherein the method comprises the additional step of adding a $C_1$-$C_4$-alkylalcohol after step c. and before step d.

13. The method according to claim 9, wherein the mixture is heated at 60 to 110° C., and/or wherein the heating is conducted at a pressure of 80 to 120 mbar.

14. The method according to claim 9, wherein step a. comprises providing a lignocellulose-containing composition, wherein the lignocellulose-containing composition is a lignocellulosic biomass.

* * * * *